US012612432B2

(12) United States Patent
Sweeney

(10) Patent No.: US 12,612,432 B2
(45) Date of Patent: Apr. 28, 2026

(54) AAV CAPSID VARIANTS FOR GENE THERAPY

(71) Applicant: University of Florida Research Foundation, Incorporated, Gainesville, FL (US)

(72) Inventor: Hugh Lee Sweeney, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1024 days.

(21) Appl. No.: 17/635,151

(22) PCT Filed: Aug. 14, 2020

(86) PCT No.: PCT/US2020/046543
§ 371 (c)(1),
(2) Date: Feb. 14, 2022

(87) PCT Pub. No.: WO2021/030764
PCT Pub. Date: Feb. 18, 2021

(65) Prior Publication Data
US 2022/0281923 A1 Sep. 8, 2022

Related U.S. Application Data

(60) Provisional application No. 62/886,915, filed on Aug. 14, 2019.

(51) Int. Cl.
*C12N 15/86* (2006.01)
*C07K 14/005* (2006.01)

(52) U.S. Cl.
CPC ............ *C07K 14/005* (2013.01); *C12N 15/86* (2013.01); *C12N 2750/14122* (2013.01);
(Continued)

(58) Field of Classification Search
None
See application file for complete search history.

(56) References Cited

U.S. PATENT DOCUMENTS 10,858,630 B2 * 12/2020 Ho ........................... C12N 7/00
2016/0097040 A1 4/2016 Gao et al.
(Continued)

FOREIGN PATENT DOCUMENTS

JP 2019-513401 A 5/2019
WO WO 2009/137006 A2 11/2009
(Continued)

OTHER PUBLICATIONS

Clement, Nathalie et al., Mol Ther Methods Clin Dev. Mar. 1, 20166; 3:16002. (Year: 2016).*
(Continued)

*Primary Examiner* — Evelyn Y Pyla
*Assistant Examiner* — Jagamya Vijayaraghavan
(74) *Attorney, Agent, or Firm* — Wolf, Greenfield & Sacks, P.C.

(57) ABSTRACT

Adeno associated viral (AAV) particles are emerging as a useful vehicle for gene delivery to various organs and tissues. Provided here are variant AAV capsid proteins and variant capsid protein containing particles. Compositions of these variant AAV particles can be used to alter tissue tropism and transduction efficiency. In some embodiments, compositions described in this application are useful to produce rAAV particles, and/or to deliver one or more genes of interest to a target tissue.

20 Claims, 24 Drawing Sheets

Specification includes a Sequence Listing.

Phylogenetic tree of AAV Alignment SLs 8-2-19.meg ClustalW (Slow/Accurate, Gonnet)
Saturday, August 3, 2019 2:21 PM Amino Acid Substitutions per 100 residues

(52) U.S. Cl.
CPC .............. *C12N 2750/14143* (2013.01); *C12N 2750/14145* (2013.01); *C12N 2750/14171* (2013.01)

(56) References Cited

U.S. PATENT DOCUMENTS

| | | |
|---|---|---|
| 2017/0051257 A1 | 2/2017 | Vandenberghe et al. |
| 2017/0348387 A1 | 12/2017 | Aguirre et al. |
| 2018/0111965 A1 | 4/2018 | Nathwani et al. |
| 2018/0135076 A1 | 5/2018 | Linden |

FOREIGN PATENT DOCUMENTS

| | | | | |
|---|---|---|---|---|
| WO | WO-2015121501 A1 * | 8/2015 | ............. | A61K 48/00 |
| WO | WO-2017015102 A1 * | 1/2017 | ........... | A61K 35/761 |
| WO | WO 2017/136536 A1 | 8/2017 | | |
| WO | WO 2017/180854 A1 | 10/2017 | | |
| WO | WO 2018/218359 A1 | 12/2018 | | |
| WO | WO 2018/152333 A9 | 1/2019 | | |
| WO | WO 2019/025984 A1 | 2/2019 | | |
| WO | WO-2019195449 A1 * | 10/2019 | ......... | A61K 31/7088 |

OTHER PUBLICATIONS

Wang J, Xie J, Lu H, Chen L, Hauck B, Samulski RJ, Xiao W. Existence of transient functional double-stranded DNA intermediates during recombinant AAV transduction. Proc Natl Acad Sci U S A. Aug. 7, 2007;104(32):13104-9. doi: 10.1073/pnas.0702778104. Epub Jul. 30, 2007. PMID: 17664425; PMCID: PMC1941794. (Year: 2007).*

PCT/US2020/046543, Nov. 20, 2020, International Search Report and Written Opinion.

PCT/US2020/046543, Feb. 24, 2022, International Preliminary Report on Patentability.

Partial Supplementary European Search Report for Application No. EP 20853026.1 mailed Aug. 10, 2023.

Extended European Search Report for Application No. EP 20853026.1 mailed Aug. 10, 2023.

Albright et al., Mapping the Structural Determinants Required for AAVrh.10 Transport across the Blood-Brain Barrier. Mol Ther. Feb. 7, 2018;26(2):510-523. doi: 10.1016/j.ymthe.2017.10.017. Epub Oct. 26, 2017.

International Search Report and Written Opinion for International Application No. PCT/US2020/046543 mailed Nov. 20, 2020.

International Preliminary Report on Patentability for International Application No. PCT/US2020/046543 mailed Feb. 24, 2022.

Chen et al., Extracellular superoxide dismutase transgene overexpression preserves postischemic myocardial function in isolated murine hearts. Circulation. Nov. 1, 1996;94(9 Suppl):II412-7.

Chen et al., Protection against myocardial dysfunction induced by global ischemia-reperfusion by antisense-oligodeoxynucleotides directed at beta(1)-adrenoceptor mRNA. J Pharmacol Exp Ther. Aug. 2000;294(2):722-7.

Franz et al., Heart-specific targeting of firefly luciferase by the myosin light chain-2 promoter and developmental regulation in transgenic mice. Circ Res. Oct. 1993;73(4):629-38. doi: 10.1161/01.res.73.4.629.

Kay et al., Targeting photoreceptors via intravitreal delivery using novel, capsid-mutated AAV vectors. PLoS One. Apr. 26, 2013;8(4):e62097. doi: 10.1371/journal.pone.0062097. Erratum in: PLoS One. 2013;8(9). doi:10.1371/annotation/99ee1789-a658-4fb0-8593-40a40e9f344a.

Pulicherla et al., Engineering liver-detargeted AAV9 vectors for cardiac and musculoskeletal gene transfer. Mol Ther. Jun. 2011;19(6):1070-8. doi: 10.1038/mt.2011.22. Epub Mar. 1, 2011.

Woo et al., Recombinant adenovirus-mediated cardiac gene transfer of superoxide dismutase and catalase attenuates postischemic contractile dysfunction. Circulation. Nov. 10, 1998;98(19 Suppl):II255-60; discussion II260-1.

Wu et al., Single amino acid changes can influence titer, heparin binding, and tissue tropism in different adeno-associated virus serotypes. J Virol. Nov. 2006;80(22):11393-7. doi: 10.1128/JVI.01288-06. Epub Aug. 30, 2006.

Yang et al., Critical role of AT1 receptor expression after ischemia/reperfusion in isolated rat hearts: beneficial effect of antisense oligodeoxynucleotides directed at AT1 receptor mRNA. Circ Res. Sep. 7, 1998;83(5):552-9. doi: 10.1161/01.res.83.5.552.

Yang et al., Increase in angiotensin II type 1 receptor expression immediately after ischemia-reperfusion in isolated rat hearts. Circulation. Aug. 5, 1997;96(3):922-6. doi: 10.1161/01.cir.96.3.922.

Zvaritch et al., The transgenic expression of highly inhibitory monomeric forms of phospholamban in mouse heart impairs cardiac contractility. J Biol Chem. May 19, 2000;275(20):14985-91. doi: 10.1074/jbc.275.20.14985.

* cited by examiner

Alignment Workspace of AAV Alignment SLs 8-2-19.meg ClustalW (Slow/Accurate, Gonnet)
Saturday, August 3, 2019 2:19 PM

```
                         G L K H P P P Q I L I K N T P V P A D P P T T F S Q A K L A S F I T Q Y S T G Q
                               650              660              670              680

AAV8 protein             G L K H P P P Q I L I K N T P V P A D P P T T F N Q S K L N S F I T Q Y S T G Q   680
AAV9 Protein             G M K H P P P Q I L I K N T P V P A D P P T A F N K Q K L N S F I T Q Y S T G Q   678
AAVrh10 Protein.pro      G L K H P P P Q I L I K N T P V P A D P P T T F S Q A K L A S F I T Q Y S T G Q   680
AAVrh74 protein seqs     G L K H P P P Q I L I K N T P V P A D P P T T F T K A K L A S F I T Q Y S T G Q   680
AAVanc80L65 Protein      G L K H P P P Q I L I K N T P V P A N P P T T F S P A K F A S F I T Q Y S T G Q   678
SL1.2 Capsid Protein     G L K H P P P Q I L I K N T P V P A D P P T T F N Q S K L N S F I T Q Y S T G Q   680
SL2 Capsid Protein       G L K H P P P Q I L I K N T P V P A D P P T T F S Q A K L A S F I T Q Y S T G Q   680
SL3 Capsid Protein       G L K H P P P Q I L I K N T P V P A D P P T T F S Q A K L A S F I T Q Y S T G Q   680
```

```
                         V S V E I E W E L Q K E N S K R W N P E I Q Y T S N Y Y K S T N V D F A V N T E
                               690              700              710              720

AAV8 protein             V S V E I E W E L Q K E N S K R W N P E I Q Y T S N Y Y K S T S V D F A V N T E   720
AAV9 Protein             V S V E I E W E L Q K E N S K R W N P E I Q Y T S N Y Y K S N N V E F A V N T E   718
AAVrh10 Protein.pro      V S V E I E W E L Q K E N S K R W N P E I Q Y T S N Y Y K S T N V D F A V N T D   720
AAVrh74 protein seqs     V S V E I E W E L Q K E N S K R W N P E I Q Y T S N Y Y K S T N V D F A V N T E   720
AAVanc80L65 Protein      V S V E I E W E L Q K E N S K R W N P E I Q Y T S N Y N K S T N V D F A V D T N   718
SL1.2 Capsid Protein     V S V E I E W E L Q K E N S K R W N P E I Q Y T S N Y Y K S T S V D F A V N T E   720
SL2 Capsid Protein       V S V E I E W E L Q K E N S K R W N P E I Q Y T S N Y Y K S T N V D F A V N T E   720
SL3 Capsid Protein       V S V E I E W E L Q K E N S K R W N P E I Q Y T S N Y Y K S T N V D F A V N T E   720
```

```
                         G X Y S E P R P I G T R Y L T R N L -
                               730

AAV8 protein             G V Y S E P R P I G T R Y L T R N L .                                            739
AAV9 Protein             G V Y S E P R P I G T R Y L T R N L .                                            737
AAVrh10 Protein.pro      G T Y S E P R P I G T R Y L T R N L .                                            739
AAVrh74 protein seqs     G T Y S E P R P I G T R Y L T R N L .                                            739
AAVanc80L65 Protein      G V Y S E P R P I G T R Y L T R N L .                                            737
SL1.2 Capsid Protein     G V Y S E P R P I G T R F L T R N L .                                            739
SL2 Capsid Protein       G T Y S E P R P I G T R F L T R N L .                                            739
SL3 Capsid Protein       G T Y S E P R P I G T R F L T R N L .                                            739
```

(SEQ ID NOS: 7-10, 32, 11, 12, and 13) from top to bottom

FIG. 1E

Sequence pair distances of AAV Alignment SLs 8-2-19.meg ClustalW (Slow/Accurate, Gonnet)
Saturday, August 3, 2019 2:20 PM Percent Identity

| | 1 | 2 | 3 | 4 | 5 | 6 | 7 | 8 | |
|---|---|---|---|---|---|---|---|---|---|
| 1 | | 85.3 | 93.5 | 93.1 | 91.0 | 98.1 | 92.2 | 92.3 | 1 |
| 2 | 16.4 | | 85.8 | 85.8 | 86.4 | 85.8 | 87.5 | 88.3 | 2 |
| 3 | 6.8 | 15.8 | | 98.8 | 91.6 | 93.4 | 96.1 | 88.3 | 3 |
| 4 | 7.3 | 15.8 | 1.2 | | 80.8 | 92.8 | 95.4 | 94.3 | 4 |
| 5 | 9.6 | 15.0 | 8.9 | 9.9 | | 89.6 | 90.9 | 93.6 | 5 |
| 6 | 1.9 | 15.8 | 7.0 | 7.6 | 11.3 | | 93.6 | 91.3 | 6 |
| 7 | 8.3 | 13.7 | 4.0 | 4.8 | 9.7 | 6.7 | | 93.2 | 7 |
| 8 | 8.2 | 12.7 | 5.9 | 6.7 | 9.2 | 7.1 | 1.8 | | 8 |
| | 1 | 2 | 3 | 4 | 5 | 6 | 7 | 8 | |

Divergence

1 AAV8 protein
2 AAV9 Protein
3 AAVrh10 Protein.pro
4 AAVrh74 protein sequence.pro
5 AAVanc80L65 Protein
6 SL1.2 Capsid Protein
7 SL2 Capsid Protein
8 SL3 Capsid Protein

FIG. 3

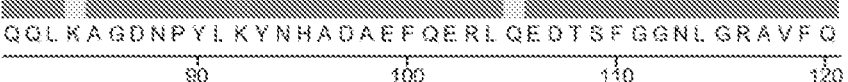

QQLKAGDNPYLKYNHADAEFQERLQEDTSFGGNLGRAVFQ
      90          100          110          120

AAV8 protein          QQLQAGDNPYLRYNHADAEFQERLQEDTSFGGNLGRAVFQ   120
AAV9 Protein          QQLKAGDNPYLKYNHADAEFQERLKEDTSFGGNLGRAVFQ   120
AAVrh10 Protein.pro   QQLKAGDNPYLRYNHADAEFQERLQEDTSFGGNLGRAVFQ   120
AAVrh74 protein sequ  QQLQAGDNPYLRYNHADAEFQERLQEDTSFGGNLGRAVFQ   120
AAVanc80L65 Protein   QQLKAGDNPYLRYNHADAEFQERLQEDTSFGGNLGRAVFQ   120
AAVSL1.2 Protein      QQLQAGDNPYLRYNHADAEFQERLQEDTSFGGNLGRAVFQ   120
AAV SL1.2L Protein S  QQLQAGDNPYLRYNHADAEFQERLQEDTSFGGNLGRAVFQ   120
AAVSL1.2B Protein S   QQLQAGDNPYLRYNHADAEFQERLQEDTSFGGNLGRAVFQ   120
AAVSL1.2LB Protein S  QQLQAGDNPYLRYNHADAEFQERLQEDTSFGGNLGRAVFQ   120
AAVSL2 Protein        QQLKAGDNPYLKYNHADAEFQERLQEDTSFGGNLGRAVFQ   120
AAVSL2L Protein Seq   QQLKAGDNPYLKYNHADAEFQERLQEDTSFGGNLGRAVFQ   120
AAVSL2B Protein Seq   QQLKAGDNPYLKYNHADAEFQERLQEDTSFGGNLGRAVFQ   120
AAVSL2LB Protein Se   QQLKAGDNPYLKYNHADAEFQERLQEDTSFGGNLGRAVFQ   120
AAVSL3 Protein        QQLKAGDNPYLKYNHADAEFQERLKEDTSFGGNLGRAVFQ   120
AAVSL3L Protein Seq   QQLKAGDNPYLKYNHADAEFQERLKEDTSFGGNLGRAVFQ   120
AAVSL3B Protein Seq   QQLKAGDNPYLKYNHADAEFQERLKEDTSFGGNLGRAVFQ   120
AAVSL3LB Protein Se   QQLKAGDNPYLKYNHADAEFQERLKEDTSFGGNLGRAVFQ   120

AKKRVLEPLGLVEEGAKTAPGKKRPVEPSPQRSPDSSAGI
      130         140          150          160

AAV8 protein          AKKRVLEPLGLVEEGAKTAPGKKRPVEPSPQRSPDSSTGI   160
AAV9 Protein          AKKRLLEPLGLVEEAAKTAPGKKRPVEQSPQ-EPDSSAGI   159
AAVrh10 Protein.pro   AKKRVLEPLGLVEEGAKTAPGKKRPVEPSPQRSPDSSTGI   160
AAVrh74 protein sequ  AKKRVLEPLGLVESPVKTAPGKKRPVEPSPQRSPDSSTGI   160
AAVanc80L65 Protein   AKKRVLEPLGLVEEGAKTAPGKKRPVEQSPQ-EPDSSSGI   159
AAVSL1.2 Protein      AKKRVLEPLGLVEEGAKTAPGKKRPVEPSPQRSPDSSAGI   160
AAV SL1.2L Protein S  AKKRVLEPLGLVEEGAKTAPGKKRPVEPSPQRSPDSSAGI   160
AAVSL1.2B Protein S   AKKRVLEPLGLVEEGAKTAPGKKRPVEPSPQRSPDSSAGI   160
AAVSL1.2LB Protein S  AKKRVLEPLGLVEEGAKTAPGKKRPVEPSPQRSPDSSAGI   160
AAVSL2 Protein        AKKRVLEPLGLVEEGAKTAPGKKRPVEPSPQRSPDSSAGI   160
AAVSL2L Protein Seq   AKKRVLEPLGLVEEGAKTAPGKKRPVEPSPQRSPDSSAGI   160
AAVSL2B Protein Seq   AKKRVLEPLGLVEEGAKTAPGKKRPVEPSPQRSPDSSAGI   160
AAVSL2LB Protein Se   AKKRVLEPLGLVEEGAKTAPGKKRPVEPSPQRSPDSSAGI   160
AAVSL3 Protein        AKKRVLEPLGLVEEGAKTAPGKKRPVEPSPQRSPDSSAGI   160
AAVSL3L Protein Seq   AKKRVLEPLGLVEEGAKTAPGKKRPVEPSPQRSPDSSAGI   160
AAVSL3B Protein Seq   AKKRVLEPLGLVEEGAKTAPGKKRPVEPSPQRSPDSSAGI   160
AAVSL3LB Protein Se   AKKRVLEPLGLVEEGAKTAPGKKRPVEPSPQRSPDSSAGI   160

FIG. 4B

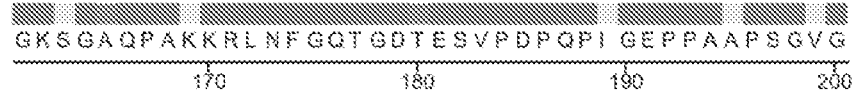

```
                      GKSGAQPAKKRLNFGQTGDTESVPDPQPIGEPPAAPSGVG
                          170          180          190          200
AAV8 protein          GKKGQQPARKRLNFGQTGDSESVPDPQPLGEPPAAPSGVG    200
AAV9 Protein          GKSGAQPAKKRLNFGQTGDTESVPDPQPIGEPPAAPSGVG    199
AAVrh10 Protein.pro   GKKGQQPAKKRLNFGQTGDSESVPDPQPIGEPPAGPSGLG    200
AAVrh74 protein sequ  GKKGQQPAKKRLNFGQTGDSESVPDPQPIGEPPAGPSGLG    200
AAVanc80L65 Protein   GKKGQQPARKRLNFGQTGDSESVPDPQPLGEPPAAPSGVG    199
AAVSL1.2 Protein      GKSGSQPAKKRLNFGQTGDTESVPDPQPIGEPPAAPSGVG    200
AAV SL1.2L Protein S  GKSGSQPAKKRLNFGQTGDTESVPDPQPIGEPPAAPSGVG    200
AAVSL1.2B Protein Se  GKSGSQPAKKRLNFGQTGDTESVPDPQPIGEPPAAPSGVG    200
AAVSL1.2LB Protein S  GKSGSQPAKKRLNFGQTGDTESVPDPQPIGEPPAAPSGVG    200
AAVSL2 Protein        GKSGAQPAKKRLNFGQTGDSESVPDPQPIGEPPAGPSGLG    200
AAVSL2L Protein Seq   GKSGAQPAKKRLNFGQTGDSESVPDPQPIGEPPAGPSGLG    200
AAVSL2B Protein Seq   GKSGAQPAKKRLNFGQTGDSESVPDPQPIGEPPAGPSGLG    200
AAVSL2LB Protein Se   GKSGAQPAKKRLNFGQTGDSESVPDPQPIGEPPAGPSGLG    200
AAVSL3 Protein        GKSGAQPARKRLNFGQTGDTESVPDPQPLGEPPAAPSGVG    200
AAVSL3L Protein Seq   GKSGAQPARKRLNFGQTGDTESVPDPQPLGEPPAAPSGVG    200
AAVSL3B Protein Seq   GKSGAQPARKRLNFGQTGDTESVPDPQPLGEPPAAPSGVG    200
AAVSL3LB Protein Se   GKSGAQPARKRLNFGQTGDTESVPDPQPLGEPPAAPSGVG    200
```

```
                      SNTMAAGGGAPMADNNEGADGVGSASGNWHCDSTWLGDRV
                          210          220          230          240
AAV8 protein          PNTMAAGGGAPMADNNEGADGVGSSSGNWHCDSTWLGDRV    240
AAV9 Protein          SLTMASGGGAPVADNNEGADGVGSSSGNWHCDSQWLGDRV    239
AAVrh10 Protein.pro   SGTMAAGGGAPMADNNEGADGVGSSSGNWHCDSTWLGDRV    240
AAVrh74 protein sequ  SGTMAAGGGAPMADNNEGADGVGSSSGNWHCDSTWLGDRV    240
AAVanc80L65 Protein   SNTMAAGGGAPMADNNEGADGVGNASGNWHCDSTWLGDRV    239
AAVSL1.2 Protein      PNTMAAGGGAPMADNNEGADGVGSSSGNWHCDSTWLGDRV    240
AAV SL1.2L Protein S  PNTMAAGGGAPMADNNEGADGVGSSSGNWHCDSTWLGDRV    240
AAVSL1.2B Protein Se  PNTMAAGGGAPMADNNEGADGVGSSSGNWHCDSTWLGDRV    240
AAVSL1.2LB Protein S  PNTMAAGGGAPMADNNEGADGVGSSSGNWHCDSTWLGDRV    240
AAVSL2 Protein        SNTMAAGGGAPMADNNEGADGVGSASGNWHCDSTWLGDRV    240
AAVSL2L Protein Seq   SNTMAAGGGAPMADNNEGADGVGSASGNWHCDSTWLGDRV    240
AAVSL2B Protein Seq   SNTMAAGGGAPMADNNEGADGVGSASGNWHCDSTWLGDRV    240
AAVSL2LB Protein Se   SNTMAAGGGAPMADNNEGADGVGSASGNWHCDSTWLGDRV    240
AAVSL3 Protein        SNTMAAGGGAPMADNNEGADGVGSASGNWHCDSTWLGDRV    240
AAVSL3L Protein Seq   SNTMAAGGGAPMADNNEGADGVGSASGNWHCDSTWLGDRV    240
AAVSL3B Protein Seq   SNTMAAGGGAPMADNNEGADGVGSASGNWHCDSTWLGDRV    240
AAVSL3LB Protein Se   SNTMAAGGGAPMADNNEGADGVGSASGNWHCDSTWLGDRV    240
```

| | | | |
|---|---|---|---|
| AAV8 protein | I T T S T R T W A L P T Y N N H L Y K Q I S N G T S G G A T N D N T Y F G Y S T | 280 |
| AAV9 Protein | I T T S T R T W A L P T Y N N H L Y K Q I S N S T S G G S S N D N A Y F G Y S T | 279 |
| AAVrh10 Protein.pro | I T T S T R T W A L P T Y N N H L Y K Q I S N G T S G G S T N D N T Y F G Y S T | 280 |
| AAVrh74 protein sequ | T T S T R T W A L P T Y N N H L Y K Q I S N G T S G G S T N D N T Y F G Y S T | 280 |
| AAVanc80L65 Protein | I T T S T R T W A L P T Y N N H L Y K Q I S - S Q S G G S T N D N T Y F G Y S T | 278 |
| AAVSL1.2 Protein | I T T S T R T W A L P T Y N N H L Y K Q I S N G T S G G A T N D N T Y F G Y S T | 280 |
| AAV SL1.2L Protein S | I T T S T R T W A L P T Y N N H L Y K Q I S N G T S G G A T N D N T Y F G Y S T | 280 |
| AAVSL1.2B Protein Se | I T T S T R T W A L P T Y N N H L Y K Q I S S A S T G - A S N D N H Y F G Y S T | 279 |
| AAVSL1.2LB Protein S | I T T S T R T W A L P T Y N N H L Y K Q I S S A S T G - A S N D N H Y F G Y S T | 279 |
| AAVSL2 Protein | I T T S T R T W A L P T Y N N H L Y K Q I S N S T S G G S T N D N T Y F G Y S T | 280 |
| AAVSL2L Protein Seq | T T S T R T W A L P T Y N N H L Y K Q I S N S T S G G S T N D N T Y F G Y S T | 280 |
| AAVSL2B Protein Seq | I T T S T R T W A L P T Y N N H L Y K Q I S - S A S T G A S N D N H Y F G Y S T | 279 |
| AAVSL2LB Protein Se | T T S T R T W A L P T Y N N H L Y K Q I S - S A S T G A S N D N H Y F G Y S T | 279 |
| AAVSL3 Protein | I T T S T R T W A L P T Y N N H L Y K Q I S N S T S G G S T N D N T Y F G Y S T | 280 |
| AAVSL3L Protein Seq | T T S T R T W A L P T Y N N H L Y K Q I S N S T S G G S T N D N T Y F G Y S T | 280 |
| AAVSL3B Protein Seq | I T T S T R T W A L P T Y N N H L Y K Q I S - S A S T G A S N D N H Y F G Y S T | 279 |
| AAVSL3LB Protein Se | T T S T R T W A L P T Y N N H L Y K Q I S - S A S T G A S N D N H Y F G Y S T | 279 |

P W G Y F D F N R F H C H F S P R D W Q R L I N N N W G F R P K K L N F K L F N 290          300          310          320

| | | | |
|---|---|---|---|
| AAV8 protein | P W G Y F D F N R F H C H F S P R D W Q R L I N N N W G F R P K R L S F K L F N | 320 |
| AAV9 Protein | P W G Y F D F N R F H C H F S P R D W Q R L I N N N W G F R P K R L N F K L F N | 319 |
| AAVrh10 Protein.pro | P W G Y F D F N R F H C H F S P R D W Q R L I N N N W G F R P K R L N F K L F N | 320 |
| AAVrh74 protein sequ | P W G Y F D F N R F H C H F S P R D W Q R L I N N N W G F R P K R L N F K L F N | 320 |
| AAVanc80L65 Protein | P W G Y F D F N R F H C H F S P R D W Q R L I N N N W G F R P K K L N F K L F N | 318 |
| AAVSL1.2 Protein | P W G Y F D F N R F H C H F S P R D W Q R L I N N N W G F R P K R L S F K L F N | 320 |
| AAV SL1.2L Protein S | P W G Y F D F N R F H C H F S P R D W Q R L I N N N W G F R P K R L S F K L F N | 320 |
| AAVSL1.2B Protein Se | P W G Y F D F N R F H C H F S P R D W Q R L I N N N W G F R P K R L S F K L F N | 319 |
| AAVSL1.2LB Protein | P W G Y F D F N R F H C H F S P R D W Q R L I N N N W G F R P K R L S F K L F N | 319 |
| AAVSL2 Protein | P W G Y F D F N R F H C H F S P R D W Q R L I N N N W G F R P K K L N F K L F N | 320 |
| AAVSL2L Protein Seq | P W G Y F D F N R F H C H F S P R D W Q R L I N N N W G F R P K K L N F K L F N | 320 |
| AAVSL2B Protein Seq | P W G Y F D F N R F H C H F S P R D W Q R L I N N N W G F R P K K L N F K L F N | 319 |
| AAVSL2LB Protein Se | P W G Y F D F N R F H C H F S P R D W Q R L I N N N W G F R P K K L N F K L F N | 319 |
| AAVSL3 Protein | P W G Y F D F N R F H C H F S P R D W Q R L I N N N W G F R P K K L N F K L F N | 320 |
| AAVSL3L Protein Seq | P W G Y F D F N R F H C H F S P R D W Q R L I N N N W G F R P K K L N F K L F N | 320 |
| AAVSL3B Protein Seq | P W G Y F D F N R F H C H F S P R D W Q R L I N N N W G F R P K K L N F K L F N | 319 |
| AAVSL3LB Protein Se | P W G Y F D F N R F H C H F S P R D W Q R L I N N N W G F R P K K L N F K L F N | 319 |

AAV8 protein           I Q V K E V T Q N E G T K T I A N N L T S T I Q V F T D S E Y Q L P Y V L G S A   360
AAV9 Protein           I Q V K E V T D N N G V K T I A N N L T S T V Q V F T D S D Y Q L P Y V L G S A   359
AAVrh10 Protein.pro    I Q V K E V T Q N E G T K T I A N N L T S T I Q V F T D S E Y Q L P Y V L G S A   360
AAVrh74 protein sequ   I Q V K E V T Q N E G T K T I A N N L T S T I Q V F T D S E Y Q L P Y V L G S A   360
AAVanc80L65 Protein    I Q V K E V T T N D G T T T I A N N L T S T V Q V F T D S E Y Q L P Y V L G S A   358
AAVSL1.2 Protein       I Q V K E V T Q N E G T K T I A N N L T S T I Q V F T D S E Y Q L P Y V L G S A   360
AAV SL1.2L Protein S   I Q V K E V T Q N E G T K T I A N N L T S T I Q V F T D S E Y Q L P Y V L G S A   360
AAVSL1.2B Protein S    I Q V K E V T Q N E G T K T I A N N L T S T I Q V F T D S E Y Q L P Y V L G S A   359
AAVSL1.2LB Protein S   I Q V K E V T Q N E G T K T I A N N L T S T I Q V F T D S E Y Q L P Y V L G S A   359
AAVSL2 Protein         I Q V K E V T Q N E G T K T I A N N L T S T I Q V F T D S D Y Q L P Y V L G S A   360
AAVSL2L Protein Seq    I Q V K E V T Q N E G T K T I A N N L T S T I Q V F T D S D Y Q L P Y V L G S A   360
AAVSL2B Protein Seq    I Q V K E V T Q N E G T K T I A N N L T S T I Q V F T D S D Y Q L P Y V L G S A   359
AAVSL2LB Protein Se    I Q V K E V T Q N E G T K T I A N N L T S T I Q V F T D S D Y Q L P Y V L G S A   359
AAVSL3 Protein         I Q V K E V T Q N E G T K T I A N N L T S T I Q V F T D S D Y Q L P Y V L G S A   360
AAVSL3L Protein Seq    I Q V K E V T Q N E G T K T I A N N L T S T I Q V F T D S D Y Q L P Y V L G S A   360
AAVSL3B Protein Seq    I Q V K E V T Q N E G T K T I A N N L T S T I Q V F T D S D Y Q L P Y V L G S A   359
AAVSL3LB Protein Se    I Q V K E V T Q N E G T K T I A N N L T S T I Q V F T D S D Y Q L P Y V L G S A   359

H E G C L P P F P A D V F M I P Q Y G Y L T L N D G S Q A V G R S S F Y C L E Y
                              370             380             390             400

AAV8 protein           H Q G C L P P F P A D V F M I P Q Y G Y L T L N N G S Q A V G R S S F Y C L E Y   400
AAV9 Protein           H E G C L P P F P A D V F M I P Q Y G Y L T L N D G S Q A V G R S S F Y C L E Y   399
AAVrh10 Protein.pro    H Q G C L P P F P A D V F M I P Q Y G Y L T L N N G S Q A V G R S S F Y C L E Y   400
AAVrh74 protein sequ   H Q G C L P P F P A D V F M I P Q Y G Y L T L N N G S Q A V G R S S F Y C L E Y   400
AAVanc80L65 Protein    H Q G C L P P F P A D V F M I P Q Y G Y L T L N N G S Q A V G R S S F Y C L E Y   398
AAVSL1.2 Protein       H Q G C L P P F P A D V F M I P Q Y G Y L T L N N G S Q A V G R S S F Y C L E Y   400
AAV SL1.2L Protein S   H Q G C L P P F P A D V F M I P Q Y G Y L T L N N G S Q A V G R S S F Y C L E Y   400
AAVSL1.2B Protein S    H Q G C L P P F P A D V F M I P Q Y G Y L T L N N G S Q A V G R S S F Y C L E Y   399
AAVSL1.2LB Protein S   H Q G C L P P F P A D V F M I P Q Y G Y L T L N N G S Q A V G R S S F Y C L E Y   399
AAVSL2 Protein         H E G C L P P F P A D V F M I P Q Y G Y L T L N D G S Q A V G R S S F Y C L E Y   400
AAVSL2L Protein Seq    H E G C L P P F P A D V F M I P Q Y G Y L T L N D G S Q A V G R S S F Y C L E Y   400
AAVSL2B Protein Seq    H E G C L P P F P A D V F M I P Q Y G Y L T L N D G S Q A V G R S S F Y C L E Y   399
AAVSL2LB Protein Se    H E G C L P P F P A D V F M I P Q Y G Y L T L N D G S Q A V G R S S F Y C L E Y   399
AAVSL3 Protein         H E G C L P P F P A D V F M I P Q Y G Y L T L N D G S Q A V G R S S F Y C L E Y   400
AAVSL3L Protein Seq    H E G C L P P F P A D V F M I P Q Y G Y L T L N D G S Q A V G R S S F Y C L E Y   400
AAVSL3B Protein Seq    H E G C L P P F P A D V F M I P Q Y G Y L T L N D G S Q A V G R S S F Y C L E Y   399
AAVSL3LB Protein Se    H E G C L P P F P A D V F M I P Q Y G Y L T L N D G S Q A V G R S S F Y C L E Y   399
```

FIG. 4E

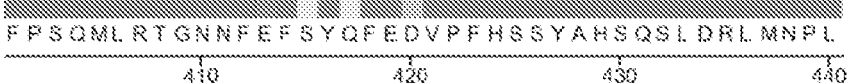

```
            F P S Q M L R T G N N F E F S Y Q F E D V P F H S S Y A H S Q S L D R L M N P L
            ------------------------------------------------------------------------------
                   410            420            430            440
AAV8 protein        F P S Q M L R T G N N F Q F T Y T F E D V P F H S S Y A H S Q S L D R L M N P L   440
AAV9 Protein        F P S Q M L R T G N N F Q F S Y E F E N V P F H S S Y A H S Q S L D R L M N P L   439
AAVrh10 Protein,pro F P S Q M L R T G N N F E F S Y Q F E D V P F H S S Y A H S Q S L D R L M N P L   440
AAVrh74 protein sequ F P S Q M L R T G N N F E F S Y N F E D V P F H S S Y A H S Q S L D R L M N P L  440
AAVanc80L65 Protein F P S Q M L R T G N N F Q F S Y T F E D V P F H S S Y A H S Q S L D R L M N P L   438
AAVSL1.2 Protein    F P S Q M L R T G N N F Q F T Y Q F E D V P F H S S Y A H S Q S L D R L M N P L   440
AAV SL1.2L Protein S F P S Q M L R T G N N F Q F T Y Q F E D V P F H S S Y A H S Q S L D R L M N P L  440
AAVSL1.2B Protein Se F P S Q M L R T G N N F Q F T Y Q F E D V P F H S S Y A H S Q S L D R L M N P L  439
AAVSL1.2LB Protein S F P S Q M L R T G N N F Q F T Y Q F E D V P F H S S Y A H S Q S L D R L M N P L  439
AAVSL2 Protein      F P S Q M L R T G N N F E F S Y Q F E D V P F H S S Y A H S Q S L D R L M N P L   440
AAVSL2L Protein Seq F P S Q M L R T G N N F E F S Y Q F E D V P F H S S Y A H S Q S L D R L M N P L   440
AAVSL2B Protein Seq F P S Q M L R T G N N F E F S Y Q F E D V P F H S S Y A H S Q S L D R L M N P L   439
AAVSL2LB Protein Se F P S Q M L R T G N N F E F S Y Q F E D V P F H S S Y A H S Q S L D R L M N P L   439
AAVSL3 Protein      F P S Q M L R T G N N F E F S Y Q F E D V P F H S S Y A H S Q S L D R L M N P L   440
AAVSL3L Protein Seq F P S Q M L R T G N N F E F S Y Q F E D V P F H S S Y A H S Q S L D R L M N P L   440
AAVSL3B Protein Seq F P S Q M L R T G N N F E F S Y Q F E D V P F H S S Y A H S Q S L D R L M N P L   439
AAVSL3LB Protein Se F P S Q M L R T G N N F E F S Y Q F E D V P F H S S Y A H S Q S L D R L M N P L   439
```

```
            I D Q Y L Y F L S R T Q S T G G T A G T Q Q L L F S Q A G P S N M S A Q A K N W
            ------------------------------------------------------------------------------
                   450            460            470            480
AAV8 protein        I D Q Y L Y Y L S R T Q T T G G T A N T Q T L G F S Q G G P N T M A N Q A K N W   480
AAV9 Protein        I D Q Y L Y Y L S K T I N G S G Q N - Q Q T L K F S V A G P S N M A V Q G R N Y   478
AAVrh10 Protein,pro I D Q Y L Y Y L S R T Q S T G G T A G T Q Q L L F S Q A G P N N M S A Q A K N W   480
AAVrh74 protein sequ I D Q Y L Y Y L S R T Q S T G G T A G T Q Q L L F S Q A G P N N M S A Q A K N W  480
AAVanc80L65 Protein I D Q Y L Y Y L S R T Q T T S G T A G N R T L Q F S Q A G P S S M A N Q A K N W   478
AAVSL1.2 Protein    I D Q Y L Y F L S R T Q T T G G T A N T Q Q L L F S Q G G P N T M A N Q A K N W   480
AAV SL1.2L Protein S I D Q Y L Y F L S R T Q T T G G T A N T Q Q L L F S Q G G P N T M A N Q A K N W  480
AAVSL1.2B Protein Se I D Q Y L Y F L S R T Q T T G G T A N T Q Q L L F S Q G G P N T M A N Q A K N W  479
AAVSL1.2LB Protein S I D Q Y L Y F L S R T Q T T G G T A N T Q Q L L F S Q G G P N T M A N Q A K N W  479
AAVSL2 Protein      I D Q Y L Y F L S R T Q S T G G T A G T Q Q L L F S Q A G P S N M S A Q A K N W   480
AAVSL2L Protein Seq I D Q Y L Y F L S R T Q S T G G T A G T Q Q L L F S Q A G P S N M S A Q A K N W   480
AAVSL2B Protein Seq I D Q Y L Y F L S R T Q S T G G T A G T Q Q L L F S Q A G P S N M S A Q A K N W   479
AAVSL2LB Protein Se I D Q Y L Y F L S R T Q S T G G T A G T Q Q L L F S Q A G P S N M S A Q A K N W   479
AAVSL3 Protein      I D Q Y L Y F L S R T Q S T G G T A G T Q Q L L F S Q A G P S N M S A Q A K N W   480
AAVSL3L Protein Seq D Q Y L Y F L S R T Q S T G G T A G T Q Q L L F S Q A G P S N M S A Q A K N W   480
AAVSL3B Protein Seq D Q Y L Y F L S R T Q S T G G T A G T Q Q L L F S Q A G P S N M S A Q A K N W   479
AAVSL3LB Protein Se D Q Y L Y F L S R T Q S T G G T A G T Q Q L L F S Q A G P S N M S A Q A K N W   479
```

FIG. 4F

```
                              L P G P C Y R Q Q R V S T V T N Q N N N S N F A W T G A T K Y H L N G R D S L V
                                        490                500                510                520

AAV8 protein              L P G P C Y R Q Q R V S T T T G Q N N N S N F A W T A G T K Y H L N G R N S L A   520
AAV9 Protein              I P G P S Y R Q Q R V S T T V T Q N N N S E F A W P G A S S W A L N G R N S L M   518
AAVrh10 Protein.pro       L P G P C Y R Q Q R V S T T L S Q N N N S N F A W T G A T K Y H L N G R D S L V   520
AAVrh74 protein sequ      L P G P C Y R Q Q R V S T T L S Q N N N S N F A W T G A T K Y H L N G R D S L V   520
AAVanc80L65 Protein       L P G P C Y R Q Q R V S K T T N Q N N N S N F A W T G A T K Y H L N G R D S L V   518
AAVSL1.2 Protein          L P G P C Y R Q Q R V S T V T G Q N N N S N F A W T A G T K Y H L N G R N S L A   520
AAV SL1.2L Protein S      L P G P C Y R Q Q R V S T V T G Q N N I S N F A W T A G T K Y H L N G R N S L A   520
AAVSL1.2B Protein S       L P G P C Y R Q Q R V S T V T G Q N N N S N F A W T A G T K Y H L N G R N S L A   519
AAVSL1.2LB Protein        L P G P C Y R Q Q R V S T V T G Q N N I S N F A W T A G T K Y H L N G R N S L A   519
AAVSL2 Protein            L P G P C Y R Q Q R V S T V T N Q N N N S N F A W T G A T K Y H L N G R D S L V   520
AAVSL2L Protein Seq       L P G P C Y R Q Q R V S T V T N Q N N I S N F A W T G A T K Y H L N G R D S L V   520
AAVSL2B Protein Seq       L P G P C Y R Q Q R V S T V T N Q N N N S N F A W T G A T K Y H L N G R D S L V   519
AAVSL2LB Protein Se       L P G P C Y R Q Q R V S T V T N Q N N I S N F A W T G A T K Y H L N G R D S L V   519
AAVSL3 Protein            L P G P C Y R Q Q R V S T V T N Q N N N S N F A W T G A T K Y H L N G R D S L V   520
AAVSL3L Protein Seq       L P G P C Y R Q Q R V S T V T N Q N N I S N F A W T G A T K Y H L N G R D S L V   520
AAVSL3B Protein Seq       L P G P C Y R Q Q R V S T V T N Q N N N S N F A W T G A T K Y H L N G R D S L V   519
AAVSL3LB Protein Se       L P G P C Y R Q Q R V S T V T N Q N N I S N F A W T G A T K Y H L N G R D S L V   519

N P G I A M A S H K E G E E R F F P S S G I L I F G K Q G A G R D N V D Y S K V
                                        530                540                550                560

AAV8 protein              N P G I A M A T H K D D E E R F F P S N G I L I F G K Q N A A R D N A D Y S D V   560
AAV9 Protein              N P G P A M A S H K E G E D R F F P L S G S L I F G K Q G T G R D N V D A D K V   558
AAVrh10 Protein.pro       N P G V A M A T H K D D E E R F F P S S G V L M F G K Q G A G K D N V D Y S S V   560
AAVrh74 protein sequ      N P G V A M A T H K D D E E R F F P S S G V L M F G K Q G A G K D N V D Y S S V   560
AAVanc80L65 Protein       N P G P A M A T H K D D E D K F F P M S G V L I F G K Q G A G N S N V D L D N V   558
AAVSL1.2 Protein          N P G I A M A T H K D D E E R F F P S N G I L I F G K Q N A A R D N A D Y S K V   560
AAV SL1.2L Protein S      N P G I A M A T H K D D E E R F F P S N G I L I F G K Q N A A R D N A D Y S K V   560
AAVSL1.2B Protein S       N P G I A M A T H K D D E E R F F P S N G I L I F G K Q N A A R D N A D Y S K V   559
AAVSL1.2LB Protein        N P G I A M A T H K D D E E R F F P S N G I L I F G K Q N A A R D N A D Y S K V   559
AAVSL2 Protein            N P G I A M A S H K E G E E R F F P S S G I L I F G K Q G A G R D N V D Y S K V   560
AAVSL2L Protein Seq       N P G I A M A S H K E G E E R F F P S S G I L I F G K Q G A G R D N V D Y S K V   560
AAVSL2B Protein Seq       N P G I A M A S H K E G E E R F F P S S G I L I F G K Q G A G R D N V D Y S K V   559
AAVSL2LB Protein Se       N P G I A M A S H K E G E E R F F P S S G I L I F G K Q G A G R D N V D Y S K V   559
AAVSL3 Protein            N P G I A M A S H K E G E E R F F P S S G I L I F G K Q G A G R D N V D Y S K V   560
AAVSL3L Protein Seq       N P G I A M A S H K E G E E R F F P S S G I L I F G K Q G A G R D N V D Y S K V   560
AAVSL3B Protein Seq       N P G I A M A S H K E G E E R F F P S S G I L I F G K Q G A G R D N V D Y S K V   559
AAVSL3LB Protein Se       N P G I A M A S H K E G E E R F F P S S G I L I F G K Q G A G R D N V D Y S K V   559
```

FIG. 4G

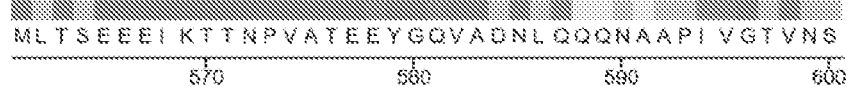

```
                  M L T S E E E I K T T N P V A T E E Y G Q V A D N L Q Q Q N A A P I V G T V N S
                           |              |              |              |
                          570            580            590            600

AAV8 protein        M L T S E E E I K T T N P V A T E E Y G I V A D N L Q Q Q N T A P Q I G T V N S    600
AAV9 Protein        M I T N E E E I K T T N P V A T E S Y G Q V A T N H S A Q A Q A Q T G W V Q N    598
AAVrh10 Protein.pro M L T S E E E I K T T N P V A T E Q Y G V V A D N L Q Q Q N A A P I V G A V N S    600
AAVrh74 protein sequ M L T S E E E I K T T N P V A T E Q Y G V V A D N L Q Q Q N A A P I V G A V N S    600
AAVanc80L65 Protein M I T N E E E I K T T N P V A T E E Y G T V A T N L Q S A N T A P A T G T V N S    598
AAVSL1.2 Protein    M L T S E E E I K T T N P V A T E E Y G I V A D N L Q Q Q N A A P Q I G T V N S    600
AAV SL1.2L Protein S M L T S E E E I K T T N P V A T E E Y G I V A D N L Q Q Q N A A P Q I G T V N S    600
AAVSL1.2B Protein Se M L T S E E E I K T T N P V A T E E Y G I V A D N L Q Q Q N A A P Q I G T V N S    599
AAVSL1.2LB Protein S M L T S E E E I K T T N P V A T E E Y G I V A D N L Q Q Q N A A P Q I G T V N S    599
AAVSL2 Protein      M L T S E E E I K T T N P V A T E Q Y G Q V A D N L Q Q Q N A A P I V G T V N S    600
AAVSL2L Protein Seq M L T S E E E I K T T N P V A T E Q Y G Q V A D N L Q Q Q N A A P I V G T V N S    600
AAVSL2B Protein Seq M L T S E E E I K T T N P V A T E Q Y G Q V A D N L Q Q Q N A A P I V G T V N S    599
AAVSL2LB Protein Se M L T S E E E I K T T N P V A T E Q Y G Q V A D N L Q Q Q N A A P I V G T V N S    599
AAVSL3 Protein      M L T S E E E I K T T N P V A T E E Y G Q V A D N L Q S A N T A P I V G T V N S    600
AAVSL3L Protein Seq M L T S E E E I K T T N P V A T E E Y G Q V A D N L Q S A N T A P I V G T V N S    600
AAVSL3B Protein Seq M L T S E E E I K T T N P V A T E E Y G Q V A D N L Q S A N T A P I V G T V N S    599
AAVSL3LB Protein Se M L T S E E E I K T T N P V A T E E Y G Q V A D N L Q S A N T A P I V G T V N S    599
```

```
                  Q G A L P G M V W Q N R D V Y L Q G P I W A K I P H T D G N F H P S P L M G G F
                           |              |              |              |
                          610            620            630            640

AAV8 protein        Q G A L P G M V W Q N R D V Y L Q G P I W A K I P H T D G N F H P S P L M G G F    640
AAV9 Protein        Q G I L P G M V W Q D R D V Y L Q G P I W A K I P H T D G N F H P S P L M G G F    638
AAVrh10 Protein.pro Q G A L P G M V W Q N R D V Y L Q G P I W A K I P H T D G N F H P S P L M G G F    640
AAVrh74 protein sequ Q G A L P G M V W Q N R D V Y L Q G P I W A K I P H T D G N F H P S P L M G G F    640
AAVanc80L65 Protein Q G A L P G M V W Q D R D V Y L Q G P I W A K I P H T D G H F H P S P L M G G F    638
AAVSL1.2 Protein    Q G A L P G M V W Q N R D V Y L Q G P I W A K I P H T D G N F H P S P L M G G F    640
AAV SL1.2L Protein S Q G A L P G M V W Q N R D V Y L Q G P I W A K I P H T D G N F H P S P L M G G F    640
AAVSL1.2B Protein Se Q G A L P G M V W Q N R D V Y L Q G P I W A K I P H T D G N F H P S P L M G G F    639
AAVSL1.2LB Protein S Q G A L P G M V W Q N R D V Y L Q G P I W A K I P H T D G N F H P S P L M G G F    639
AAVSL2 Protein      Q G A L P G M V W Q N R D V Y L Q G P I W A K I P H T D G N F H P S P L M G G F    640
AAVSL2L Protein Seq Q G A L P G M V W Q N R D V Y L Q G P I W A K I P H T D G N F H P S P L M G G F    640
AAVSL2B Protein Seq Q G A L P G M V W Q N R D V Y L Q G P I W A K I P H T D G N F H P S P L M G G F    639
AAVSL2LB Protein Se Q G A L P G M V W Q N R D V Y L Q G P I W A K I P H T D G N F H P S P L M G G F    639
AAVSL3 Protein      Q G A L P G M V W Q N R D V Y L Q G P I W A K I P H T D G N F H P S P L M G G F    640
AAVSL3L Protein Seq Q G A L P G M V W Q N R D V Y L Q G P I W A K I P H T D G N F H P S P L M G G F    640
AAVSL3B Protein Seq Q G A L P G M V W Q N R D V Y L Q G P I W A K I P H T D G N F H P S P L M G G F    639
AAVSL3LB Protein Se Q G A L P G M V W Q N R D V Y L Q G P I W A K I P H T D G N F H P S P L M G G F    639
```

AAV6 protein         G V Y S E P R P I  G T R Y L T R N L ,          739
AAV9 Protein         G V Y S E P R P I  G T R Y L T R N L ,          737
AAVrh10 Protein.pro  G T Y S E P R P I  G T R Y L T R N L ,          739
AAVrh74 protein sequ G T Y S E P R P I  G T R Y L T R N L ,          739
AAVanc80L65 Protein  G V Y S E P R P I  G T R Y L T R N L ,          737
AAVSL1.2 Protein     G V Y S E P R P I  G T R F L T R N L ,          739
AAV SL1.2L Protein S G V Y S E P R P I  G T R F L T R N L ,          739
AAVSL1.2B Protein Se G V Y S E P R P I  G T R F L T R N L ,          738
AAVSL1.2LB Protein S G V Y S E P R P I  G T R F L T R N L ,          738
AAVSL2 Protein       G T Y S E P R P I  G T R F L T R N L ,          739
AAVSL2L Protein Seq  G T Y S E P R P I  G T R F L T R N L ,          739
AAVSL2B Protein Seq  G T Y S E P R P I  G T R F L T R N L ,          738
AAVSL2LB Protein Se  G T Y S E P R P I  G T R F L T R N L ,          738
AAVSL3 Protein       G T Y S E P R P I  G T R F L T R N L ,          739
AAVSL3L Protein Seq  G T Y S E P R P I  G T R F L T R N L ,          739
AAVSL3B Protein Seq  G T Y S E P R P I  G T R F L T R N L ,          738
AAVSL3LB Protein Se  G T Y S E P R P I  G T R F L T R N L ,          738
```

(SEQ ID NOS: 7-10, 32, 11, 15, 21, 27, 12, 17, 23, 29, 13, 19, 25, and 31) from top to bottom

FIG. 4J

Percent Identity

| | | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|---|
| AAV8 protein | 1 | | 85.3 | 93.5 | 93.1 | 91.0 | 98.1 | 98.0 | 97.3 | 97.2 | 92.2 | 92.0 | 91.7 | 91.6 | 92.3 | 92.2 | 91.9 | 91.7 | 1 |
| AAV9 Protein | 2 | 16.4 | | 85.8 | 85.8 | 86.4 | 85.8 | 85.6 | 85.5 | 85.3 | 87.5 | 87.4 | 87.2 | 87.1 | 88.3 | 88.2 | 88.0 | 87.9 | 2 |
| AAVrh10 Protein.pro | 3 | 6.6 | 15.8 | | 98.8 | 91.6 | 93.4 | 93.2 | 92.5 | 92.4 | 96.1 | 95.9 | 95.4 | 95.3 | 94.3 | 94.2 | 93.6 | 93.5 | 3 |
| AAVrh74 protein sequence.pro | 4 | 7.3 | 15.8 | 1.2 | | 90.8 | 93.8 | 92.7 | 93.0 | 91.9 | 95.4 | 95.3 | 94.7 | 94.6 | 93.6 | 93.5 | 93.0 | 92.8 | 4 |
| AAVanc80L65 Protein | 5 | 9.6 | 15.0 | 8.9 | 9.9 | | 89.6 | 89.4 | 89.1 | 89.0 | 90.9 | 90.8 | 90.4 | 90.2 | 91.3 | 91.2 | 90.8 | 90.6 | 5 |
| AAVSL1.2 Protein | 6 | 1.9 | 15.8 | 7.0 | 7.6 | 11.3 | | 99.9 | 99.2 | 99.1 | 93.6 | 93.5 | 93.2 | 93.1 | 93.2 | 93.1 | 92.8 | 92.7 | 6 |
| AAV SL1.2L Protein Sequence | 7 | 2.1 | 16.0 | 7.1 | 7.7 | 11.4 | 0.1 | | 99.1 | 99.2 | 93.5 | 93.6 | 93.3 | 93.2 | 93.1 | 93.2 | 92.7 | 92.8 | 7 |
| AAVSL1.2B Protein Sequence | 8 | 2.6 | 16.2 | 7.9 | 6.5 | 11.6 | 0.8 | 1.0 | | 99.9 | 93.5 | 93.6 | 93.1 | 93.2 | 93.1 | 93.2 | 92.7 | 92.6 | 8 |
| AAVSL1.2LB Protein Sequence | 9 | 2.9 | 16.4 | 8.0 | 8.6 | 11.9 | 1.0 | 1.0 | 0.1 | | 93.0 | 92.8 | 93.4 | 93.4 | 92.5 | 92.4 | 92.9 | 92.6 | 9 |
| AAVSL2 Protein | 10 | 8.3 | 13.7 | 4.0 | 4.8 | 9.7 | 6.7 | 6.8 | 7.4 | 7.6 | | 99.9 | 99.3 | 99.2 | 99.2 | 98.1 | 97.6 | 97.4 | 10 |
| AAVSL2L Protein Sequence | 11 | 8.5 | 13.9 | 4.2 | 4.9 | 9.9 | 6.8 | 6.7 | 7.6 | 7.4 | 0.1 | | 99.9 | 98.3 | 98.1 | 98.2 | 97.4 | 97.6 | 11 |
| AAVSL2B Protein Sequence | 12 | 8.8 | 14.0 | 4.8 | 5.5 | 10.3 | 7.1 | 7.3 | 7.0 | 7.1 | 0.8 | 0.8 | | 99.9 | 99.2 | 99.3 | 98.2 | 98.1 | 12 |
| AAVSL2LB Protein Sequence | 13 | 8.9 | 14.2 | 4.9 | 5.8 | 10.5 | 7.3 | 7.1 | 7.1 | 7.0 | 0.7 | 0.7 | 0.1 | | 98.3 | 98.1 | 98.2 | 97.6 | 13 |
| AAVSL3 Protein | 14 | 8.2 | 12.7 | 5.9 | 6.7 | 9.2 | 7.1 | 7.3 | 7.9 | 8.0 | 0.8 | 1.9 | 2.5 | 2.6 | | 99.9 | 99.3 | 99.2 | 14 |
| AAVSL3L Protein Sequence | 15 | 8.3 | 12.9 | 6.1 | 6.8 | 9.4 | 7.3 | 7.1 | 8.0 | 7.9 | 1.8 | 1.8 | 2.6 | 2.5 | 0.1 | | 99.2 | 99.3 | 15 |
| AAVSL3B Protein Sequence | 16 | 8.6 | 13.1 | 6.7 | 7.4 | 9.9 | 7.6 | 7.7 | 7.4 | 7.6 | 1.9 | 2.6 | 1.8 | 1.9 | 0.7 | 0.8 | | 99.9 | 16 |
| AAVSL3LB Protein Sequence | 17 | 8.8 | 13.2 | 6.8 | 7.6 | 10.0 | 7.7 | 7.6 | 7.6 | 7.4 | 2.6 | 2.5 | 1.9 | 1.8 | 0.8 | 0.7 | 0.1 | | 17 |
| | | 1 | 2 | 3 | 4 | 5 | 6 | 7 | 8 | 9 | 10 | 11 | 12 | 13 | 14 | 15 | 16 | 17 | |

Divergence

FIG. 6

SEQUENCE LISTING

<160> NUMBER OF SEQ ID NOS: 32

<210> SEQ ID NO 1
<211> LENGTH: 2217
<212> TYPE: DNA
<213> ORGANISM: Artificial Sequence
<220> FEATURE:
<223> OTHER INFORMATION: Synthetic

<400> SEQUENCE: 1

```
atggctgccg atggttatct tccagattgg ctcgaggaca acctctctga gggcattcgc       60
gagtggtggg cgctgaaacc tggagccccg aagcccaaag ccaaccagca aaagcaggac      120
gacggccggg gtctggtgct tcctggctac aagtacctcg gacccttcaa cggactcgac      180 aaggggagc ccgtcaacgc ggcggacgca gcggccctcg agcacgacaa ggcctacgac      240
cagcagctgc aggcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccggtaga gccatcaccc agcgttctc cagactcctc tgcgggcatc      480
ggcaagtcgg gctcacagcc cgccaaaaaa gactcaatt ttggtcagac tggcgacaca      540
gagtcagttc cagaccctca acctatcgga gaacctccag cagcgccctc tggtgtggga      600
cctaatacaa tggctgcagg cggtggcgca ccaatggcag acaataacga aggcgccgac      660
ggagtgggta gttcctcggg aaattggcat tgcgattcca catggctggg cgacagagtc      720
atcaccacca gcacccgaac ctgggccctg cccacctaca acaaccacct ctacaagcaa      780
atctccaacg ggacatcggg aggagccacc aacgacaaca cctacttcgg ctacagcacc      840
ccctgggggt attttgactt taacagattc cactgccact tttcaccacg tgactggcag      900
cgactcatca caacaactg gggattccgg cccaagagac tcagcttcaa gctcttcaac      960
atccaggtca aggaggtcac gcagaatgaa ggcaccaaga ccatcgccaa taacctcacc     1020
agcaccatcc aggtgtttac ggactcggag taccagctgc cgtacgttct cggctctgcc     1080
caccagggct gcctgcctcc gttcccggcg gacgtgttca tgattcccca gtacggctac     1140
ctaacactca acaacggtag tcaggccgtg ggacgctcct ccttctactg cctggaatac     1200
tttccttcgc agatgctgag aaccggcaac aacttccagt ttacttacca gttcgaggac     1260 gtgccttttcc acagcagcta cgcccacagc cagagcttgg accggctgat gaatcctctg     1320
attgaccagt acctgtactt cttgtctcgg actcaaacaa caggaggcac ggcaaatacg     1380
cagcagctgc tattcagcca aggtgggcct aatacaatgg ccaatcaggc aaagaactgg     1440
ctgccaggac cctgttaccg ccaacaacgc gtctcaacgg taaccgggca aaacaacaat     1500
agcaactttg cctggactgc tgggaccaaa taccatctga atggaagaaa ttcattggct     1560
aatcctggca tcgctatggc aacacacaaa gacgacgagg agcgtttttt tcccagtaac     1620
gggatcctga tttttggcaa acaaaatgct gccagagaca atgcggatta cagcaaagtc     1680
atgctcacca gcgaggaaga aatcaaaacc actaaccctg tggctacaga ggaatacggt     1740
atcgtggcag ataacttgca gcagcaaaac gccgctcctc aaattggaac tgtcaacagc     1800
cagggggcct acccggtat ggtctggcag aaccgggacg tgtacctgca gggtcccatc     1860
tgggccaaga ttcctcacac ggacggcaac ttccaccgt ctccgctgat gggcggcttt     1920
ggcctgaaac atcctccgcc tcagatcctg atcaagaaca cgcctgtacc tgcggatcct     1980
ccgaccacct tcaaccagtc aaagctgaac tctttcatca cgcaatacag caccggacag     2040
```

-continued

```
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgtttcc tcacccgtaa tctgtaa      2217
```

```
<210> SEQ ID NO 2
<211> LENGTH: 738
<212> TYPE: PRT
<213> ORGANISM: Artificial Sequence
<220> FEATURE:
<223> OTHER INFORMATION: Synthetic

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ser Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335
```

-continued

```
Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Phe Leu
                435                 440                 445

Ser Arg Thr Gln Thr Thr Gly Gly Thr Ala Asn Thr Gln Gln Leu Leu
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Val Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
            530                 535                 540

Phe Gly Lys Gln Asn Ala Ala Arg Asp Asn Ala Asp Tyr Ser Lys Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Ala Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Phe Leu Thr Arg
                725                 730                 735

Asn Leu
```

-continued

```
<210> SEQ ID NO 3
<211> LENGTH: 2217
<212> TYPE: DNA
<213> ORGANISM: Artificial Sequence
<220> FEATURE:
<223> OTHER INFORMATION: Synthetic

<400> SEQUENCE: 3
atggctgccg atggttatct tccagattgg ctcgaggaca acctctctga gggcattcgc      60
gagtggtggg acttgaaacc tggagccccg aaacccaaag ccaaccagca aaagcaggac     120
aacggccggg gtctggtgct tcctggctac aagtacctcg gacccttcaa cggactcgac     180 aaggggggagc ccgtcaacgc ggcggacgca gcggccctcg agcacgacaa ggcctacgac     240
cagcagctca aagcgggtga caatccgtac ctgaagtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gcgcacagcc cgcgaaaaag agactcaact ttgggcagac tggcgactca     540
gagtcagtgc ccgaccctca accaatcgga gaaccccccg caggcccctc tggtctggga     600
tctaatacaa tggctgcagg cggtggcgct ccaatggcag acaataacga aggcgccgac     660
ggagtgggta gtgcctcagg aaaattggcat tgcgattcca catggctggg cgacagagtc     720
atcaccacca gcacccgaac ctgggccctc cccacctaca acaaccacct ctacaagcaa     780
atctccaaca gcacttcggg aggaagcacc aacgacaaca cctacttcgg ctacagcacc     840
ccctgggggt attttgactt taacagattc cactgccact tctcaccacg tgactggcag     900
cgactcatca caacaactg gggattccgg cccaagaaac tcaacttcaa gctcttcaac     960
atccaggtca aggaggtcac gcagaatgaa ggcaccaaga ccatcgccaa taaccttacc    1020
agcacgattc aggtctttac ggactcggac taccagctcc cgtacgtcct cggctctgcg    1080
cacgagggct gcctgcctcc gttcccggcg gacgtcttca tgattcctca gtacgggtac    1140
ctgactctga cgatggcag tcaggccgtg ggccgttcct ccttctactg cctggagtac    1200
tttccttctc aaatgctgag aacgggcaac aactttgagt tcagctacca gtttgaggac    1260
gtgccttttc acagcagcta cgcgcacagc caaagcctgg accggctgat gaaccccctc    1320
atcgaccagt acctgtactt cctgtctcgg actcagtcca cgggaggtac cgcaggaact    1380
cagcagttgc tattttctca ggccgggcct agcaacatgt cggctcaggc caaaaactgg    1440
ctacccgggc cctgctaccg gcagcaacgc gtctccacgg taaccaacca aaataacaac    1500
agcaactttg cctggaccgg tgccaccaag tatcatctga atggcagaga ctctctggta    1560 aatccggta tcgctatggc aagccacaag aaggagaag agcgatttt tccgtccagc    1620 ggaatcttaa tttttgggaa acagggagct ggaagagaca acgtggacta tagcaaagtt    1680
atgctaacca gtgaggaaga aattaaaacc accaacccag tggccacaga acagtacggc    1740
caagtggccg ataacctgca acagcaaaac gccgctccta ttgtagggac tgtcaacagt    1800
caaggagcct tacctggcat ggtctggcag aaccgggacg tgtacctgca gggtcctatc    1860
tgggccaaga ttcctcacac ggacggaaac tttcatccct cgccgctgat gggaggcttt    1920
ggactgaaac acccgcctcc tcagatcctg attaagaata cacctgttcc cgcggatcct    1980
ccaactacct tcagtcaagc taagctggcg tcgttcatca cgcagtacag caccggacag    2040
gtcagcgtgg aaattgaatg ggagctgcag aaagaaaaca gcaaacgctg gaacccagag    2100
```

-continued attcaataca cttccaacta ctacaaatct acaaatgtgg actttgctgt taacacagaa     2160
ggcacttatt ctgagcctcg ccccatcggc accgtttcc tcacccgtaa tctgtaa       2217

<210> SEQ ID NO 4
<211> LENGTH: 738
<212> TYPE: PRT
<213> ORGANISM: Artificial Sequence
<220> FEATURE:
<223> OTHER INFORMATION: Synthetic

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Asn Thr Met Ala Ala Gly Gly
            195                 200                 205

Gly Ala Pro Met Ala Asp Asn Asn Glu Gly Ala Asp Gly Val Gly Ser
        210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Ser Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Lys Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Asp Tyr Gln
            340                 345                 350

-continued

```
Leu Pro Tyr Val Leu Gly Ser Ala His Glu Gly Cys Leu Pro Pro Phe
        355                 360                 365

Pro Ala Asp Val Phe Met Ile Pro Gln Tyr Gly Tyr Leu Thr Leu Asn
    370                 375                 380

Asp Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Phe Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Val Thr Asn
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Ile Ala Met Ala Ser
            515                 520                 525

His Lys Glu Gly Glu Glu Arg Phe Phe Pro Ser Ser Gly Ile Leu Ile
        530                 535                 540

Phe Gly Lys Gln Gly Ala Gly Arg Asp Asn Val Asp Tyr Ser Lys Val
545                 550                 555                 560

Met Leu Thr Ser Glu Glu Glu Ile Lys Thr Thr Asn Pro Val Ala Thr
                565                 570                 575

Glu Gln Tyr Gly Gln Val Ala Asp Asn Leu Gln Gln Gln Asn Ala Ala
                580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Phe Leu Thr Arg
                725                 730                 735

Asn Leu
```

<210> SEQ ID NO 5
<211> LENGTH: 2217
<212> TYPE: DNA

-continued

```
<213> ORGANISM: Artificial Sequence
<220> FEATURE:
<223> OTHER INFORMATION: Synthetic

<400> SEQUENCE: 5
atggctgccg atggttatct tccagattgg ctcgaggaca acctctctga gggcattcgc      60
gagtggtggg ctttgaaacc tggagccccg caacccaaag ccaaccagca aaagcaggac     120
aacgctcggg gtctggtgct tcctggctac aagtacctcg gacccttcaa cggactcgac     180
aagggggagc ccgtcaacgc ggcggacgca gcggccctcg agcacgacaa ggcctacgac     240
cagcagctca aagcgggtga caatccgtac ctgaagtata accacgccga cgccgagttt     300
caggagcgtc tgaaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gcgcacagcc cgcgagaaag agactcaact ttgggcagac tggcgacaca     540
gagtcagtgc ccgaccctca accactcgga gaaccccccg cagcccctc tggtgtggga     600 tctaatacaa tggctgcagg cggtggcgct ccaatggcag acaataacga aggcgccgac     660
ggagtgggta gtgcctcagg aaattggcat tgcgattcca catggctggg cgacagagtc     720
atcaccacca gcacccgaac ctgggccctc cccacctaca acaaccacct ctacaagcaa     780
atctccaaca gcacttcggg aggaagcacc aacgacaaca cctacttcgg ctacagcacc     840
ccctgggggt attttgactt taacagattc cactgccact tctcaccacg tgactggcag     900
cgactcatca caacaactg gggattccgg cccaagaaac tcaacttcaa gctcttcaac     960
atccaggtca aggaggtcac gcagaatgaa ggcaccaaga ccatcgccaa taaccttacc    1020
agcacgattc aggtctttac ggactcggac taccagctcc cgtacgtcct cggctctgcg    1080
cacgagggct gcctgcctcc gttccggcg gacgtcttca tgattcctca gtacgggtac    1140
ctgactctga cgatggcag tcaggccgtg ggccgttcct ccttctactg cctggagtac    1200
tttccttctc aaatgctgag aacgggcaac aactttgagt tcagctacca gtttgaggac    1260
gtgccttttc acagcagcta cgcgcacagc caaagcctgg accggctgat gaaccccctc    1320
atcgaccagt acctgtactt cctgtctcgg actcagtcca cgggaggtac cgcaggaact    1380
cagcagttgc tattttctca ggccgggcct agcaacatgt cggctcaggc caaaaactgg    1440
ctacccgggc cctgctaccg gcagcaacgc gtctccacgg taaccaacca aaataacaac    1500
agcaactttg cctggaccgg tgccaccaag tatcatctga atggcagaga ctctctggta    1560
aatcccggta tcgctatggc aagccacaag gaaggagaag agcgattttt tccgtccagc    1620
ggaatcttaa ttttttgggaa acagggagct ggaagagaca cgtggacta tagcaaagtt    1680 atgctaacca gtgaggaaga aattaaaacc accaacccag tggccacaga agaatacggc    1740
caagtggccg ataacctgca aagtgccaac acggctccta ttgtagggac tgtcaacagt    1800
caaggagcct tacctggcat ggtctggcag aaccgggacg tgtacctgca gggtcctatc    1860
tgggccaaga ttcctcacac ggacggaaac tttcatccct cgccgctgat gggaggcttt    1920
ggactgaaac acccgcctcc tcagatcctg attaagaata cacctgttcc cgcggatcct    1980
ccaactacct tcagtcaagc taagctggcg tcgttcatca cgcagtacag caccggacag    2040
gtcagcgtgg aaattgaatg gggagctgcag aaagaaaaca gcaaacgctg gaacccagag    2100
attcaataca cttccaacta ctacaaatct acaaatgtgg actttgctgt taacacagaa    2160
ggcacttatt ctgagcctcg ccccatcggc acccgtttcc tcacccgtaa tctgtaa     2217
```

```
<210> SEQ ID NO 6
<211> LENGTH: 738
<212> TYPE: PRT
<213> ORGANISM: Artificial Sequence
<220> FEATURE:
<223> OTHER INFORMATION: Synthetic

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln Lys Gln Asp Asn Ala Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Arg Lys Arg Leu Asn Phe Gly Gln
                165                 170                 175

Thr Gly Asp Thr Glu Ser Val Pro Asp Pro Gln Pro Leu Gly Glu Pro
                180                 185                 190

Pro Ala Ala Pro Ser Gly Val Gly Ser Asn Thr Met Ala Ala Gly Gly
            195                 200                 205

Gly Ala Pro Met Ala Asp Asn Asn Glu Gly Ala Asp Gly Val Gly Ser
        210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Ser Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
            290                 295                 300

Asn Asn Trp Gly Phe Arg Pro Lys Lys Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Asp Tyr Gln
            340                 345                 350

Leu Pro Tyr Val Leu Gly Ser Ala His Glu Gly Cys Leu Pro Pro Phe
            355                 360                 365
```

-continued

```
Pro Ala Asp Val Phe Met Ile Pro Gln Tyr Gly Tyr Leu Thr Leu Asn
    370             375             380

Asp Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Glu Phe Ser Tyr
            405             410             415

Gln Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Phe Leu
            435             440             445

Ser Arg Thr Gln Ser Thr Gly Gly Thr Ala Gly Thr Gln Gln Leu Leu
    450             455             460

Phe Ser Gln Ala Gly Pro Ser Asn Met Ser Ala Gln Ala Lys Asn Trp
465             470             475             480

Leu Pro Gly Pro Cys Tyr Arg Gln Gln Arg Val Ser Thr Val Thr Asn
            485             490             495

Gln Asn Asn Asn Ser Asn Phe Ala Trp Thr Gly Ala Thr Lys Tyr His
            500             505             510

Leu Asn Gly Arg Asp Ser Leu Val Asn Pro Gly Ile Ala Met Ala Ser
            515             520             525

His Lys Glu Gly Glu Glu Arg Phe Phe Pro Ser Ser Gly Ile Leu Ile
    530             535             540

Phe Gly Lys Gln Gly Ala Gly Arg Asp Asn Val Asp Tyr Ser Lys Val
545             550             555             560

Met Leu Thr Ser Glu Glu Glu Ile Lys Thr Thr Asn Pro Val Ala Thr
            565             570             575

Glu Glu Tyr Gly Gln Val Ala Asp Asn Leu Gln Ser Ala Asn Thr Ala
            580             585             590

Pro Ile Val Gly Thr Val Asn Ser Gln Gly Ala Leu Pro Gly Met Val
            595             600             605

Trp Gln Asn Arg Asp Val Tyr Leu Gln Gly Pro Ile Trp Ala Lys Ile
    610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
            645             650             655

Pro Ala Asp Pro Pro Thr Thr Phe Ser Gln Ala Lys Leu Ala Ser Phe
            660             665             670

Ile Thr Gln Tyr Ser Thr Gly Gln Val Ser Val Glu Ile Glu Trp Glu
            675             680             685

Leu Gln Lys Glu Asn Ser Lys Arg Trp Asn Pro Glu Ile Gln Tyr Thr
    690             695             700

Ser Asn Tyr Tyr Lys Ser Thr Asn Val Asp Phe Ala Val Asn Thr Glu
705             710             715             720

Gly Thr Tyr Ser Glu Pro Arg Pro Ile Gly Thr Arg Phe Leu Thr Arg
            725             730             735

Asn Leu
```

<210> SEQ ID NO 7
<211> LENGTH: 738
<212> TYPE: PRT
<213> ORGANISM: Artificial Sequence
<220> FEATURE:
<223> OTHER INFORMATION: Synthetic -continued

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
```

-continued

```
                 405                 410                 415

Thr Phe Glu Asp Val Pro Phe His Ser Ser Tyr Ala His Ser Gln Ser
             420                 425                 430

Leu Asp Arg Leu Met Asn Pro Leu Ile Asp Gln Tyr Leu Tyr Tyr Leu
         435                 440                 445

Ser Arg Thr Gln Thr Thr Gly Gly Thr Ala Asn Thr Gln Thr Leu Gly
     450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
             485                 490                 495

Gln Asn Asn Asn Ser Asn Phe Ala Trp Thr Ala Gly Thr Lys Tyr His
             500                 505                 510

Leu Asn Gly Arg Asn Ser Leu Ala Asn Pro Gly Ile Ala Met Ala Thr
         515                 520                 525

His Lys Asp Asp Glu Glu Arg Phe Phe Pro Ser Asn Gly Ile Leu Ile
     530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
             565                 570                 575

Glu Glu Tyr Gly Ile Val Ala Asp Asn Leu Gln Gln Gln Asn Thr Ala
             580                 585                 590

Pro Gln Ile Gly Thr Val Asn Ser Gln Gly Ala Leu Pro Gly Met Val
         595                 600                 605

Trp Gln Asn Arg Asp Val Tyr Leu Gln Gly Pro Ile Trp Ala Lys Ile
     610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
             645                 650                 655

Pro Ala Asp Pro Pro Thr Thr Phe Asn Gln Ser Lys Leu Asn Ser Phe
         660                 665                 670

Ile Thr Gln Tyr Ser Thr Gly Gln Val Ser Val Glu Ile Glu Trp Glu
     675                 680                 685

Leu Gln Lys Glu Asn Ser Lys Arg Trp Asn Pro Glu Ile Gln Tyr Thr
     690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
             725                 730                 735

Asn Leu

<210> SEQ ID NO 8
<211> LENGTH: 736
<212> TYPE: PRT
<213> ORGANISM: Artificial Sequence
<220> FEATURE:
<223> OTHER INFORMATION: Synthetic

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
             20                  25                  30
```

```
Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
                115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
        435                 440                 445
```

-continued

```
Lys Thr Ile Asn Gly Ser Gly Gln Asn Gln Gln Thr Leu Lys Phe Ser
    450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
            515             520             525

Glu Gly Glu Asp Arg Phe Phe Pro Leu Ser Gly Ser Leu Ile Phe Gly
    530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Ala Gln Ala Gln
            580             585             590

Thr Gly Trp Val Gln Asn Gln Gly Ile Leu Pro Gly Met Val Trp Gln
    595             600             605

Asp Arg Asp Val Tyr Leu Gln Gly Pro Ile Trp Ala Lys Ile Pro His
    610             615             620

Thr Asp Gly Asn Phe His Pro Ser Pro Leu Met Gly Gly Phe Gly Met
625             630             635             640

Lys His Pro Pro Pro Gln Ile Leu Ile Lys Asn Thr Pro Val Pro Ala
            645             650             655

Asp Pro Pro Thr Ala Phe Asn Lys Asp Lys Leu Asn Ser Phe Ile Thr
            660             665             670

Gln Tyr Ser Thr Gly Gln Val Ser Val Glu Ile Glu Trp Glu Leu Gln
            675             680             685

Lys Glu Asn Ser Lys Arg Trp Asn Pro Glu Ile Gln Tyr Thr Ser Asn
    690             695             700

Tyr Tyr Lys Ser Asn Asn Val Glu Phe Ala Val Asn Thr Glu Gly Val
705             710             715             720

Tyr Ser Glu Pro Arg Pro Ile Gly Thr Arg Tyr Leu Thr Arg Asn Leu
            725             730             735
```

```
<210> SEQ ID NO 9
<211> LENGTH: 738
<212> TYPE: PRT
<213> ORGANISM: Artificial Sequence
<220> FEATURE:
<223> OTHER INFORMATION: Synthetic

<400> SEQUENCE: 9
```

```
Met Ala Ala Asp Gly Tyr Leu Pro Asp Trp Leu Glu Asp Asn Leu Ser
1               5               10              15

Glu Gly Ile Arg Glu Trp Trp Asp Leu Lys Pro Gly Ala Pro Lys Pro
            20              25              30

Lys Ala Asn Gln Gln Lys Gln Asp Asp Gly Arg Gly Leu Val Leu Pro
            35              40              45

Gly Tyr Lys Tyr Leu Gly Pro Phe Asn Gly Leu Asp Lys Gly Glu Pro
    50              55              60

Val Asn Ala Ala Asp Ala Ala Ala Leu Glu His Asp Lys Ala Tyr Asp
65              70              75              80
```

-continued

```
Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
```

-continued

```
                500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

```
<210> SEQ ID NO 10
<211> LENGTH: 738
<212> TYPE: PRT
<213> ORGANISM: Artificial Sequence
<220> FEATURE:
<223> OTHER INFORMATION: Synthetic

<400> SEQUENCE: 10
```

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
        115                 120                 125
```

-continued

```
Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
    530                 535                 540
```

```
Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Thr Lys Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 11
<211> LENGTH: 738
<212> TYPE: PRT
<213> ORGANISM: Artificial Sequence
<220> FEATURE:
<223> OTHER INFORMATION: Synthetic

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
                50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Pro Ser Pro Gln Arg Ser Pro Asp Ser Ser Ala Gly Ile
145                 150                 155                 160

Gly Lys Ser Gly Ser Gln Pro Ala Lys Lys Arg Leu Asn Phe Gly Gln
```

-continued

```
                    165               170               175
Thr Gly Asp Thr Glu Ser Val Pro Asp Pro Gln Pro Ile Gly Glu Pro
            180               185               190

Pro Ala Ala Pro Ser Gly Val Gly Pro Asn Thr Met Ala Ala Gly Gly
            195               200               205

Gly Ala Pro Met Ala Asp Asn Asn Glu Gly Ala Asp Gly Val Gly Ser
        210               215               220

Ser Ser Gly Asn Trp His Cys Asp Ser Thr Trp Leu Gly Asp Arg Val
    225               230               235               240

Ile Thr Thr Ser Thr Arg Thr Trp Ala Leu Pro Thr Tyr Asn Asn His
                245               250               255

Leu Tyr Lys Gln Ile Ser Asn Gly Thr Ser Gly Gly Ala Thr Asn Asp
            260               265               270

Asn Thr Tyr Phe Gly Tyr Ser Thr Pro Trp Gly Tyr Phe Asp Phe Asn
            275               280               285

Arg Phe His Cys His Phe Ser Pro Arg Asp Trp Gln Arg Leu Ile Asn
        290               295               300

Asn Asn Trp Gly Phe Arg Pro Lys Arg Leu Ser Phe Lys Leu Phe Asn
    305               310               315               320

Ile Gln Val Lys Glu Val Thr Gln Asn Glu Gly Thr Lys Thr Ile Ala
                325               330               335

Asn Asn Leu Thr Ser Thr Ile Gln Val Phe Thr Asp Ser Glu Tyr Gln
            340               345               350

Leu Pro Tyr Val Leu Gly Ser Ala His Gln Gly Cys Leu Pro Pro Phe
            355               360               365

Pro Ala Asp Val Phe Met Ile Pro Gln Tyr Gly Tyr Leu Thr Leu Asn
        370               375               380

Asn Gly Ser Gln Ala Val Gly Arg Ser Ser Phe Tyr Cys Leu Glu Tyr
    385               390               395               400

Phe Pro Ser Gln Met Leu Arg Thr Gly Asn Asn Phe Gln Phe Thr Tyr
                405               410               415

Gln Phe Glu Asp Val Pro Phe His Ser Ser Tyr Ala His Ser Gln Ser
            420               425               430

Leu Asp Arg Leu Met Asn Pro Leu Ile Asp Gln Tyr Leu Tyr Phe Leu
            435               440               445

Ser Arg Thr Gln Thr Thr Gly Gly Thr Ala Asn Thr Gln Gln Leu Leu
        450               455               460

Phe Ser Gln Gly Gly Pro Asn Thr Met Ala Asn Gln Ala Lys Asn Trp
    465               470               475               480

Leu Pro Gly Pro Cys Tyr Arg Gln Gln Arg Val Ser Thr Val Thr Gly
            485               490               495

Gln Asn Asn Asn Ser Asn Phe Ala Trp Thr Ala Gly Thr Lys Tyr His
            500               505               510

Leu Asn Gly Arg Asn Ser Leu Ala Asn Pro Gly Ile Ala Met Ala Thr
        515               520               525

His Lys Asp Asp Glu Glu Arg Phe Phe Pro Ser Asn Gly Ile Leu Ile
        530               535               540

Phe Gly Lys Gln Asn Ala Ala Arg Asp Asn Ala Asp Tyr Ser Lys Val
    545               550               555               560

Met Leu Thr Ser Glu Glu Glu Ile Lys Thr Thr Asn Pro Val Ala Thr
                565               570               575

Glu Glu Tyr Gly Ile Val Ala Asp Asn Leu Gln Gln Gln Asn Ala Ala
            580               585               590
```

-continued

```
Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Phe Leu Thr Arg
                725                 730                 735

Asn Leu

<210> SEQ ID NO 12
<211> LENGTH: 738
<212> TYPE: PRT
<213> ORGANISM: Artificial Sequence
<220> FEATURE:
<223> OTHER INFORMATION: Synthetic

<400> SEQUENCE: 12

Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Asn Thr Met Ala Ala Gly Gly
        195                 200                 205
```

-continued

```
Gly Ala Pro Met Ala Asp Asn Asn Glu Gly Ala Asp Gly Val Gly Ser
210             215                 220

Ala Ser Gly Asn Trp His Cys Asp Ser Thr Trp Leu Gly Asp Arg Val
225             230                 235                 240

Ile Thr Thr Ser Thr Arg Thr Trp Ala Leu Pro Thr Tyr Asn Asn His
                245                 250                 255

Leu Tyr Lys Gln Ile Ser Asn Ser Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
        290                 295                 300

Asn Asn Trp Gly Phe Arg Pro Lys Lys Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Asp Tyr Gln
                340                 345                 350

Leu Pro Tyr Val Leu Gly Ser Ala His Glu Gly Cys Leu Pro Pro Phe
                355                 360                 365

Pro Ala Asp Val Phe Met Ile Pro Gln Tyr Gly Tyr Leu Thr Leu Asn
        370                 375                 380

Asp Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Phe Leu
                435                 440                 445

Ser Arg Thr Gln Ser Thr Gly Gly Thr Ala Gly Thr Gln Gln Leu Leu
        450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Val Thr Asn
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Ile Ala Met Ala Ser
        515                 520                 525

His Lys Glu Gly Glu Glu Arg Phe Phe Pro Ser Ser Gly Ile Leu Ile
        530                 535                 540

Phe Gly Lys Gln Gly Ala Gly Arg Asp Asn Val Asp Tyr Ser Lys Val
545                 550                 555                 560

Met Leu Thr Ser Glu Glu Glu Ile Lys Thr Thr Asn Pro Val Ala Thr
                565                 570                 575

Glu Gln Tyr Gly Gln Val Ala Asp Asn Leu Gln Gln Gln Asn Ala Ala
                580                 585                 590

Pro Ile Val Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
```

```
625                 630                 635                 640

Gly Leu Lys His Pro Pro Pro Gln Ile Leu Ile Lys Asn Thr Pro Val
                645             650             655

Pro Ala Asp Pro Pro Thr Thr Phe Ser Gln Ala Lys Leu Ala Ser Phe
                660             665             670

Ile Thr Gln Tyr Ser Thr Gly Gln Val Ser Val Glu Ile Glu Trp Glu
            675             680             685

Leu Gln Lys Glu Asn Ser Lys Arg Trp Asn Pro Glu Ile Gln Tyr Thr
        690             695             700

Ser Asn Tyr Tyr Lys Ser Thr Asn Val Asp Phe Ala Val Asn Thr Glu
705             710             715             720

Gly Thr Tyr Ser Glu Pro Arg Pro Ile Gly Thr Arg Phe Leu Thr Arg
                725             730             735

Asn Leu
```

```
<210> SEQ ID NO 13
<211> LENGTH: 738
<212> TYPE: PRT
<213> ORGANISM: Artificial Sequence
<220> FEATURE:
<223> OTHER INFORMATION: Synthetic

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln Lys Gln Asp Asn Ala Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100             105             110

Asn Leu Gly Arg Ala Val Phe Gln Ala Lys Lys Arg Val Leu Glu Pro
            115             120             125

Leu Gly Leu Val Glu Glu Gly Ala Lys Thr Ala Pro Gly Lys Lys Arg
        130             135             140

Pro Val Glu Pro Ser Pro Gln Arg Ser Pro Asp Ser Ser Ala Gly Ile
145             150             155             160

Gly Lys Ser Gly Ala Gln Pro Ala Arg Lys Arg Leu Asn Phe Gly Gln
                165             170             175

Thr Gly Asp Thr Glu Ser Val Pro Asp Pro Gln Pro Leu Gly Glu Pro
            180             185             190

Pro Ala Ala Pro Ser Gly Val Gly Ser Asn Thr Met Ala Ala Gly Gly
            195             200             205

Gly Ala Pro Met Ala Asp Asn Asn Glu Gly Ala Asp Gly Val Gly Ser
        210             215             220

Ala Ser Gly Asn Trp His Cys Asp Ser Thr Trp Leu Gly Asp Arg Val
225             230             235             240

Ile Thr Thr Ser Thr Arg Thr Trp Ala Leu Pro Thr Tyr Asn Asn His
                245             250             255
```

-continued

```
Leu Tyr Lys Gln Ile Ser Asn Ser Thr Ser Gly Gly Ser Thr Asn Asp
        260             265             270

Asn Thr Tyr Phe Gly Tyr Ser Thr Pro Trp Gly Tyr Phe Asp Phe Asn
        275             280             285

Arg Phe His Cys His Phe Ser Pro Arg Asp Trp Gln Arg Leu Ile Asn
        290             295             300

Asn Asn Trp Gly Phe Arg Pro Lys Lys Leu Asn Phe Lys Leu Phe Asn
305             310             315             320

Ile Gln Val Lys Glu Val Thr Gln Asn Glu Gly Thr Lys Thr Ile Ala
            325             330             335

Asn Asn Leu Thr Ser Thr Ile Gln Val Phe Thr Asp Ser Asp Tyr Gln
            340             345             350

Leu Pro Tyr Val Leu Gly Ser Ala His Glu Gly Cys Leu Pro Pro Phe
            355             360             365

Pro Ala Asp Val Phe Met Ile Pro Gln Tyr Gly Tyr Leu Thr Leu Asn
            370             375             380

Asp Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Glu Phe Ser Tyr
                405             410             415

Gln Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Phe Leu
            435             440             445

Ser Arg Thr Gln Ser Thr Gly Gly Thr Ala Gly Thr Gln Gln Leu Leu
        450             455             460

Phe Ser Gln Ala Gly Pro Ser Asn Met Ser Ala Gln Ala Lys Asn Trp
465             470             475             480

Leu Pro Gly Pro Cys Tyr Arg Gln Gln Arg Val Ser Thr Val Thr Asn
                485             490             495

Gln Asn Asn Asn Ser Asn Phe Ala Trp Thr Gly Ala Thr Lys Tyr His
            500             505             510

Leu Asn Gly Arg Asp Ser Leu Val Asn Pro Gly Ile Ala Met Ala Ser
            515             520             525

His Lys Glu Gly Glu Glu Arg Phe Phe Pro Ser Ser Gly Ile Leu Ile
            530             535             540

Phe Gly Lys Gln Gly Ala Gly Arg Asp Asn Val Asp Tyr Ser Lys Val
545             550             555             560

Met Leu Thr Ser Glu Glu Glu Ile Lys Thr Thr Asn Pro Val Ala Thr
                565             570             575

Glu Glu Tyr Gly Gln Val Ala Asp Asn Leu Gln Ser Ala Asn Thr Ala
            580             585             590

Pro Ile Val Gly Thr Val Asn Ser Gln Gly Ala Leu Pro Gly Met Val
            595             600             605

Trp Gln Asn Arg Asp Val Tyr Leu Gln Gly Pro Ile Trp Ala Lys Ile
        610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
                645             650             655

Pro Ala Asp Pro Pro Thr Thr Phe Ser Gln Ala Lys Leu Ala Ser Phe
            660             665             670
```

```
Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Phe Leu Thr Arg
                725                 730                 735

Asn Leu

<210> SEQ ID NO 14
<211> LENGTH: 2217
<212> TYPE: DNA
<213> ORGANISM: Artificial Sequence
<220> FEATURE:
<223> OTHER INFORMATION: Synthetic

<400> SEQUENCE: 14
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga accggtaga gccatcaccc cagcgttctc cagactcctc tgcgggcatc     480
ggcaagtcgg gctcacagcc cgccaaaaaa agactcaatt ttggtcagac tggcgacaca     540
gagtcagttc cagaccctca acctatcgga gaacctccag cagcgccctc tggtgtggga     600
cctaatacaa tggctgcagg cggtggcgca ccaatggcag acaataacga aggcgccgac     660
ggagtgggta gttcctcggg aaattggcat tgcgattcca catggctggg cgacagagtc     720
atcaccacca gcacccgaac ctgggccctg cccacctaca acaaccacct ctacaagcaa     780
atctccaacg gacatcgggg aggagccacc aacgacaaca cctacttcgg ctacagcacc     840
ccctgggggt attttgactt taacagattc cactgccact tttcaccacg tgactggcag     900
cgactcatca acaacaactg gggattccgg cccaagagac tcagcttcaa gctcttcaac     960
atccaggtca aggaggtcac gcagaatgaa ggcaccaaga ccatcgccaa taacctcacc     1020
agcaccatcc aggtgtttac ggactcggag taccagctgc cgtacgttct cggctctgcc     1080
caccagggct gcctgcctcc gttcccggcg gacgtgttca tgattcccca gtacggctac     1140
ctaacactca caacggtag tcaggccgtg ggacgctcct ccttctactg cctggaatac     1200
tttccttcgc agatgctgag aaccggcaac aacttccagt ttacttacca gttcgaggac     1260
gtgcctttcc acagcagcta cgcccacagc cagagcttgg accggctgat gaatcctctg     1320
attgaccagt acctgtactt cttgtctcgg actcaaacaa caggaggcac ggcaaatacg     1380
cagcagctgc tattcagcca aggtgggcct aatacaatgg ccaatcaggc aaagaactgg     1440
ctgccaggac cctgttaccg ccaacaacgc gtctcaacgg taaccgggca aaacaacatc     1500
agcaactttg cctggactgc tgggaccaaa taccatctga atggaagaaa ttcattggct     1560
aatcctggac tcgctatggc aacacacaaa gacgacgagg agcgtttttt tcccagtaac     1620
gggatcctga tttttggcaa acaaaatgct gccagagaca atgcggatta cagcaaagtc     1680
```

-continued

```
atgctcacca gcgaggaaga aatcaaaacc actaaccctg tggctacaga ggaatacggt      1740
atcgtggcag ataacttgca gcagcaaaac gccgctcctc aaattggaac tgtcaacagc      1800
cagggggcct tacccggtat ggtctggcag aaccgggacg tgtacctgca gggtcccatc      1860
tgggccaaga ttcctcacac ggacggcaac ttccacccgt ctccgctgat gggcggcttt      1920
ggcctgaaac atcctccgcc tcagatcctg atcaagaaca cgcctgtacc tgcggatcct      1980
ccgaccacct caaccagtc aaagctgaac tctttcatca cgcaatacag caccggacag       2040
gtcagcgtgg aaattgaatg ggagctgcag aaggaaaaca gcaagcgctg gaaccccgag      2100
atccagtaca cctccaacta ctacaaatct acaagtgtgg actttgctgt taatacagaa      2160
ggcgtgtact ctgaaccccg ccccattggc acccgtttcc tcacccgtaa tctgtaa        2217
```

<210> SEQ ID NO 15
<211> LENGTH: 738
<212> TYPE: PRT
<213> ORGANISM: Artificial Sequence
<220> FEATURE:
<223> OTHER INFORMATION: Synthetic

<400> SEQUENCE: 15

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ser Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270
```

-continued

```
Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Phe Leu
            435                 440                 445

Ser Arg Thr Gln Thr Thr Gly Gly Thr Ala Asn Thr Gln Gln Leu Leu
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Val Thr Gly
                485                 490                 495

Gln Asn Asn Ile Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Lys Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Ala Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685
```

-continued

```
Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Phe Leu Thr Arg
                725                 730                 735

Asn Leu
```

```
<210> SEQ ID NO 16
<211> LENGTH: 2217
<212> TYPE: DNA
<213> ORGANISM: Artificial Sequence
<220> FEATURE:
<223> OTHER INFORMATION: Synthetic

<400> SEQUENCE: 16
atggctgccg atggttatct tccagattgg ctcgaggaca acctctctga gggcattcgc      60
gagtggtggg acttgaaacc tggagccccg aaacccaaag ccaaccagca aaagcaggac     120
aacggccggg gtctggtgct tcctggctac aagtacctcg gacccttcaa cggactcgac     180 aaggggggagc ccgtcaacgc ggcggacgca gcggccctcg agcacgacaa ggcctacgac     240
cagcagctca aagcgggtga caatccgtac ctgaagtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gcgcacagcc cgcgaaaaag agactcaact ttgggcagac tggcgactca     540
gagtcagtgc ccgaccctca accaatcgga gaacccccg caggcccctc tggtctggga     600
tctaatacaa tggctgcagg cggtggcgct ccaatggcag acaataacga aggcgccgac     660
ggagtgggta gtgcctcagg aaattggcat tgcgattcca catggctggg cgacagagtc     720
atcaccacca gcacccgaac ctgggccctc cccacctaca caaccacct ctacaagcaa      780 atctccaaca gcacttcggg aggaagcacc aacgacaaca cctacttcgg ctacagcacc     840
ccctgggggt attttgactt taacagattc cactgccact ctcaccacg tgactggcag      900 cgactcatca caacaactg gggattccgg cccaagaaac tcaacttcaa gctcttcaac      960
atccaggtca aggaggtcac gcagaatgaa ggcaccaaga ccatcgccaa taaccttacc    1020
agcacgattc aggtctttac ggactcggac taccagctcc cgtacgtcct cggctctgcg    1080
cacgagggct gcctgcctcc gttcccgggcg gacgtcttca tgattcctca gtacgggtac    1140
ctgactctga cgatggcag tcaggccgtg ggccgttcct ccttctactg cctggagtac    1200
tttccttctc aaatgctgag aacgggcaac aactttgagt tcagctacca gtttgaggac    1260 gtgcctttc acagcagcta cgcgcacagc caaagcctgg accggctgat gaacccctc     1320 atcgaccagt acctgtactt cctgtctcgg actcagtcca cgggaggtac cgcaggaact    1380
cagcagttgc tattttctca ggccgggcct agcaacatgt cggctcaggc caaaaactgg    1440
ctacccgggc cctgctaccg gcagcaacgc gtctccacgg taaccaacca aaataacatc    1500
agcaactttg cctggaccgg tgccaccaag tatcatctga tggcagaga ctctctggta    1560 aatcccggta tcgctatggc aagccacaag gaaggagaag agcgattttt tccgtccagc    1620
ggaatcttaa ttttgggaa acagggagct ggaagagaca cgtggacta tagcaaagtt     1680 atgctaacca gtgaggaaga aattaaaacc accaacccag tggccacaga acagtacggc    1740
```

```
caagtggccg ataacctgca acagcaaaac gccgctccta ttgtagggac tgtcaacagt   1800
caaggagcct tacctggcat ggtctggcag aaccgggacg tgtacctgca gggtcctatc   1860
tgggccaaga ttcctcacac ggacggaaac tttcatccct cgccgctgat gggaggcttt   1920
ggactgaaac acccgcctcc tcagatcctg attaagaata cacctgttcc cgcggatcct   1980
ccaactacct tcagtcaagc taagctggcg tcgttcatca cgcagtacag caccggacag   2040
gtcagcgtgg aaattgaatg ggagctgcag aaagaaaaca gcaaacgctg gaacccagag   2100
attcaataca cttccaacta ctacaaatct acaaatgtgg actttgctgt taacacagaa   2160
ggcacttatt ctgagcctcg ccccatcggc accgtttcc tcacccgtaa tctgtaa      2217
```

```
<210> SEQ ID NO 17
<211> LENGTH: 738
<212> TYPE: PRT
<213> ORGANISM: Artificial Sequence
<220> FEATURE:
<223> OTHER INFORMATION: Synthetic

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Ser Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285
```

-continued

```
Arg Phe His Cys His Phe Ser Pro Arg Asp Trp Gln Arg Leu Ile Asn
    290                 295                 300

Asn Asn Trp Gly Phe Arg Pro Lys Lys Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Asp Tyr Gln
            340                 345                 350

Leu Pro Tyr Val Leu Gly Ser Ala His Glu Gly Cys Leu Pro Pro Phe
            355                 360                 365

Pro Ala Asp Val Phe Met Ile Pro Gln Tyr Gly Tyr Leu Thr Leu Asn
    370                 375                 380

Asp Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Phe Leu
            435                 440                 445

Ser Arg Thr Gln Ser Thr Gly Gly Thr Ala Gly Thr Gln Gln Leu Leu
    450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Val Thr Asn
                485                 490                 495

Gln Asn Asn Ile Ser Asn Phe Ala Trp Thr Gly Ala Thr Lys Tyr His
                500                 505                 510

Leu Asn Gly Arg Asp Ser Leu Val Asn Pro Gly Ile Ala Met Ala Ser
            515                 520                 525

His Lys Glu Gly Glu Glu Arg Phe Phe Pro Ser Ser Gly Ile Leu Ile
    530                 535                 540

Phe Gly Lys Gln Gly Ala Gly Arg Asp Asn Val Asp Tyr Ser Lys Val
545                 550                 555                 560

Met Leu Thr Ser Glu Glu Glu Ile Lys Thr Thr Asn Pro Val Ala Thr
                565                 570                 575

Glu Gln Tyr Gly Gln Val Ala Asp Asn Leu Gln Gln Gln Asn Ala Ala
            580                 585                 590

Pro Ile Val Gly Thr Val Asn Ser Gln Gly Ala Leu Pro Gly Met Val
    595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700
```

-continued

```
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Phe Leu Thr Arg
                725                 730                 735

Asn Leu
```

```
<210> SEQ ID NO 18
<211> LENGTH: 2217
<212> TYPE: DNA
<213> ORGANISM: Artificial Sequence
<220> FEATURE:
<223> OTHER INFORMATION: Synthetic

<400> SEQUENCE: 18
atggctgccg atggttatct tccagattgg ctcgaggaca acctctctga gggcattcgc      60
gagtggtggg ctttgaaacc tggagccccg caacccaaag ccaaccagca aaagcaggac     120
aacgctcggg gtctggtgct tcctggctac aagtacctcg gacccttcaa cggactcgac     180 aaggggagc ccgtcaacgc ggcggacgca gcggccctcg agcacgacaa ggcctacgac      240
cagcagctca aagcgggtga caatccgtac ctgaagtata accacgccga cgccgagttt     300
caggagcgtc tgaaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gcgcacagcc cgcgagaaag agactcaact ttgggcagac tggcgacaca     540
gagtcagtgc ccgaccctca accactcgga gaacccccg cagcccctc tggtgtggga       600 tctaatacaa tggctgcagg cggtggcgct ccaatggcag acaataacga aggcgccgac     660
ggagtgggta gtgcctcagg aaattggcat tgcgattcca catggctggg cgacagagtc     720
atcaccacca gcacccgaac ctgggccctc cccacctaca caaccacct ctacaagcaa      780 atctccaaca gcacttcggg aggaagcacc aacgacaaca cctacttcgg ctacagcacc     840 ccctggggt attttgactt taacagattc cactgccact tctcaccacg tgactggcag      900
cgactcatca caacaactg gggattccgg cccaagaaac tcaacttcaa gctcttcaac      960
atccaggtca aggaggtcac gcagaatgaa ggcaccaaga ccatcgccaa taaccttacc    1020
agcacgattc aggtctttac ggactcggac taccagctcc cgtacgtcct cggctctgcg    1080
cacgagggct gcctgcctcc gttcccggcg gacgtcttca tgattcctca gtacgggtac    1140
ctgactctga cgatggcag tcaggccgtg ggccgttcct ccttctactg cctggagtac    1200
tttccttctc aaatgctgag aacgggcaac aactttgagt tcagctacca gtttgaggac    1260 gtgcctttc acagcagcta cgcgcacagc caaagcctgg accggctgat gaaccccctc    1320
atcgaccagt acctgtactt cctgtctcgg actcagtcca cgggaggtac cgcaggaact    1380
cagcagttgc tattttctca ggccgggcct agcaacatgt cggctcaggc caaaaactgg    1440
ctacccgggc cctgctaccg gcagcaacgc gtctccacgg taaccaacca aaataacatc    1500
agcaactttg cctggaccgg tgccaccaag tatcatctga tggcagaga ctctctggta     1560 aatcccggta tcgctatggc aagccacaag gaaggagaag agcgatttt tccgtccagc     1620 ggaatcttaa tttttgggaa acaggagct ggaagagaca acgtggacta tagcaaagtt    1680
atgctaacca gtgaggaaga aattaaaacc accaacccag tggccacaga agaatacggc    1740
caagtggccg ataacctgca aagtgccaac acggctccta ttgtagggac tgtcaacagt    1800
caaggagcct tacctggcat ggtctggcag aaccgggacg tgtacctgca gggtcctatc    1860
```

```
tgggccaaga ttcctcacac ggacggaaac tttcatccct cgccgctgat gggaggcttt    1920
ggactgaaac acccgcctcc tcagatcctg attaagaata cacctgttcc cgcggatcct    1980
ccaactacct tcagtcaagc taagctggcg tcgttcatca cgcagtacag caccggacag    2040
gtcagcgtgg aaattgaatg gggagctgcag aaagaaaaca gcaaacgctg gaacccagag    2100
attcaataca cttccaacta ctacaaatct acaaatgtgg actttgctgt taacacagaa    2160
ggcacttatt ctgagcctcg ccccatcggc acccgtttcc tcacccgtaa tctgtaa       2217
```

```
<210> SEQ ID NO 19
<211> LENGTH: 738
<212> TYPE: PRT
<213> ORGANISM: Artificial Sequence
<220> FEATURE:
<223> OTHER INFORMATION: Synthetic

<400> SEQUENCE: 19

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Arg Lys Arg Leu Asn Phe Gly Gln
                165                 170                 175

Thr Gly Asp Thr Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Ser Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300
```

-continued

```
Asn Asn Trp Gly Phe Arg Pro Lys Lys Leu Asn Phe Lys Leu Phe Asn
305                 310             315             320

Ile Gln Val Lys Glu Val Thr Gln Asn Glu Gly Thr Lys Thr Ile Ala
                325             330             335

Asn Asn Leu Thr Ser Thr Ile Gln Val Phe Thr Asp Ser Asp Tyr Gln
            340             345             350

Leu Pro Tyr Val Leu Gly Ser Ala His Glu Gly Cys Leu Pro Pro Phe
        355             360             365

Pro Ala Asp Val Phe Met Ile Pro Gln Tyr Gly Tyr Leu Thr Leu Asn
        370             375             380

Asp Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Glu Phe Ser Tyr
                405             410             415

Gln Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Phe Leu
            435             440             445

Ser Arg Thr Gln Ser Thr Gly Gly Thr Ala Gly Thr Gln Gln Leu Leu
        450             455             460

Phe Ser Gln Ala Gly Pro Ser Asn Met Ser Ala Gln Ala Lys Asn Trp
465             470             475             480

Leu Pro Gly Pro Cys Tyr Arg Gln Gln Arg Val Ser Thr Val Thr Asn
                485             490             495

Gln Asn Asn Ile Ser Asn Phe Ala Trp Thr Gly Ala Thr Lys Tyr His
            500             505             510

Leu Asn Gly Arg Asp Ser Leu Val Asn Pro Gly Ile Ala Met Ala Ser
            515             520             525

His Lys Glu Gly Glu Glu Arg Phe Phe Pro Ser Ser Gly Ile Leu Ile
        530             535             540

Phe Gly Lys Gln Gly Ala Gly Arg Asp Asn Val Asp Tyr Ser Lys Val
545             550             555             560

Met Leu Thr Ser Glu Glu Glu Ile Lys Thr Thr Asn Pro Val Ala Thr
                565             570             575

Glu Glu Tyr Gly Gln Val Ala Asp Asn Leu Gln Ser Ala Asn Thr Ala
            580             585             590

Pro Ile Val Gly Thr Val Asn Ser Gln Gly Ala Leu Pro Gly Met Val
            595             600             605

Trp Gln Asn Arg Asp Val Tyr Leu Gln Gly Pro Ile Trp Ala Lys Ile
        610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
                645             650             655

Pro Ala Asp Pro Pro Thr Thr Phe Ser Gln Ala Lys Leu Ala Ser Phe
                660             665             670

Ile Thr Gln Tyr Ser Thr Gly Gln Val Ser Val Glu Ile Glu Trp Glu
            675             680             685

Leu Gln Lys Glu Asn Ser Lys Arg Trp Asn Pro Glu Ile Gln Tyr Thr
            690             695             700

Ser Asn Tyr Tyr Lys Ser Thr Asn Val Asp Phe Ala Val Asn Thr Glu
705             710             715             720
```

-continued

Gly Thr Tyr Ser Glu Pro Arg Pro Ile Gly Thr Arg Phe Leu Thr Arg
                725                 730                 735

Asn Leu

<210> SEQ ID NO 20
<211> LENGTH: 2214
<212> TYPE: DNA
<213> ORGANISM: Artificial Sequence
<220> FEATURE:
<223> OTHER INFORMATION: Synthetic

<400> SEQUENCE: 20
atggctgccg atggttatct tccagattgg ctcgaggaca acctctctga gggcattcgc        60
gagtggtggg cgctgaaacc tggagccccg aagcccaaag ccaaccagca aaagcaggac       120
gacggccggg gtctggtgct tcctggctac aagtacctcg accccttcaa cggactcgac       180
aagggggagc ccgtcaacgc ggcggacgca gcggccctcg agcacgacaa ggcctacgac       240
cagcagctgc aggcgggtga caatccgtac ctgcggtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaga gaccggtaga gccatcaccc cagcgttctc cagactcctc tgcgggcatc       480
ggcaagtcgg gctcacagcc cgccaaaaaa agactcaatt ttggtcagac tggcgacaca       540
gagtcagttc cagaccctca acctatcgga gaacctccag cagcgccctc tggtgtggga       600
cctaatacaa tggctgcagg cggtggcgca ccaatggcag acaataacga aggcgccgac       660
ggagtgggta gttcctcggg aaattggcat tgcgattcca catggctggg cgacagagtc       720
atcaccacca gcacccgaac ctgggccctg cccacctaca acaaccacct ctacaagcaa       780
atctcctcag catccacagg agccagtaac gacaaccatt acttcggcta cagcacccccc      840 tggggggtatt ttgactttaa cagattccac tgccactttt caccacgtga ctggcagcga       900
ctcatcaaca caaactgggg attccggccc aagagactca gcttcaagct cttcaacatc       960
caggtcaagg aggtcacgca gaatgaaggc accaagacca tcgccaataa cctcaccagc      1020
accatccagg tgtttacgga ctcggagtac cagctgccgt acgttctcgg ctctgcccac      1080
cagggctgcc tgcctccgtt cccggcggac gtgttcatga ttccccagta cggctaccta      1140
acactcaaca acggtagtca ggccgtggga cgctcctcct ctactgcct ggaatacttt       1200 ccttcgcaga tgctgagaac cggcaacaac ttccagtttta cttaccagtt cgaggacgtg      1260
cctttccaca gcagctacgc ccacagccag agcttggacc ggctgatgaa tcctctgatt      1320
gaccagtacc tgtacttctt gtctcggact caaacaacag gaggcacggc aaatacgcag      1380
cagctgctat tcagccaagg tgggcctaat acaatggcca tcaggcaaa gaactggctg       1440 ccaggaccct gttaccgcca acaacgcgtc tcaacggtaa ccgggcaaaa caacaatagc      1500
aactttgcct ggactgctgg gaccaaatac catctgaatg gaagaaattc attggctaat      1560
cctggcatcg ctatggcaac acacaaagac gacgaggagc gttttttttcc cagtaacggg      1620 atcctgattt ttggcaaaca aaatgctgcc agagacaatg cggattacag caaagtcatg      1680
ctcaccagcg aggaagaaat caaaaccact aaccctgtgg ctacagagga atacggtatc      1740
gtggcagata acttgcagca gcaaaacgcc gctcctcaaa ttggaactgt caacagccag      1800
ggggccttac ccggtatggt ctggcagaac cgggacgtgt acctgcaggg tcccatctgg      1860
gccaagattc ctcacacgga cggcaacttc caccccgtctc cgctgatggg cggctttggc      1920

-continued ctgaaacatc ctccgcctca gatcctgatc aagaacacgc ctgtacctgc ggatcctccg          1980
accaccttca accagtcaaa gctgaactct ttcatcacgc aatacagcac cggacaggtc          2040
agcgtggaaa ttgaatggga gctgcagaag gaaaacagca agcgctggaa ccccgagatc          2100
cagtacacct ccaactacta caaatctaca agtgtggact ttgctgttaa tacagaaggc          2160
gtgtactctg aaccccgccc cattggcacc cgtttcctca cccgtaatct gtaa               2214

<210> SEQ ID NO 21
<211> LENGTH: 737
<212> TYPE: PRT
<213> ORGANISM: Artificial Sequence
<220> FEATURE:
<223> OTHER INFORMATION: Synthetic

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Ala Gly Ile
145                 150                 155                 160

Gly Lys Ser Gly Ser Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Gln
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Phe Leu Ser
                435                 440                 445

Arg Thr Gln Thr Thr Gly Gly Thr Ala Asn Thr Gln Gln Leu Leu Phe
        450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Val Thr Gly Gln
                485                 490                 495

Asn Asn Asn Ser Asn Phe Ala Trp Thr Ala Gly Thr Lys Tyr His Leu
                500                 505                 510

Asn Gly Arg Asn Ser Leu Ala Asn Pro Gly Ile Ala Met Ala Thr His
                515                 520                 525

Lys Asp Asp Glu Glu Arg Phe Phe Pro Ser Asn Gly Ile Leu Ile Phe
        530                 535                 540

Gly Lys Gln Asn Ala Ala Arg Asp Asn Ala Asp Tyr Ser Lys Val Met
545                 550                 555                 560

Leu Thr Ser Glu Glu Glu Ile Lys Thr Thr Asn Pro Val Ala Thr Glu
                565                 570                 575

Glu Tyr Gly Ile Val Ala Asp Asn Leu Gln Gln Gln Asn Ala Ala Pro
                580                 585                 590

Gln Ile Gly Thr Val Asn Ser Gln Gly Ala Leu Pro Gly Met Val Trp
                595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
        690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Phe Leu Thr Arg Asn
                725                 730                 735

Leu

<210> SEQ ID NO 22
<211> LENGTH: 2214
<212> TYPE: DNA
<213> ORGANISM: Artificial Sequence
<220> FEATURE:
<223> OTHER INFORMATION: Synthetic

<400> SEQUENCE: 22
atggctgccg atggttatct tccagattgg ctcgaggaca acctctctga gggcattcgc        60
gagtggtggg acttgaaacc tggagccccg aaacccaaag ccaaccagca aaagcaggac       120
aacggccggg gtctggtgct tcctggctac aagtacctcg gacccttcaa cggactcgac       180 aaggggggagc ccgtcaacgc ggcggacgca gcggccctcg agcacgacaa ggcctacgac       240
cagcagctca aagcgggtga caatccgtac ctgaagtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaga gaccggtaga gccatcaccc cagcgttctc cagactcctc tgcgggcatc       480
ggcaagtcgg gcgcacagcc cgcgaaaaag agactcaact ttgggcagac tggcgactca       540
gagtcagtgc ccgaccctca accaatcgga gaacccccg caggcccctc tggtctggga       600
tctaatacaa tggctgcagg cggtggcgct ccaatggcag acaataacga aggcgccgac       660
ggagtgggta gtgcctcagg aaattggcat tgcgattcca catggctggg cgacagagtc       720
atcaccacca gcaccgaac ctgggccctc cccacctaca acaaccacct ctacaagcaa       780
atctcctcag catccacagg agccagtaac gacaaccatt acttcggcta cagcacccc        840 tggggggtatt ttgactttaa cagattccac tgccacttct caccacgtga ctggcagcga       900
ctcatcaaca caaactgggg attccggccc aagaaactca acttcaagct cttcaacatc       960
caggtcaagg aggtcacgca gaatgaaggc accaagacca cgccaataa ccttaccagc       1020 acgattcagg tctttacgga ctcggactac cagctcccgt acgtcctcgg ctctgcgcac       1080
gagggctgcc tgcctccgtt cccggcggac gtcttcatga ttcctcagta cgggtacctg       1140
actctgaacg atggcagtca ggccgtgggc cgttcctcct tctactgcct ggagtacttt       1200
ccttctcaaa tgctgagaac gggcaacaac tttgagttca gctaccagtt tgaggacgtg       1260 cctttttcaca gcagctacgc gcacagccaa agcctggacc ggctgatgaa ccccctcatc       1320
gaccagtacc tgtacttcct gtctcggact cagtccacgg gaggtaccgc aggaactcag       1380
cagttgctat tttctcaggc cgggcctagc aacatgtcgg ctcaggccaa aaactggcta       1440
cccgggccct gctaccggca gcaacgcgtc tccacggtaa ccaaccaaaa taacaatagc       1500
aactttgcct ggaccggtgc caccaagtat catctgaatg gcagagactc tctggtaaat       1560
cccggtatcg ctatggcaag ccacaaggaa ggagaagagc gattttttcc gtccagcgga       1620 atcttaatttt ttgggaaaca gggagctgga agagacaacg tggactatag caaagttatg       1680
ctaaccagtg aggaagaaat taaaaccacc aacccagtgg ccacagaaca gtacggccaa       1740
gtggccgata acctgcaaca gcaaaacgcc gctcctattg tagggactgt caacagtcaa       1800
ggagccttac ctggcatggt ctggcagaac cgggacgtgt acctgcaggg tcctatctgg       1860
gccaagattc tcacacggga cggaaacttt catccctcgc cgctgatggg aggctttgga       1920
ctgaaacacc cgcctcctca gatcctgatt aagaatacac tgttcccgc ggatcctcca       1980 actaccttca gtcaagctaa gctggcgtcg ttcatcacgc agtacagcac cggacaggtc       2040

```
agcgtggaaa ttgaatggga gctgcagaaa gaaaacagca aacgctggaa cccagagatt    2100
caatacactt ccaactacta caaatctaca aatgtggact ttgctgttaa cacagaaggc    2160
acttattctg agcctcgccc catcggcacc cgtttcctca cccgtaatct gtaa          2214
```

<210> SEQ ID NO 23
<211> LENGTH: 737
<212> TYPE: PRT
<213> ORGANISM: Artificial Sequence
<220> FEATURE:
<223> OTHER INFORMATION: Synthetic

<400> SEQUENCE: 23

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Gln Asn Glu Gly Thr Lys Thr Ile Ala Asn
                325                 330                 335
```

-continued

```
Asn Leu Thr Ser Thr Ile Gln Val Phe Thr Asp Ser Asp Tyr Gln Leu
        340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Gln
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Phe Leu Ser
        435                 440                 445

Arg Thr Gln Ser Thr Gly Gly Thr Ala Gly Thr Gln Gln Leu Leu Phe
        450                 455                 460

Ser Gln Ala Gly Pro Ser Asn Met Ser Ala Gln Ala Lys Asn Trp Leu
465                 470                 475                 480

Pro Gly Pro Cys Tyr Arg Gln Gln Arg Val Ser Thr Val Thr Asn Gln
                485                 490                 495

Asn Asn Asn Ser Asn Phe Ala Trp Thr Gly Ala Thr Lys Tyr His Leu
                500                 505                 510

Asn Gly Arg Asp Ser Leu Val Asn Pro Gly Ile Ala Met Ala Ser His
            515                 520                 525

Lys Glu Gly Glu Glu Arg Phe Phe Pro Ser Ser Gly Ile Leu Ile Phe
        530                 535                 540

Gly Lys Gln Gly Ala Gly Arg Asp Asn Val Asp Tyr Ser Lys Val Met
545                 550                 555                 560

Leu Thr Ser Glu Glu Glu Ile Lys Thr Thr Asn Pro Val Ala Thr Glu
                565                 570                 575

Gln Tyr Gly Gln Val Ala Asp Asn Leu Gln Gln Gln Asn Ala Ala Pro
            580                 585                 590

Ile Val Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Ser Gln Ala Lys Leu Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Tyr Lys Ser Thr Asn Val Asp Phe Ala Val Asn Thr Glu Gly
705                 710                 715                 720

Thr Tyr Ser Glu Pro Arg Pro Ile Gly Thr Arg Phe Leu Thr Arg Asn
                725                 730                 735

Leu
```

<210> SEQ ID NO 24
<211> LENGTH: 2214
<212> TYPE: DNA
<213> ORGANISM: Artificial Sequence
<220> FEATURE:
<223> OTHER INFORMATION: Synthetic

<400> SEQUENCE: 24
atggctgccg atggttatct tccagattgg ctcgaggaca acctctctga gggcattcgc      60
gagtggtggg ctttgaaacc tggagccccg caacccaaag ccaaccagca aaagcaggac     120
aacgctcggg gtctggtgct tcctggctac aagtacctcg gacccttcaa cggactcgac     180 aaggggagc ccgtcaacgc ggcggacgca gcggccctcg agcacgacaa ggcctacgac     240
cagcagctca aagcgggtga caatccgtac ctgaagtata accacgccga cgccgagttt     300
caggagcgtc tgaaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gcgcacagcc cgcgagaaag agactcaact ttgggcagac tggcgacaca     540
gagtcagtgc ccgaccctca accactcgga gaaccccccg cagcccctc tggtgtggga     600 tctaatacaa tggctgcagg cggtggcgct ccaatggcag acaataacga aggcgccgac     660
ggagtgggta gtgcctcagg aaattggcat tgcgattcca catggctggg cgacagagtc     720
atcaccacca gcacccgaac ctgggccctc cccacctaca acaaccacct ctacaagcaa     780
atctcctcag catccacagg agccagtaac gacaaccatt acttcggcta cagcacccc     840 tgggggtatt ttgactttaa cagattccac tgccacttct caccacgtga ctggcagcga     900
ctcatcaaca caactggggg attccggccc aagaaactca acttcaagct cttcaacatc     960
caggtcaagg aggtcacgca gaatgaaggc accaagacca tcgccaataa ccttaccagc    1020
acgattcagg tctttacgga ctcggactac cagctcccgt acgtcctcgg ctctgcgcac    1080
gagggctgcc tgcctccgtt cccggcggac gtcttcatga ttcctcagta cgggtacctg    1140
actctgaacg atggcagtca ggccgtgggc cgttcctcct tctactgcct ggagtacttt    1200
ccttctcaaa tgctgagaac gggcaacaac tttgagttca gctaccagtt tgaggacgtg    1260 cctttcaca gcagctacgc gcacagccaa agcctggacc ggctgatgaa ccccctcatc    1320
gaccagtacc tgtacttcct gtctcggact cagtccacgg gaggtaccgc aggaactcag    1380
cagttgctat tttctcaggc cgggcctagc aacatgtcgg ctcaggccaa aaactggcta    1440 cccgggcct gctaccggca gcaacgcgtc tccacggtaa ccaaccaaaa taacaatagc    1500
aactttgcct ggaccggtgc caccaagtat catctgaatg gcagagactc tctggtaaat    1560
cccggtatcg ctatggcaag ccacaaggaa ggagaagagc gatttttttcc gtccagcgga    1620 atcttaattt ttgggaaaca gggagctgga agagacaacg tggactatag caaagttatg    1680
ctaaccagtg aggaagaaat taaaaccacc aacccagtgg ccacagaaga atacggccaa    1740
gtggccgata acctgcaaag tgccaacacg gctcctattg tagggactgt caacagtcaa    1800
ggagccttac ctggcatggt ctggcagaac cgggacgtgt acctgcaggg tcctatctgg    1860
gccaagattc tcacacggga cggaaacttt catccctcgc cgctgatggg aggctttgga    1920
ctgaaacacc cgcctcctca gatcctgatt aagaatacac ctgttcccgc ggatcctcca    1980
actaccttca gtcaagctaa gctggcgtcg ttcatcacgc agtacagcac cggacaggtc    2040
agcgtggaaa ttgaatggga gctgcagaaa gaaaacagca aacgctggaa cccagagatt    2100

```
caatacactt ccaactacta caaatctaca aatgtggact ttgctgttaa cacagaaggc     2160
acttattctg agcctcgccc catcggcacc cgtttcctca cccgtaatct gtaa          2214
```

<210> SEQ ID NO 25
<211> LENGTH: 737
<212> TYPE: PRT
<213> ORGANISM: Artificial Sequence
<220> FEATURE:
<223> OTHER INFORMATION: Synthetic

<400> SEQUENCE: 25

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Arg Lys Arg Leu Asn Phe Gly Gln
                165                 170                 175

Thr Gly Asp Thr Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Asp Tyr Gln Leu
            340                 345                 350
```

-continued

```
Pro Tyr Val Leu Gly Ser Ala His Glu Gly Cys Leu Pro Pro Phe Pro
        355             360                 365

Ala Asp Val Phe Met Ile Pro Gln Tyr Gly Tyr Leu Thr Leu Asn Asp
    370             375                 380

Gly Ser Gln Ala Val Gly Arg Ser Ser Phe Tyr Cys Leu Glu Tyr Phe
385             390                 395                 400

Pro Ser Gln Met Leu Arg Thr Gly Asn Asn Phe Glu Phe Ser Tyr Gln
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Phe Leu Ser
        435                 440                 445

Arg Thr Gln Ser Thr Gly Gly Thr Ala Gly Thr Gln Gln Leu Leu Phe
    450                 455                 460

Ser Gln Ala Gly Pro Ser Asn Met Ser Ala Gln Ala Lys Asn Trp Leu
465                 470                 475                 480

Pro Gly Pro Cys Tyr Arg Gln Gln Arg Val Ser Thr Val Thr Asn Gln
                485                 490                 495

Asn Asn Asn Ser Asn Phe Ala Trp Thr Gly Ala Thr Lys Tyr His Leu
                500                 505                 510

Asn Gly Arg Asp Ser Leu Val Asn Pro Gly Ile Ala Met Ala Ser His
            515                 520                 525

Lys Glu Gly Glu Glu Arg Phe Phe Pro Ser Ser Gly Ile Leu Ile Phe
        530                 535                 540

Gly Lys Gln Gly Ala Gly Arg Asp Asn Val Asp Tyr Ser Lys Val Met
545                 550                 555                 560

Leu Thr Ser Glu Glu Glu Ile Lys Thr Thr Asn Pro Val Ala Thr Glu
            565                 570                 575

Glu Tyr Gly Gln Val Ala Asp Asn Leu Gln Ser Ala Asn Thr Ala Pro
            580                 585                 590

Ile Val Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Ser Gln Ala Lys Leu Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Tyr Lys Ser Thr Asn Val Asp Phe Ala Val Asn Thr Glu Gly
705                 710                 715                 720

Thr Tyr Ser Glu Pro Arg Pro Ile Gly Thr Arg Phe Leu Thr Arg Asn
                725                 730                 735

Leu
```

<210> SEQ ID NO 26
<211> LENGTH: 2214
<212> TYPE: DNA

-continued

```
<213> ORGANISM: Artificial Sequence
<220> FEATURE:
<223> OTHER INFORMATION: Synthetic

<400> SEQUENCE: 26
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg gaccccttcaa cggactcgac    180 aaggggagc ccgtcaacgc ggcggacgca gcggccctcg agcacgacaa ggcctacgac      240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tgcgggcatc     480
ggcaagtcgg gctcacagcc cgccaaaaaa agactcaatt ttggtcagac tggcgacaca     540
gagtcagttc cagaccctca acctatcgga gaacctccag cagcgccctc tggtgtggga     600
cctaatacaa tggctgcagg cggtggcgca ccaatggcag acaataacga aggcgccgac     660
ggagtgggta gttcctcggg aaaattggcat tgcgattcca catggctggg cgacagagtc     720
atcaccacca gcacccgaac ctgggccctg cccacctaca acaaccacct ctacaagcaa     780
atctcctcag catccacagg agccagtaac gacaaccatt acttcggcta cagcaccccc     840
tgggggtatt ttgactttaa cagattccac tgccactttt caccacgtga ctggcagcga     900
ctcatcaaca caactgggg attccggccc aagagactca gcttcaagct cttcaacatc      960
caggtcaagg aggtcacgca gaatgaaggc accaagacca tcgccaataa cctcaccagc    1020
accatccagg tgtttacgga ctcggagtac cagctgccgt acgttctcgg ctctgcccac    1080
cagggctgcc tgcctccgtt cccggcggac gtgttcatga ttccccagta cggctaccta    1140
acactcaaca acggtagtca ggccgtggga cgctcctcct tctactgcct ggaatacttt    1200
ccttcgcaga tgctgagaac cggcaacaac ttccagttta cttaccagtt cgaggacgtg    1260
cctttccaca gcagctacgc ccacagccag agcttggacc ggctgatgaa tcctctgatt    1320
gaccagtacc tgtacttctt gtctcggact caaacaacag gaggcacggc aaatacgcag    1380
cagctgctat tcagccaagg tgggcctaat acaatggcca atcaggcaaa gaactggctg    1440
ccaggaccct gttaccgcca acaacgcgtc tcaacggtaa ccgggcaaaa caacatcagc    1500
aactttgcct ggactgctgg gaccaaatac catctgaatg gaagaaattc attggctaat    1560
cctggcatcg ctatggcaac acacaaagac gacgaggagc gttttttttcc cagtaacggg    1620 atcctgattt ttggcaaaca aaatgctgcc agagacaatg cggattacag caaagtcatg    1680
ctcaccagcg aggaagaaat caaaaccact aaccctgtgg ctacagagga atacggtatc    1740
gtggcagata acttgcagca gcaaaacgcc gctcctcaaa ttggaactgt caacagccag    1800
ggggccttac ccggtatggt ctggcagaac cgggacgtgt acctgcaggg tcccatctgg    1860
gccaagattc ctcacacgga cggcaacttc caccgtctc cgctgatggg cggctttggc    1920
ctgaaacatc ctccgcctca gatcctgatc aagaacacgc ctgtacctgc ggatcctccg    1980
accaccttca accagtcaaa gctgaactct ttcatcacgc aatacagcac cggacaggtc    2040
agcgtggaaa ttgaatggga gctgcagaag gaaaacagca gcgctggaa ccccgagatc    2100 cagtacacct ccaactacta caaatctaca agtgtggact ttgctgttaa tacagaaggc    2160
gtgtactctg aaccccgccc cattggcacc cgtttcctca cccgtaatct gtaa          2214
```

-continued

<210> SEQ ID NO 27
<211> LENGTH: 737
<212> TYPE: PRT
<213> ORGANISM: Artificial Sequence
<220> FEATURE:
<223> OTHER INFORMATION: Synthetic

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ser Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

```
Ala Asp Val Phe Met Ile Pro Gln Tyr Gly Tyr Leu Thr Leu Asn Asn
    370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Thr Tyr Gln
            405             410             415

Phe Glu Asp Val Pro Phe His Ser Ser Tyr Ala His Ser Gln Ser Leu
            420             425             430

Asp Arg Leu Met Asn Pro Leu Ile Asp Gln Tyr Leu Tyr Phe Leu Ser
        435             440             445

Arg Thr Gln Thr Thr Gly Gly Thr Ala Asn Thr Gln Gln Leu Leu Phe
    450             455             460

Ser Gln Gly Gly Pro Asn Thr Met Ala Asn Gln Ala Lys Asn Trp Leu
465             470             475             480

Pro Gly Pro Cys Tyr Arg Gln Gln Arg Val Ser Thr Val Thr Gly Gln
            485             490             495

Asn Asn Ile Ser Asn Phe Ala Trp Thr Ala Gly Thr Lys Tyr His Leu
            500             505             510

Asn Gly Arg Asn Ser Leu Ala Asn Pro Gly Ile Ala Met Ala Thr His
            515             520             525

Lys Asp Asp Glu Glu Arg Phe Phe Pro Ser Asn Gly Ile Leu Ile Phe
    530             535             540

Gly Lys Gln Asn Ala Ala Arg Asp Asn Ala Asp Tyr Ser Lys Val Met
545             550             555             560

Leu Thr Ser Glu Glu Glu Ile Lys Thr Thr Asn Pro Val Ala Thr Glu
            565             570             575

Glu Tyr Gly Ile Val Ala Asp Asn Leu Gln Gln Gln Asn Ala Ala Pro
            580             585             590

Gln Ile Gly Thr Val Asn Ser Gln Gly Ala Leu Pro Gly Met Val Trp
        595             600             605

Gln Asn Arg Asp Val Tyr Leu Gln Gly Pro Ile Trp Ala Lys Ile Pro
    610             615             620

His Thr Asp Gly Asn Phe His Pro Ser Pro Leu Met Gly Gly Phe Gly
625             630             635             640

Leu Lys His Pro Pro Pro Gln Ile Leu Ile Lys Asn Thr Pro Val Pro
            645             650             655

Ala Asp Pro Pro Thr Thr Phe Asn Gln Ser Lys Leu Asn Ser Phe Ile
            660             665             670

Thr Gln Tyr Ser Thr Gly Gln Val Ser Val Glu Ile Glu Trp Glu Leu
            675             680             685

Gln Lys Glu Asn Ser Lys Arg Trp Asn Pro Glu Ile Gln Tyr Thr Ser
    690             695             700

Asn Tyr Tyr Lys Ser Thr Ser Val Asp Phe Ala Val Asn Thr Glu Gly
705             710             715             720

Val Tyr Ser Glu Pro Arg Pro Ile Gly Thr Arg Phe Leu Thr Arg Asn
            725             730             735

Leu
```

<210> SEQ ID NO 28
<211> LENGTH: 2214
<212> TYPE: DNA
<213> ORGANISM: Artificial Sequence
<220> FEATURE:
<223> OTHER INFORMATION: Synthetic -continued

```
<400> SEQUENCE: 28
atggctgccg atggttatct tccagattgg ctcgaggaca acctctctga gggcattcgc        60
gagtggtggg acttgaaacc tggagccccg aaacccaaag ccaaccagca aaagcaggac       120
aacggccggg gtctggtgct tcctggctac aagtacctcg gacccttcaa cggactcgac       180 aaggggggagc ccgtcaacgc ggcggacgca gcggccctcg agcacgacaa ggcctacgac      240
cagcagctca aagcgggtga caatccgtac ctgaagtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaga gaccggtaga gccatcaccc cagcgttctc cagactcctc tgcgggcatc       480
ggcaagtcgg gcgcacagcc cgcgaaaaag agactcaact ttgggcagac tggcgactca       540
gagtcagtgc ccgaccctca accaatcgga gaaccccccg caggcccctc tggtctggga       600
tctaatacaa tggctgcagg cggtggcgct ccaatggcag acaataacga aggcgccgac       660
ggagtgggta gtgcctcagg aaattggcat tgcgattcca catggctggg cgacagagtc       720
atcaccacca gcacccgaac ctgggcccctc cccacctaca acaaccacct ctacaagcaa       780
atctcctcag catccacagg agccagtaac gacaaccatt acttcggcta cagcaccccc       840
tgggggtatt ttgactttaa cagattccac tgccacttct caccacgtga ctggcagcga       900
ctcatcaaca caaactgggg attccggccc aagaaactca acttcaagct cttcaacatc       960
caggtcaagg aggtcacgca gaatgaaggc accaagacca tcgccaataa ccttaccagc      1020
acgattcagg tctttacgga ctcggactac cagctcccgt acgtcctcgg ctctgcgcac      1080
gagggctgcc tgcctccgtt cccggcggac gtcttcatga ttcctcagta cgggtacctg      1140
actctgaacg atggcagtca ggccgtgggc cgttcctcct tctactgcct ggagtacttt      1200
ccttctcaaa tgctgagaac gggcaacaac tttgagttca gctaccagtt tgaggacgtg      1260
ccttttcaca gcagctacgc gcacagccaa agcctggacc ggctgatgaa ccccctcatc      1320
gaccagtacc tgtacttcct gtctcggact cagtccacgg gaggtaccgc aggaactcag      1380
cagttgctat tttctcaggc cgggcctagc aacatgtcgg ctcaggccaa aaactggcta      1440
cccgggccct gctaccggca gcaacgcgtc tccacggtaa ccaaccaaaa taacatcagc      1500
aactttgcct ggaccggtgc caccaagtat catctgaatg gcagagactc tctggtaaat      1560
cccggtatcg ctatggcaag ccacaaggaa ggagaagagc gatttttttcc gtccagcgga      1620 atcttaattt ttgggaaaca gggagctgga agagacaacg tggactatag caaagttatg      1680
ctaaccagtg aggaagaaat taaaaccacc aacccagtgg ccacagaaca gtacggccaa      1740
gtggccgata acctgcaaca gcaaaacgcc gctcctattg tagggactgt caacagtcaa      1800
ggagccttac ctggcatggt ctggcagaac cgggacgtgt acctgcaggg tcctatctgg      1860
gccaagattc ctcacacgga cggaaactttt catccctcgc cgctgatggg aggctttgga      1920
ctgaaacacc cgcctcctca gatcctgatt aagaatacac ctgttccccgc ggatcctcca      1980 actaccttca gtcaagctaa gctggcgtcg ttcatcacgc agtacagcac cggacaggtc      2040
agcgtggaaa ttgaatggga gctgcagaaa gaaaacagca aacgctggaa cccagagatt      2100
caatacactt ccaactacta caaatctaca aatgtggact ttgctgttaa cacagaaggc      2160
acttattctg agcctcgccc catcggcacc cgtttcctca cccgtaatct gtaa           2214

<210> SEQ ID NO 29
```

<211> LENGTH: 737
<212> TYPE: PRT
<213> ORGANISM: Artificial Sequence
<220> FEATURE:
<223> OTHER INFORMATION: Synthetic

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

-continued

```
Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Gln
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Phe Leu Ser
            435                 440                 445

Arg Thr Gln Ser Thr Gly Gly Thr Ala Gly Thr Gln Gln Leu Leu Phe
        450                 455                 460

Ser Gln Ala Gly Pro Ser Asn Met Ser Ala Gln Ala Lys Asn Trp Leu
465                 470                 475                 480

Pro Gly Pro Cys Tyr Arg Gln Gln Arg Val Ser Thr Val Thr Asn Gln
                485                 490                 495

Asn Asn Ile Ser Asn Phe Ala Trp Thr Gly Ala Thr Lys Tyr His Leu
            500                 505                 510

Asn Gly Arg Asp Ser Leu Val Asn Pro Gly Ile Ala Met Ala Ser His
            515                 520                 525

Lys Glu Gly Glu Glu Arg Phe Phe Pro Ser Ser Gly Ile Leu Ile Phe
        530                 535                 540

Gly Lys Gln Gly Ala Gly Arg Asp Asn Val Asp Tyr Ser Lys Val Met
545                 550                 555                 560

Leu Thr Ser Glu Glu Glu Ile Lys Thr Thr Asn Pro Val Ala Thr Glu
                565                 570                 575

Gln Tyr Gly Gln Val Ala Asp Asn Leu Gln Gln Gln Asn Ala Ala Pro
            580                 585                 590

Ile Val Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Ser Gln Ala Lys Leu Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Tyr Lys Ser Thr Asn Val Asp Phe Ala Val Asn Thr Glu Gly
705                 710                 715                 720

Thr Tyr Ser Glu Pro Arg Pro Ile Gly Thr Arg Phe Leu Thr Arg Asn
                725                 730                 735

Leu
```

<210> SEQ ID NO 30
<211> LENGTH: 2214
<212> TYPE: DNA
<213> ORGANISM: Artificial Sequence
<220> FEATURE:
<223> OTHER INFORMATION: Synthetic

<400> SEQUENCE: 30

-continued

```
atggctgccg atggttatct tccagattgg ctcgaggaca acctctctga gggcattcgc     60
gagtggtggg ctttgaaacc tggagccccg caacccaaag ccaaccagca aaagcaggac    120
aacgctcggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgaagtata accacgccga cgccgagttt    300
caggagcgtc tgaaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tgcgggcatc    480
ggcaagtcgg gcgcacagcc cgcgagaaag agactcaact ttgggcagac tggcgacaca    540
gagtcagtgc ccgaccctca accactcgga gaaccccccg cagcccctc tggtgtggga    600 tctaatacaa tggctgcagg cggtggcgct ccaatggcag acaataacga aggcgccgac    660
ggagtgggta gtgcctcagg aaattggcat tgcgattcca catggctggg cgacagagtc    720
atcaccacca gcacccgaac ctgggccctc cccacctaca acaaccacct ctacaagcaa    780
atctcctcag catccacagg agccagtaac gacaaccatt acttcggcta cagcacccccc    840 tgggggtatt ttgactttaa cagattccac tgccacttct caccacgtga ctggcagcga    900
ctcatcaaca acaactgggg attccggccc aagaaactca acttcaagct cttcaacatc    960
caggtcaagg aggtcacgca gaatgaaggc accaagacca tcgccaataa ccttaccagc   1020
acgattcagg tctttacgga ctcggactac cagctcccgt acgtcctcgg ctctgcgcac   1080
gagggctgcc tgcctccgtt cccggcggac gtcttcatga ttcctcagta cgggtacctg   1140
actctgaacg atggcagtca ggccgtgggc cgttcctcct tctactgcct ggagtacttt   1200
ccttctcaaa tgctgagaac gggcaacaac tttgagttca gctaccagtt tgaggacgtg   1260
ccttttcaca gcagctacgc gcacagccaa agcctggacc ggctgatgaa ccccctcatc   1320
gaccagtacc tgtacttcct gtctcggact cagtccacgg gaggtaccgc aggaactcag   1380
cagttgctat tttctcaggc cgggcctagc aacatgtcgg ctcaggccaa aaactggcta   1440
cccgggcccc gctaccggca gcaacgcgtc tccacggtaa ccaaccaaaa taacatcagc   1500
aactttgcct ggaccggtgc caccaagtat catctgaatg gcagagactc tctggtaaat   1560
cccggtatcg ctatggcaag ccacaaggaa ggagaagagc gatttttttcc gtccagcgga   1620 atcttaattt ttgggaaaca gggagctgga agagacaacg tggactatag caaagttatg   1680
ctaaccagtg aggaagaaat taaaaccacc aacccagtgg ccacagaaga atacggccaa   1740
gtggccgata acctgcaaag tgccaacacg gctcctattg tagggactgt caacagtcaa   1800
ggagccttac ctggcatggt ctggcagaac cgggacgtgt acctgcaggg tcctatctgg   1860
gccaagattc tcacacggac cggaaacttt catccctcgc cgctgatggg aggctttgga   1920
ctgaaacacc cgcctcctca gatcctgatt aagaatacac ctgttccgcg ggatcctcca   1980
actaccttca gtcaagctaa gctggcgtcg ttcatcacgc agtacagcac cggacaggtc   2040
agcgtggaaa ttgaatggga gctgcagaaa gaaaacagca aacgctggaa cccagagatt   2100
caatacactt ccaactacta caaatctaca aatgtggact ttgctgttaa cacagaaggc   2160
acttattctg agcctcgccc catcggcacc cgtttcctca cccgtaatct gtaa          2214
```

<210> SEQ ID NO 31
<211> LENGTH: 737
<212> TYPE: PRT
<213> ORGANISM: Artificial Sequence -continued
<220> FEATURE:
<223> OTHER INFORMATION: Synthetic

<400> SEQUENCE: 31

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ala Gly Ile
145                 150                 155                 160

Gly Lys Ser Gly Ala Gln Pro Ala Arg Lys Arg Leu Asn Phe Gly Gln
            165                 170                 175

Thr Gly Asp Thr Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Gln Asn Glu Gly Thr Lys Thr Ile Ala Asn
            325                 330                 335

Asn Leu Thr Ser Thr Ile Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

-continued

```
Pro Ser Gln Met Leu Arg Thr Gly Asn Asn Phe Glu Phe Ser Tyr Gln
            405             410             415

Phe Glu Asp Val Pro Phe His Ser Ser Tyr Ala His Ser Gln Ser Leu
            420             425             430

Asp Arg Leu Met Asn Pro Leu Ile Asp Gln Tyr Leu Tyr Phe Leu Ser
            435             440             445

Arg Thr Gln Ser Thr Gly Gly Thr Ala Gly Thr Gln Gln Leu Leu Phe
    450             455             460

Ser Gln Ala Gly Pro Ser Asn Met Ser Ala Gln Ala Lys Asn Trp Leu
465             470             475             480

Pro Gly Pro Cys Tyr Arg Gln Gln Arg Val Ser Thr Val Thr Asn Gln
            485             490             495

Asn Asn Ile Ser Asn Phe Ala Trp Thr Gly Ala Thr Lys Tyr His Leu
            500             505             510

Asn Gly Arg Asp Ser Leu Val Asn Pro Gly Ile Ala Met Ala Ser His
            515             520             525

Lys Glu Gly Glu Glu Arg Phe Phe Pro Ser Ser Gly Ile Leu Ile Phe
    530             535             540

Gly Lys Gln Gly Ala Gly Arg Asp Asn Val Asp Tyr Ser Lys Val Met
545             550             555             560

Leu Thr Ser Glu Glu Glu Ile Lys Thr Thr Asn Pro Val Ala Thr Glu
            565             570             575

Glu Tyr Gly Gln Val Ala Asp Asn Leu Gln Ser Ala Asn Thr Ala Pro
            580             585             590

Ile Val Gly Thr Val Asn Ser Gln Gly Ala Leu Pro Gly Met Val Trp
            595             600             605

Gln Asn Arg Asp Val Tyr Leu Gln Gly Pro Ile Trp Ala Lys Ile Pro
    610             615             620

His Thr Asp Gly Asn Phe His Pro Ser Pro Leu Met Gly Gly Phe Gly
625             630             635             640

Leu Lys His Pro Pro Pro Gln Ile Leu Ile Lys Asn Thr Pro Val Pro
            645             650             655

Ala Asp Pro Pro Thr Thr Phe Ser Gln Ala Lys Leu Ala Ser Phe Ile
            660             665             670

Thr Gln Tyr Ser Thr Gly Gln Val Ser Val Glu Ile Glu Trp Glu Leu
            675             680             685

Gln Lys Glu Asn Ser Lys Arg Trp Asn Pro Glu Ile Gln Tyr Thr Ser
    690             695             700

Asn Tyr Tyr Lys Ser Thr Asn Val Asp Phe Ala Val Asn Thr Glu Gly
705             710             715             720

Thr Tyr Ser Glu Pro Arg Pro Ile Gly Thr Arg Phe Leu Thr Arg Asn
            725             730             735

Leu

<210> SEQ ID NO 32
<211> LENGTH: 736
<212> TYPE: PRT
<213> ORGANISM: Artificial Sequence
<220> FEATURE:
<223> OTHER INFORMATION: Synthetic

<400> SEQUENCE: 32

Met Ala Ala Asp Gly Tyr Leu Pro Asp Trp Leu Glu Asp Asn Leu Ser
1               5               10              15
```

-continued

```
Glu Gly Ile Arg Glu Trp Trp Asp Leu Lys Pro Gly Ala Pro Lys Pro
            20                  25              30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
```

-continued

```
         435                 440                 445
Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
            565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

AAV CAPSID VARIANTS FOR GENE THERAPY

RELATED APPLICATIONS

This application is a national stage filing under 35 U.S.C. § 371 of International Patent Application Serial No. PCT/US2020/046543, filed Aug. 14, 2020, entitled "AAV CAPSID VARIANTS FOR GENE THERAPY", which claims the benefit under 35 U.S.C. § 119 (e) of the filing date of U.S. Provisional Application Ser. No. 62/886,915, filed Aug. 14, 2019, entitled "AAV CAPSID VARIANTS FOR GENE THERAPY", the entire contents of each of which are incorporated herein by reference in their entirety.

SEQUENCE LISTING

In accordance with 37 C.F.R. 1.52 (e) (5), the present specification makes reference to a Sequence Listing (submitted electronically as a .txt file named "U119770161US01-SEQ-KSB"). The .txt file was generated on Feb. 10, 2022 and is 163,870 bytes in size. The Sequence Listing is herein incorporated by reference in its entirety.

BACKGROUND

Recombinant adeno-associated viruses (rAAV) have moved into the clinic as gene transfer vectors for a number of different diseases. While in some cases the vectors are delivered directly into the tissue of interest, in a growing number of diseases the delivery is systemic. Thus, the development of new AAV variants of with differing tissue tropisms, as well as higher efficiencies of transduction, is highly desirable.

SUMMARY

Disclosed herein are variant recombinant adeno-associated virus (rAAV) capsid proteins, nucleic acids encoding such proteins, rAAV particles comprising such proteins (e.g., encapsidating a rAAV genome encoding a gene of interest). In some embodiments, compositions described in this application are useful to produce rAAV particles, and/or to deliver one or more genes of interest to a target tissue (e.g., to a muscle tissue, for example to cardiac or skeletal muscle).

When used for the treatment of muscle diseases, large amounts of virus are needed to transduce the skeletal and/or cardiac muscles of the body. Unfortunately, large amounts of virus can also trigger a number of different types of undesirable immune responses that can be life threatening to patients. Accordingly, there is a need to optimize the tropism of the virus for the tissue of interest, while decreasing uptake of virus in non-targeted tissues.

In some embodiments, disclosed herein are variant recombinant adeno-associated virus (rAAV) serotype 8 (AAV8) capsid proteins having one or more amino acid substitutions that enhance tissue tropism (e.g., muscle tropism). In some embodiments, rAAV capsid proteins comprise one or more additional amino acid substitutions that reduce brain and/or liver tropism.

In some embodiments, the rAAV8 capsid proteins include one or more of any one or more of the changes as shown in FIG. 1. In some embodiments, the rAAV8 capsid protein comprises an amino acid sequence as set forth in SEQ ID NO: 11.

In some embodiments, the rAAV8 capsid proteins further comprise any one or more of the following changes: N500I; N263S; G264A; T265S; S266T; deletion of G268; T270S; and T274H. In some embodiments, the rAAV8 capsid protein comprises an amino acid sequence as set forth in SEQ ID NO: 15. In some embodiments, the rAAV8 capsid protein comprises an amino acid sequence as set forth in SEQ ID NO: 21. In some embodiments, the rAAV8 capsid protein comprises an amino acid sequence as set forth in SEQ ID NO: 27.

In some embodiments, the rAAV8 capsid proteins include one or more of the following substitutions: A24D, D41N, Q84K, R92K, T158A, K163S, R169K, L189I, A195G, V199L, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, E578Q, I581Q, T591A, Q594I, I595V, N665S, S667A, N670A, S712N, V722T, and Y733F. In some embodiments, the rAAV8 capsid protein comprises an amino acid sequence as set forth in SEQ ID NO: 12.

In some embodiments, the rAAV8 capsid proteins further comprise any one or more of the following changes: N500I; N263S; S264A; T265S; S266T; deletion of G268; S269A; T270S; and T274H. In some embodiments, the rAAV8 capsid protein comprises an amino acid sequence as set forth in SEQ ID NO: 17. In some embodiments, the rAAV8 capsid protein comprises an amino acid sequence as set forth in SEQ ID NO: 23. In some embodiments, the rAAV8 capsid protein comprises an amino acid sequence as set forth in SEQ ID NO: 29.

In some embodiments, the rAAV8 capsid protein includes one or more of the following substitutions: K31Q, D41N, G42A, Q84K, R92K, Q105K, T158A, K163S, S180T, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, I581Q, Q588S, Q589A, Q594I, I595V, N665S, S667A, N670A, S712N, V722T, and Y733F. In some embodiments, the rAAV8 capsid protein comprises an amino acid sequence as set forth in SEQ ID NO: 13.

In some embodiments, the rAAV8 capsid proteins further comprise any one or more of the following changes: N500I; N263S; S264A; T265S; S266T; deletion of G268; S269A; T270S; and T274H. In some embodiments, the rAAV8 capsid protein comprises an amino acid sequence as set forth in SEQ ID NO: 19. In some embodiments, the rAAV8 capsid protein comprises an amino acid sequence as set forth in SEQ ID NO: 25. In some embodiments, the rAAV8 capsid protein comprises an amino acid sequence as set forth in SEQ ID NO: 31.

Further disclosed are variant rAAV capsid proteins of a serotype other than serotype 8 (e.g., AAV2, AAV3, AAV4, AAV5, AAV6, AAV7, AAV9, AAV10, AAVrh10, AAVrh74, AAVanc80L65, etc.) comprising any one or more of the disclosed amino acid changes. In some embodiments, the amino acid substitution(s) are at position(s) in the capsid protein of a serotype other than serotype 8 corresponding to the position(s) of the substitution(s) in AAV8. Accordingly, in some embodiments, one or more (e.g., 2, 3, 4, 5, 6, 7, 8, 9, 10, or more) of the amino acid substitutions illustrated in FIG. 1, FIG. 4, and or SEQ ID NOs: 2, 4, 6, 11-13, 15, 17, 19, 21, 23, 25, 27, 29, and/or 31 can be included in an rAAV8 based capsid protein, or in an rAAV capsid protein that is based on a different serotype (e.g., in any of the capsid proteins set forth in SEQ ID NOs: 7-10), and/or related rAAV particles (e.g., comprising a nucleic acid encoding a gene of interest). In some embodiments, a variant capsid protein can be a variant VP1, VP2, or VP3 capsid protein. In some embodiments, a variant capsid protein comprises a subset of the amino acid substitutions illustrated in FIG. 1 and FIG. 4, for example a subset that has 1, 2, 3, 4, 5, 6, 7, 8, 9, or 10 fewer amino acid substitutions than those illustrated in FIG. 1 and FIG. 4.

Also disclosed are variant recombinant AAV (e.g., rAAV8) particles comprising the recombinant AAV (e.g., rAAV8) capsid proteins disclosed. In some embodiments, the AAV (e.g., rAAV8) particles include a nucleic acid comprising a gene of interest. In some embodiments, the nucleic acid is single stranded. In some embodiments, the nucleic acid is double stranded.

Also disclosed are compositions comprising a plurality of the variant recombinant AAV (e.g., rAAV8) particles disclosed herein. These compositions may include a pharmaceutically acceptable carrier.

Also provided are methods of transducing a cell with a gene of interest, comprising providing to the cell a composition disclosed herein, wherein the AAV (e.g., rAAV8) particles in the composition comprise the gene of interest. Further provided are methods of transducing a cell with a gene of interest, comprising providing to the cell a composition comprising a plurality of recombinant AAV (e.g., rAAV8) particles comprising a variant recombinant AAV (e.g., rAAV8) capsid protein disclosed herein, and wherein the AAV (e.g., rAAV8) particles in the composition comprise the gene of interest. In some embodiments, the gene of interest encodes a therapeutic protein. In some embodiments, the therapeutic protein is an antibody or antibody fragment, a peptibody, a growth factor, a hormone, a membrane protein, a cytokine, a chemokine, an activating or inhibitory peptide acting on cell surface receptors or ion channels, a cell-permeant peptide targeting intracellular processes, an enzyme, a nuclease or other protein used for gene editing. In some embodiments, the subject is a mammal. In some embodiments, the subject is a human.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1E shows an alignment of AAV variants SL1.2, SL2, and SL3 with other commonly used AAV vectors AAV8, AAV9, AAVrh10, AAVrh74, and AAVanc80L65. Red indicates identical amino acids across all capsids compared; orange indicates that one of the sequences compared substitutes a different amino acid; green indicates that two of the sequences compared substitute a different amino acid; blue indicates that three or more of the sequences compared substitute a different amino acid.

FIG. 3 shows the percent sequence homology/divergence of AAV variants SL1.2, SL2, SL3, AAV8, AAV9, AAVrh10, AAVrh74, and AAVanc80L65.

FIGS. 4A-4J show an alignment of AAV variants SL1.2, SL1.2L, SL1.2B, SL1.2LB, SL2, SL2L, SL2B, SL2LB, SL3, SL3L, SL3B, and SL3LB with other commonly used AAV vectors AAV8, AAV9, AAVrh10, AAVrh74, and AAVanc80L65. The "L" suffix refers to the single amino acid change that has been reported to result in less efficient liver targeting. The "B" suffix refers to an eight amino acid substitution/deletion that has been reported to impair crossing of the blood-brain barrier. The "LB" suffix refers to the single amino acid change that has been reported to result in less efficient liver targeting (L) combined with an eight amino acid substitution/deletion that has been reported to impair crossing of the blood-brain barrier. Red indicates identical amino acids across all capsids compared; orange indicates that one of the sequences compared substitutes a different amino acid; green indicates that two of the sequences compared substitute a different amino acid; blue indicates that three or more of the sequences compared substitute a different amino acid.

FIG. 6 shows the percent sequence homology/divergence of AAV variants SL1.2, SL1.2L, SL1.2B, SL1.2LB, SL2, SL2L, SL2B, SL2LB, SL3, SL3L, SL3B, SL3LB, AAV8, AAV9, AAVrh10, AAVrh74, and AAVanc80L65.

DETAILED DESCRIPTION

Figure 1A:
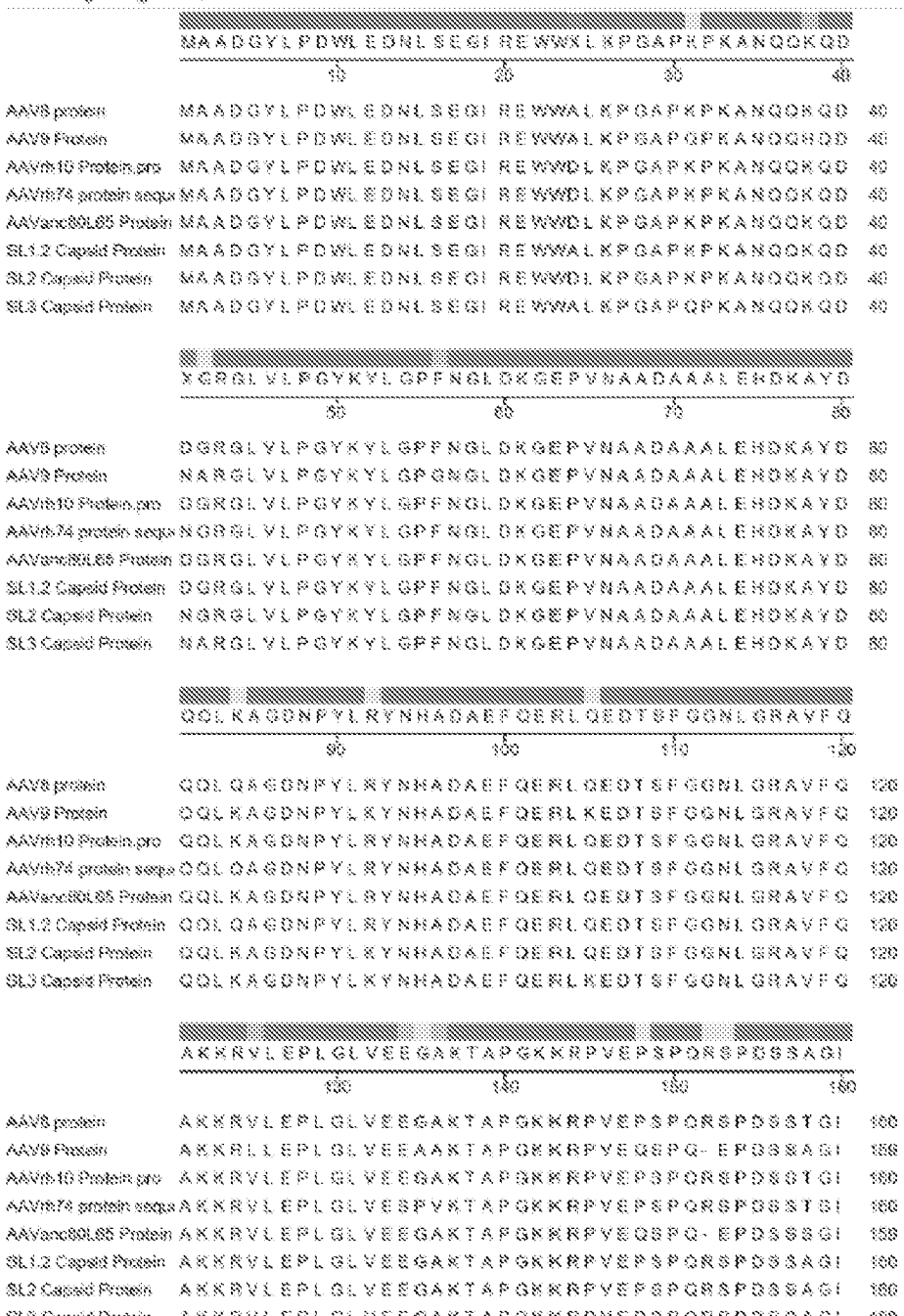
Figure 1B:
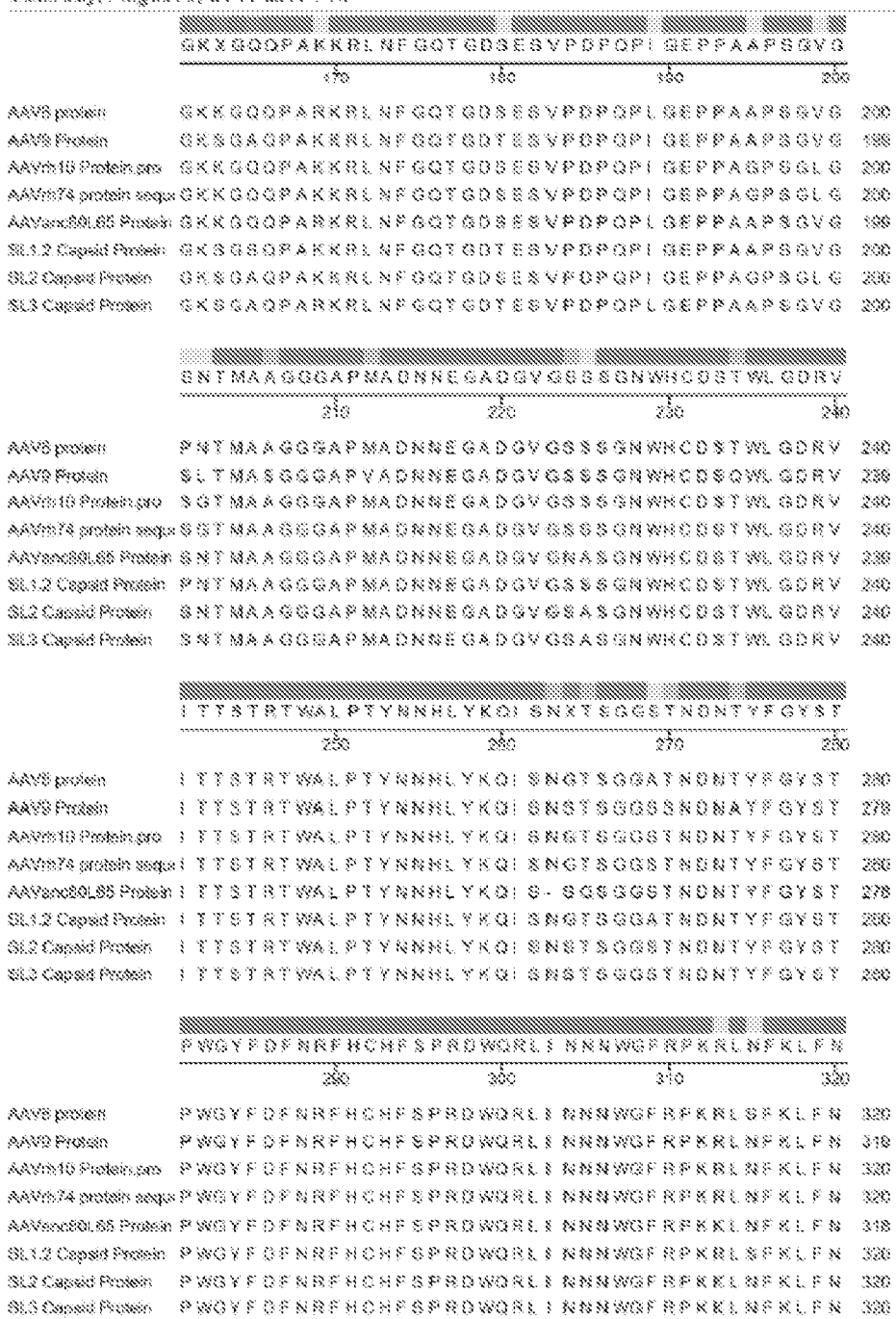
Figure 1C:
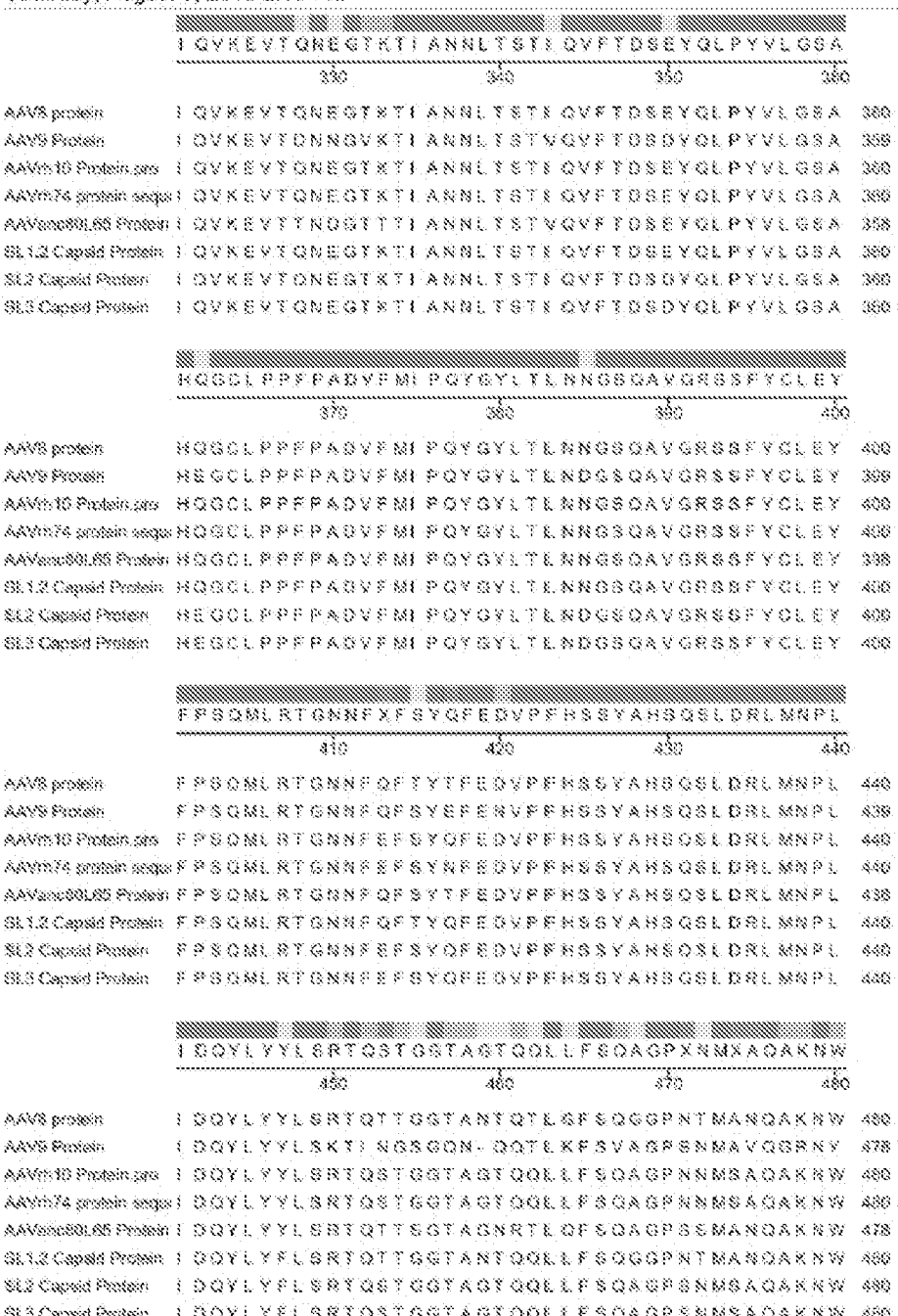
Figure 1D:
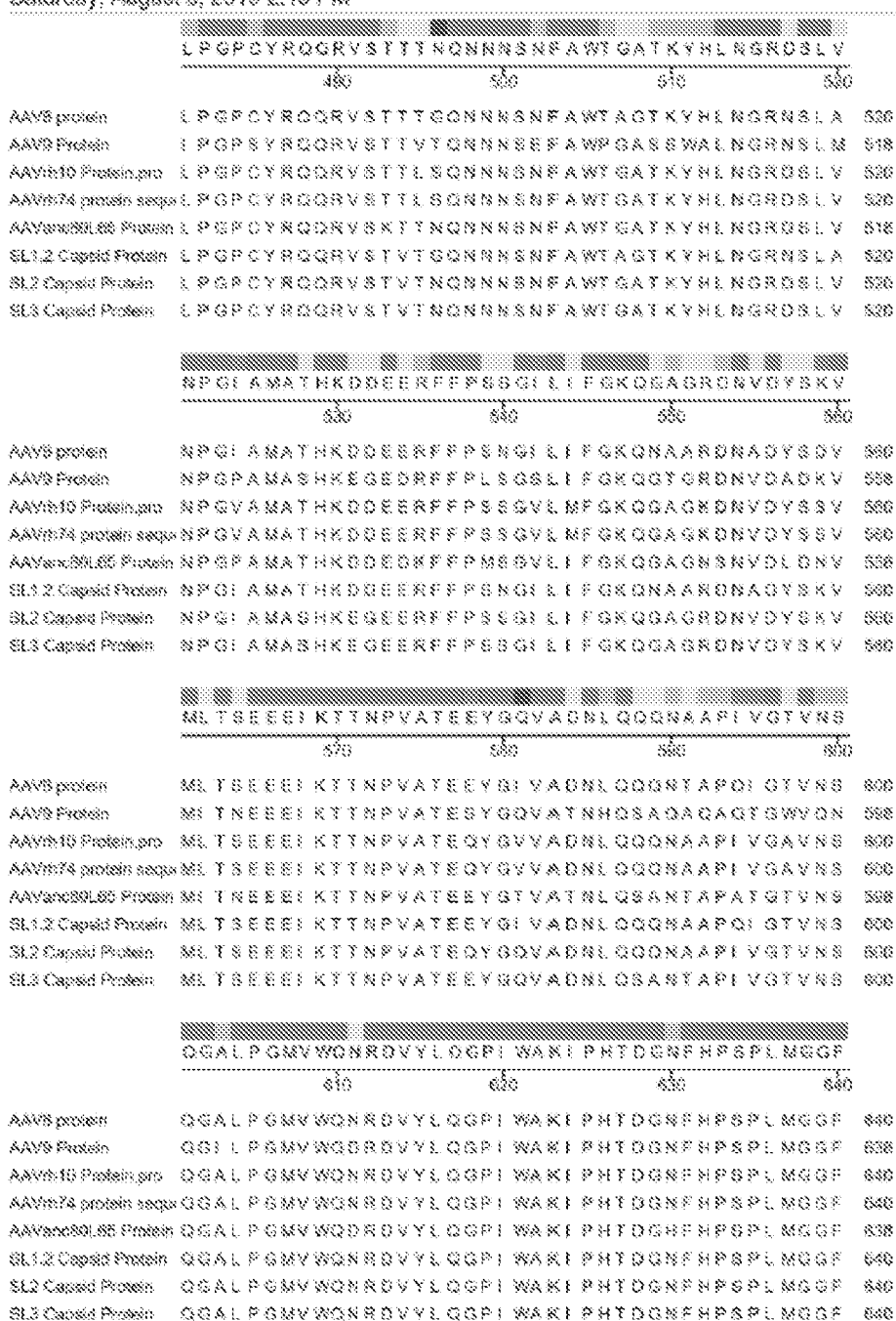

AAV-derived vectors are promising tools for human gene therapy applications because of reduced pathogenicity compared to other vectors, episomal localization, and stable transgene expression. AAV particles show huge promise for the delivery of therapeutic genes. The organ or tissue tropism of AAV particles depends highly, if not entirely, on the make-up of the particle surface, or the capsid. Disclosed herein are AAV variants that alter the tropisms and/or efficiencies of AAV transduction as compared to AAV8. These vectors can be used in the clinic for either veterinary or human use. The tissue tropism may differ depending on the mammalian species. The basis of the differences in tissue tropism and efficiencies is based primarily on sequence variations in surface loops.

AAV serotype 8 (AAV8) has a tropism for and may be used to deliver genes to skeletal muscle, retinal pigment epithelium, photoreceptors, cardiac tissue, and hepatocytes. As is typical for AAVs, the AAV8 capsid is made up of three proteins, VP1, VP2 and VP3, the product of three different but overlapping transcripts of the single AAV cap gene. Provided herein are compositions and methods for variant recombinant AAV8-like capsid proteins and particles that alter the tropisms and/or efficiencies of AAV transduction as compared to AAV8. This disclosure is based, at least in part, on the identification of recombinant AAV (e.g., rAAV8) variant proteins and particles that alter tissue tropism and alter transduction efficiency compared to wild-type rAAV (e.g., rAAV8) protein and particles.

As used herein, the term "variant" refers to a nucleic acid or protein having characteristics that deviate from what occurs in nature, e.g., a "variant" is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type nucleic acid or protein. For instance, a transgene variant is a nucleic acid comprising one or more substitutions in the nucleotides of a transgene, as compared to the wild type sequence thereof. These substitutions may be silent, i.e. they do not modify the amino acid sequence of any encoded protein (or otherwise result in a variant amino acid sequence). Alternatively, these substitutions may result in modifications to the amino acid sequence of an encoded protein, resulting in an encoded protein having one or more amino acid substitutions (e.g., having 1, 2, 3, 4, 5, 6, 7, 8, 9, 10, 10-15, or 15-20 amino acid substitutions) relative to the wild type protein sequence. These substitutions include chemical modifications as well as truncations. This term further embraces functional fragments of a wild type nucleic acid or amino acid sequence. These modifications of the reference sequence may occur at the 5' or 3' ends of the reference sequence or anywhere between those positions, interspersed either individually among nucleotides or peptides in the reference sequence or in one or more contiguous groups within the reference sequence.

In some embodiments, the variant recombinant adeno-associated virus (rAAV) capsid proteins disclosed herein have a Y to F substitution at position 447 and a T to V substitution at position 494 made in a background comprising serotype 8 (AAV8) VP1 or VP2 or VP3. In some embodiments, the variant recombinant AAV (e.g., rAAV8) capsid protein comprises the amino acid sequence set forth in SEQ ID NO: 11. In some embodiments, the variant recombinant AAV (e.g., rAAV8) capsid protein has an amino acid sequence identified as SL1.2 Capsid Protein in FIGS. 1A-1E. In some embodiments, the variant recombinant AAV (e.g., rAAV8) capsid protein includes one or more of the following substitutions: K163S, R169K, S180T, L189I, T417Q, Y447F, T462Q, G464L, T494V, D559K, T591A, and Y733F. In one embodiment, the variant recombinant AAV (e.g., rAAV8) capsid protein includes substitutions K163S, R169K, S180T, L189I, T417Q, Y447F, T462Q, G464L, T494V, D559K, T591A, and Y733F.

In some embodiments, the variant recombinant AAV (e.g., rAAV8) capsid protein includes one or more of the following substitutions: A24D, D41N, Q84K, R92K, T158A, K163S, R169K, L189I, A195G, V199L, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, E578Q, I581Q, T591A, Q594I, I595V, N665S, S667A, N670A, S712N, V722T, and Y733F. In one embodiment, the variant recombinant AAV (e.g., rAAV8) capsid protein includes substitutions A24D, D41N, Q84K, R92K, T158A, K163S, R169K, L189I, A195G, V199L, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, E578Q, I581Q, T591A, Q594I, I595V, N665S, S667A, N670A, S712N, V722T, and Y733F. In some embodiments, the variant recombinant AAV (e.g., rAAV8) comprises the amino acid sequence set forth in SEQ ID NO: 12. In some embodiments, the variant recombinant AAV (e.g., rAAV8) capsid protein has an amino acid sequence identified as SL2 Capsid Protein in FIGS. 1A-1E.

In some embodiments, the variant rAAV capsid protein has a Y to F substitution at position 447 and a T to V substitution at position 494 made in a background comprising serotype 8 (AAV8) VP1, VP2 or VP3, and includes any one or more of the following substitutions: K31Q, D41N, G42A, Q84K, R92K, Q105K, T158A, K163S, S180T, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, I581Q, Q588S, Q589A, Q594I, I595V, N665S, S667A, N670A, S712N, V722T, and Y733F. In one embodiment, the variant recombinant AAV (e.g., rAAV8) capsid protein includes substitutions K31Q, D41N, G42A, Q84K, R92K, Q105K, T158A, K163S, S180T, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, I581Q, Q588S, Q589A, Q594I, I595V, N665S, S667A, N670A, S712N, V722T, and Y733. In some embodiments, the variant recombinant AAV (e.g., rAAV8) comprises the amino acid sequence set forth in SEQ ID NO: 13. In some embodiments, the variant recombinant AAV (e.g., rAAV8) capsid protein has an amino acid sequence identified as SL3 Capsid Protein in FIGS. 1A-1E.

AAV8 Structure and Capsid Proteins

The wild-type AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The rep ORF is composed of four overlapping genes encoding Rep proteins required for the AAV life cycle. The cap ORF contains overlapping nucleotide sequences of capsid proteins: VP1, VP2 and VP3, which interact together to form a capsid of an icosahedral symmetry.

```
Wild-type AAV8 amino acid sequence:
                                (SEQ ID NO: 7)
MAADGYLPDWLEDNLSEGIREWWALKPGAPKPKAN

QQKQDDGRGLVLPGYKYLGPFNGLDKGEPVNAADA

AALEHDKAYDQQLQAGDNPYLRYNHADAEFQERLQ

EDTSFGGNLGRAVFQAKKRVLEPLGLVEEGAKTAP

GKKRPVEPSPQRSPDSSTGIGKKGQQPARKRLNFG

QTGDSESVPDPQPLGEPPAAPSGVGPNTMAAGGGA

PMADNNEGADGVGSSSGNWHCDSTWLGDRVITTST

RTWALPTYNNHLYKQISNGTSGGATNDNTYFGYST

PWGYFDFNRFHCHFSPRDWQRLINNNWGFRPKRLS

FKLFNIQVKEVTQNEGTKTIANNLTSTIQVFTDSE

YQLPYVLGSAHQGCLPPFPADVFMIPQYGYLTLNN

GSQAVGRSSFYCLEYFPSQMLRTGNNFQFTYTFED

VPFHSSYAHSQSLDRLMNPLIDQYLYYLSRTQTTG

GTANTQTLGFSQGGPNTMANQAKNWLPGPCYRQQR

VSTTTGQNNNSNFAWTAGTKYHLNGRNSLANPGIA

MATHKDDEERFFPSNGILIFGKQNAARDNADYSDV

MLTSEEEIKTTNPVATEEYGIVADNLQQQNTAPQI

GTVNSQGALPGMVWQNRDVYLQGPIWAKIPHTDGN

FHPSPLMGGFGLKHPPPQILIKNTPVPADPPTTFN

QSKLNSFITQYSTGQVSVEIEWELQKENSKRWNPE

IQYTSNYYKSTSVDFAVNTEGVYSEPRPIGTRYLT

RNL
```

```
Wild-type AAV9 amino acid sequence:
                                (SEQ ID NO: 8)
MAADGYLPDWLEDNLSEGIREWWALKPGAPQPKAN

QQHQDNARGLVLPGYKYLGPGNGLDKGEPVNAADA

AALEHDKAYDQQLKAGDNPYLKYNHADAEFQERLK

EDTSFGGNLGRAVFQAKKRLLEPLGLVEEAAKTAP

GKKRPVEQSPQEPDSSAGIGKSGAQPAKKRLNFGQ

TGDTESVPDPQPIGEPPAAPSGVGSLTMASGGGAP

VADNNEGADGVGSSSGNWHCDSQWLGDRVITTSTR

TWALPTYNNHLYKQISNSTSGGSSNDNAYFGYSTP

WGYFDFNRFHCHFSPRDWQRLINNNWGFRPKRLNF

KLFNIQVKEVTDNNGVKTIANNLTSTVQVFTDSDY

QLPYVLGSAHEGCLPPFPADVFMIPQYGYLTLNDG

SQAVGRSSFYCLEYFPSQMLRTGNNFQFSYEFENV

PFHSSYAHSQSLDRLMNPLIDQYLYYLSKTINGSG
```

```
                              -continued
QNQQTLKFSVAGPSNMAVQGRNYIPGPSYRQQRVS

TTVTQNNNSEFAWPGASSWALNGRNSLMNPGPAMA

SHKEGEDRFFPLSGSLIFGKQGTGRDNVDADKVMI

TNEEEIKTTNPVATESYGQVATNHQSAQAQAQTGW

VQNQGILPGMVWQDRDVYLQGPIWAKIPHTDGNFH

PSPLMGGFGMKHPPPQILIKNTPVPADPPTAFNKD

KLNSFITQYSTGQVSVEIEWELQKENSKRWNPEIQ

YTSNYYKSNNVEFAVNTEGVYSEPRPIGTRYLTRN

L
```

```
AAVrh10 amino acid sequence:
                                (SEQ ID NO: 9)
MAADGYLPDWLEDNLSEGIREWWDLKPGAPKPKAN

QQKQDDGRGLVLPGYKYLGPFNGLDKGEPVNAADA

AALEHDKAYDQQLKAGDNPYLRYNHADAEFQERLQ

EDTSFGGNLGRAVFQAKKRVLEPLGLVEEGAKTAP

GKKRPVEPSPQRSPDSSTGIGKKGQQPAKKRLNFG

QTGDSESVPDPQPIGEPPAGPSGLGSGTMAAGGGA

PMADNNEGADGVGSSSGNWHCDSTWLGDRVITTST

RTWALPTYNNHLYKQISNGTSGGSTNDNTYFGYST

PWGYFDFNRFHCHFSPRDWQRLINNNWGFRPKRLN

FKLFNIQVKEVTQNEGTKTIANNLTSTIQVFTDSE

YQLPYVLGSAHQGCLPPFPADVFMIPQYGYLTLNN

GSQAVGRSSFYCLEYFPSQMLRTGNNFEFSYQFED

VPFHSSYAHSQSLDRLMNPLIDQYLYYLSRTQSTG

GTAGTQQLLFSQAGPNNMSAQAKNWLPGPCYRQQR

VSTTLSQNNNSNFAWTGATKYHLNGRDSLVNPGVA

MATHKDDEERFFPSSGVLMFGKQGAGKDNVDYSSV

MLTSEEEIKTTNPVATEQYGVVADNLQQQNAAPIV

GAVNSQGALPGMVWQNRDVYLQGPIWAKIPHTDGN

FHPSPLMGGFGLKHPPPQILIKNTPVPADPPTTFS

QAKLASFITQYSTGQVSVEIEWELQKENSKRWNPE

IQYTSNYYKSTNVDFAVNTDGTYSEPRPIGTRYLT

RNL
```

```
AAVrh74 amino acid sequence:
                                (SEQ ID NO: 10)
MAADGYLPDWLEDNLSEGIREWWDLKPGAPKPKAN

QQKQDNGRGLVLPGYKYLGPFNGLDKGEPVNAADA

AALEHDKAYDQQLQAGDNPYLRYNHADAEFQERLQ

EDTSFGGNLGRAVFQAKKRVLEPLGLVESPVKTAP

GKKRPVEPSPQRSPDSSTGIGKKGQQPAKKRLNFG

QTGDSESVPDPQPIGEPPAGPSGLGSGTMAAGGGA

PMADNNEGADGVGSSSGNWHCDSTWLGDRVITTST

RTWALPTYNNHLYKQISNGTSGGSTNDNTYFGYST
```

-continued

PWGYFDFNRFHCHFSPRDWQRLINNNWGFRPKRLN

FKLFNIQVKEVTQNEGTKTIANNLTSTIQVFTDSE

YQLPYVLGSAHQGCLPPFPADVFMIPQYGYLTLNN

GSQAVGRSSFYCLEYFPSQMLRTGNNFEFSYNFED

VPFHSSYAHSQSLDRLMNPLIDQYLYYLSRTQSTG

GTAGTQQLLFSQAGPNNMSAQAKNWLPGPCYRQQR

VSTTLSQNNNSNFAWTGATKYHLNGRDSLVNPGVA

MATHKDDEERFFPSSGVLMFGKQGAGKDNVDYSSV

MLTSEEEIKTTNPVATEQYGVVADNLQQQNAAPIV

GAVNSQGALPGMVWQNRDVYLQGPIWAKIPHTDGN

FHPSPLMGGFGLKHPPPQILIKNTPVPADPPTTFT

KAKLASFITQYSTGQVSVEIEWELQKENSKRWNPE

IQYTSNYYKSTNVDFAVNTEGTYSEPRPIGTRYLT

RNL

AAVanc80L65 amino acid sequence:
                        (SEQ ID NO: 32)
MAADGYLPDWLEDNLSEGIREWWDLKPGAPKPKAN

QQKQDDGRGLVLPGYKYLGPFNGLDKGEPVNAADA

AALEHDKAYDQQLKAGDNPYLRYNHADAEFQERLQ

EDTSFGGNLGRAVFQAKKRVLEPLGLVEEGAKTAP

GKKRPVEQSPQEPDSSSGIGKKGQQPARKRLNFGQ

TGDSESVPDPQPLGEPPAAPSGVGSNTMAAGGGAP

MADNNEGADGVGNASGNWHCDSTWLGDRVITTSTR

TWALPTYNNHLYKQISSQSGGSTNDNTYFGYSTPW

GYFDFNRFHCHFSPRDWQRLINNNWGFRPKKLNFK

LFNIQVKEVTTNDGTTTIANNLTSTVQVFTDSEYQ

LPYVLGSAHQGCLPPFPADVFMIPQYGYLTLNNGS

QAVGRSSFYCLEYFPSQMLRTGNNFQFSYTFEDVP

FHSSYAHSQSLDRLMNPLIDQYLYYLSRTQTTSGT

AGNRTLQFSQAGPSSMANQAKNWLPGPCYRQQRVS

KTTNQNNNSNFAWTGATKYHLNGRDSLVNPGPAMA

THKDDEDKFFPMSGVLIFGKQGAGNSNVDLDNVMI

TNEEEIKTTNPVATEEYGTVATNLQSANTAPATGT

VNSQGALPGMVWQDRDVYLQGPIWAKIPHTDGHFH

PSPLMGGFGLKHPPPQILIKNTPVPANPPTTFSPA

KFASFITQYSTGQVSVEIEWELQKENSKRWNPEIQ

YTSNYNKSTNVDFAVDTNGVYSEPRPIGTRYLTRN

L

Variant Recombinant AAV8 Capsid Proteins

Provided herein are nucleic acids that encode any one of the variant rAAV capsid proteins disclosed herein. In some embodiments, a plasmid comprises a nucleic acid encoding a variant rAAV capsid protein.

Some non-limiting examples of nucleic acids encoding variant AAV capsid proteins are provided in Table 1. These variants are referred to as SL1.2 (encoded by SEQ ID NO: 1), SL1.2L (encoded by SEQ ID NO: 14), SL1.2B (encoded by SEQ ID NO: 20), SL1.2LB (encoded by SEQ ID NO: 26), SL2 (encoded by SEQ ID NO: 3), SL2L (encoded by SEQ ID NO: 16), SL2B (encoded by SEQ ID NO: 22), SL2LB (encoded by SEQ ID NO: 28), SL3 (encoded by SEQ ID NO: 5), SL3L (encoded by SEQ ID NO: 18), SL3B (encoded by SEQ ID NO: 24), and SL2LB (encoded by SEQ ID NO: 28).

The tissue tropism and transduction efficiency of AAV particles is determined by the nature of amino acid residues exposed at the surface of the capsid (Wu et al., J Virol. 2006, 80(22):11393-7). Therefore, manipulating the amino acids of the capsid proteins provides an opportunity to fine tune the tissue tropism of the particle and also improve transduction efficiency. However, certain manipulations, e.g., substitutions of amino acids, of the capsid protein can cause it to misfold or not form a capsid at all.

Disclosed herein are rAAV variants with increased transduction efficiency compared to wild-type AAV. In some embodiments, transduction efficiency is increased by removing phosphorylation sites that decrease the efficiency of AAV8. SL1.2, disclosed herein, is an rAAV8 variant with sequence modifications to disrupt phosphorylation. Also disclosed herein are rAAV variants that alter tissue tropism compared to wild-type AAV.

In some embodiments, the rAAV variants disclosed herein have increased transduction efficiency in and/or tropism for skeletal muscle compared to wild-type AAV. In some embodiments, the rAAV variants disclosed herein have increased transduction efficiency in and/or tropism for cardiac tissue compared to wild-type AAV. In some embodiments, the rAAV variants disclosed herein have increased transduction efficiency in and/or tropism for tissues of the central nervous system compared to wild-type AAV. In some embodiments, the rAAV variants disclosed herein have increased transduction efficiency in and/or tropism to cardiac tissue but without enhanced transduction in or tropism to CNS tissue. In some embodiments, the rAAV variants disclosed herein have increased transduction efficiency in, and/or tropism to, CNS tissue but without enhanced transduction in, or tropism to, cardiac tissue.

It is therefore useful to use the rAAV variants disclosed herein to deliver a gene to CNS, cardiac and/or skeletal muscle tissue, for example, to treat someone who has a disease or condition of that tissue.

Accordingly, provided herein are rAAV capsid proteins comprising changes (e.g., substitutions), relative to the wild-type AAV8 sequence (e.g., as set forth in SEQ ID NO: 7). In some embodiments, an amino acid substitution in any one of the variant AAV capsid proteins disclosed herein lies in a variable region. In some embodiments, one or more amino acid substitutions fall within recognized variable regions or exposed loops within the AAV capsid sequence. In some embodiments, all amino acid substitutions fall within recognized variable regions or exposed loops within the AAV capsid sequence. It should be understood that any positioning of an amino acid as described herein is with respect to the sequence of the wild-type AAV8 sequence as set forth in SEQ ID NO: 7.

Some non-limiting examples of variant AAV capsid proteins are provided in Table 1. These variants are referred to as SL1.2 (SEQ ID NO: 11), SL1.2L (SEQ ID NO: 15), SL1.2B (SEQ ID NO: 21), SL1.2LB (SEQ ID NO: 26), SL2 (SEQ ID NO: 12), SL2L (SEQ ID NO: 17), SL2B (SEQ ID NO: 23), SL2LB (SEQ ID NO: 28), SL3 (SEQ ID NO: 13), SL3L (SEQ ID NO: 19), SL3B (SEQ ID NO: 25), and SL2LB (SEQ ID NO: 31).

TABLE 1

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Variant | SEQ ID NO | Nucleic Acid Sequence | SEQ ID NO | Amino Acid Sequence |
|---|---|---|---|---|
| SL1.2 | SEQ ID NO: 1 | atggctgccgatggt tatcttccagattgg ctcgaggacaacctc tctgagggcattcgc gagtggtgggcgctg aaacctggagccccg aagcccaaagccaac cagcaaaagcaggac gacggccggggtctg gtgcttcctggctac aagtacctcggaccc ttcaacggactcgac aagggggagcccgtc aacgcggcggacgca gcggccctcgagcac gacaaggcctacgac cagcagctgcaggcg ggtgacaatccgtac ctgcggtataaccac gccgacgccgagttt caggagcgtctgcaa gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcaccc cagcgttctccagac tcctctGCGggcatc ggcaagTCGggcTCA cagcccgccAAAaaa agactcaattttggt cagactggcgacACA gagtcagttccagac cctcaacctATCgga gaacctccagcagcg ccctctggtgtggga cctaatacaatggct gcaggcggtggcgca ccaatggcagacaat aacgaaggcgccgac ggagtgggtagttcc tcgggaaattggcat tgcgattccacatgg ctgggcgacagagtc atcaccaccagcacc cgaacctgggccctg cccacctacaacaac cacctctacaagcaa atctccaacgggaca tcgggaggagccacc aacgacaacacctac ttcggctacagcacc ccctggggggtatttt gactttaacagattc cactgccacttttca ccacgtgactggcag cgactcatcaacaac aactggggattccgg cccaagagactcagc | SEQ ID NO: 11 | MAADGYLPDWLEDNL SEGIREWWALKPGAP KPKANQQKQDDGRGL VLPGYKYLGPFNGLD KGEPVNAADAAALEH DKAYDQQLQAGDNPY LRYNHADAEFQERLQ EDTSFGGNLGRAVFQ AKKRVLEPLGLVEEG AKTAPGKKRPVEPSP QRSPDSSAGIGKSGS QPAKKRLNFGQTGDT ESVPDPQPIGEPPAA PSGVGPNTMAAGGGA PMADNNEGADGVGSS SGNWHCDSTWLGDRV ITTSTRTWALPTYNN HLYKQISNGTSGGAT NDNTYFGYSTPWGYF DFNRFHCHFSPRDWQ RLINNNWGFRPKRLS FKLFNIQVKEVTQNE GTKTIANNLTSTIQV FTDSEYQLPYVLGSA HQGCLPPFPADVFMI PQYGYLTLNNGSQAV GRSSFYCLEYFPSQM LRTGNNFQFTYQFED VPFHSSYAHSQSLDR LMNPLIDQYLYFLSR TQTTGGTANTQQLLF SQGGPNTMANQAKNW LPGPCYRQQRVSTVT GQNNNSNFAWTAGTK YHLNGRNSLANPGIA MATHKDDEERFFPSN GILIFGKQNAARDNA DYSKVMLTSEEEIKT TNPVATEEYGIVADN LQQQNAAPQIGTVNS QGALPGMVWQNRDVY LQGPIWAKIPHTDGN FHPSPLMGGFGLKHP PPQILIKNTPVPADP PTTFNQSKLNSFITQ YSTGQVSVEIEWELQ KENSKRWNPEIQYTS NYYKSTSVDFAVNTE GVYSEPRPIGTRFLT RNL |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Variant | SEQ ID NO | Nucleic Acid Sequence | SEQ ID NO | Amino Acid Sequence |
|---|---|---|---|---|
| | | ttcaagctcttcaac atccaggtcaaggag gtcacgcagaatgaa ggcaccaagaccatc gccaataacctcacc agcaccatccaggtg tttacggactcggag taccagctgccgtac gttctcggctctgcc caccagggctgcctg cctccgttcccggcg gacgtgttcatgatt ccccagtacggctac ctaacactcaacaac ggtagtcaggccgtg ggacgctcctccttc tactgcctggaatac tttccttcgcagatg ctgagaaccggcaac aacttccagtttact tacCAGttcgaggac gtgccttttccacagc agctacgcccacagc cagagcttggaccgg ctgatgaatcctctg attgaccagtacctg tacTTCttgtctcgg actcaaacaacagga ggcacggcaaatacg cagCAGctgCTAttc agccaaggtgggcct aatacaatggccaat caggcaaagaactgg ctgccaggacccgct taccgccaacaacgc gtctcaacgGTAacc gggcaaaacaacaat agcaactttgcctgg actgctgggaccaaa taccatctgaatgga agaaattcattggct aatcctggcatcgct atggcaacacacaaa gacgacgaggagcgt ttttttcccagtaac gggatcctgatttt ggcaaacaaaatgct gccagagacaatgcg gattacagcAAAgtc atgctcaccagcgag gaagaaatcaaaact actaaccctgtggct acagaggaatacggt atcgtggcagataac ttgcagcagcaaaac GCCgctcctcaaatt ggaactgtcaacagc caggggggccttaccc ggtatgtctgtggcag aaccgggacgtgtac ctgcagggtcccatc tgggccaagattcct cacacggacggcaac ttccaccgtctccg ctgatgggcggcttt ggcctgaaacatcct ccgcctcagatcctg atcaagaacacgcct | | |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | gtacctgcggatcct | | |
| | | ccgaccaccttcaac | | |
| | | cagtcaaagctgaac | | |
| | | tctttcatcacgcaa | | |
| | | tacagcaccggacag | | |
| | | gtcagcgtggaaatt | | |
| | | gaatgggagctgcag | | |
| | | aaggaaaacagcaag | | |
| | | cgctggaaccccgag | | |
| | | atccagtacacctcc | | |
| | | aactactacaaatct | | |
| | | acaagtgtggacttt | | |
| | | gctgttaatacagaa | | |
| | | ggcgtgtactctgaa | | |
| | | ccccgcccattggc | | |
| | | acccgtTTCctcacc | | |
| | | cgtaatctgtaa | | |
| SL1.2L | SEQ ID NO: 14 | atggctgccgatggt tatcttccagattgg ctcgaggacaacctc tctgagggcattcgc gagtggtgggcgctg aaacctggagccccg aagcccaaagccaac cagcaaaagcaggac gacggccggggtctg gtgcttcctggctac aagtacctcggaccc ttcaacggactcgac aaggggagcccgtc aacgcggcggacgca gcggccctcgagcac gacaaggcctacgac cagcagctgcaggcg ggtgacaatccgtac ctgcggtataaccac gccgacgccgagttt caggagcgtctgcaa gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcaccc cagcgttctccagac tcctctGCGggcatc ggcaagTCGggcTCA cagcccgccAAAaaa agactcaattttggt cagactggcgacACA gagtcagttccagac cctcaacctATCgga gaacctccagcagcg ccctctggtgtggga cctaatacaatggct gcaggcggtggcgca ccaatggcagacaat aacgaaggcgccgac ggagtgggtagttcc tcgggaaattggcat tgcgattccacatgg ctgggcgacagagtc atcaccaccagcacc cgaacctgggccctg | SEQ ID NO: 15 | MAADGYLPDWLEDNL SEGIREWWALKPGAP KPKANQQKQDDGRGL VLPGYKYLGPFNGLD KGEPVNAADAAALEH DKAYDQQLQAGDNPY LRYNHADAEFQERLQ EDTSFGGNLGRAVFQ AKKRVLEPLGLVEEG AKTAPGKKRPVEPSP QRSPDSSAGIGKSGS QPAKKRLNFGQTGDT ESVPDPQPIGEPPAA PSGVGPNTMAAGGGA PMADNNEGADGVGSS SGNWHCDSTWLGDRV ITTSTRTWALPTYNN HLYKQISNGTSGGAT NDNTYFGYSTPWGYF DFNRFHCHFSPRDWQ RLINNNWGFRPKRLS FKLFNIQVKEVTQNE GTKTIANNLTSTIQV FTDSEYQLPYVLGSA HQGCLPPFPADVFMI PQYGYLTLNNGSQAG RSSFYCLEYFPSQML RTGNNFQFTYQFEDV PFHSSYAHSQSLDRL MNPLIDQYLYFLSRT QTTGGTANTQQLLFS QGGPNTMANQAKNWL PGPCYRQQRVSTVTG QNNISNFAWTAGTKY HLNGRNSLANPGIAM ATHKDDEERFFPSNG ILIFGKQNAARDNAD YSKVMLTSEEEIKTT NPVATEEYGIVADNL QQQNAAPQIGTVNSQ GALPGMVWQNRDVYL QGPIWAKIPHTDGNF HPSPLMGGFGLKHPP PQILIKNTPVPADPP TTFNQSKLNSFITQY STGQVSVEIEWELQK ENSKRWNPEIQYTSN YYKSTSVDFAVNTEG VYSEPRPIGTRFLTR NL |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | cccacctacaacaac | | |
| | | cacctctacaagcaa | | |
| | | atctccaacgggaca | | |
| | | tcgggaggagccacc | | |
| | | aacgacaacacctac | | |
| | | ttcggctacagcacc | | |
| | | ccctggggggtatttt | | |
| | | gactttaacagattc | | |
| | | cactgccactttttca | | |
| | | ccacgtgactggcag | | |
| | | cgactcatcaacaac | | |
| | | aactggggattccgg | | |
| | | cccaagagactcagc | | |
| | | ttcaagctcttcaac | | |
| | | atccaggtcaaggag | | |
| | | gtcacgcagaatgaa | | |
| | | ggcaccaagaccatc | | |
| | | gccaataacctcacc | | |
| | | agcaccatccaggtg | | |
| | | tttacggactcggag | | |
| | | taccagctgccgtac | | |
| | | gttctcggctctgcc | | |
| | | caccagggctgcctg | | |
| | | cctccgttcccggcg | | |
| | | gacgtgttcatgatt | | |
| | | ccccagtacggctac | | |
| | | ctaacactcaacaac | | |
| | | ggtagtcaggccgtg | | |
| | | ggacgctcctccttc | | |
| | | tactgcctggaatac | | |
| | | tttccttcgcagatg | | |
| | | ctgagaaccggcaac | | |
| | | aacttccagtttact | | |
| | | tacCAGttcagggac | | |
| | | gtgcctttccacagc | | |
| | | agctacgcccacagc | | |
| | | cagagcttggaccgg | | |
| | | ctgatgaatcctctg | | |
| | | attgaccagtacctg | | |
| | | tacTTCttgtctcgg | | |
| | | actcaaacaacagga | | |
| | | ggcacggcaaatacg | | |
| | | cagCAGctgCTAttc | | |
| | | agccaaggtgggcct | | |
| | | aatacaatggccaat | | |
| | | caggcaaagaactgg | | |
| | | ctgccaggaccaacgc | | |
| | | taccgccaacaacgc | | |
| | | gtctcaacgGTAacc | | |
| | | gggcaaaacaacATC | | |
| | | agcaactttgcctggac | | |
| | | actgctgggaccaaa | | |
| | | taccatctgaatgga | | |
| | | agaaattcattggct | | |
| | | aatcctgtggtggcc | | |
| | | atggcaacacacaaa | | |
| | | gacgacgaggagcgt | | |
| | | ttttttcccagtaac | | |
| | | gggatcctgattttt | | |
| | | ggcaaacaaaatgct | | |
| | | gccagagacaatgcg | | |
| | | gattacagcAAAgtc | | |
| | | atgctcaccagcgag | | |
| | | gaagaaatcaaaacc | | |
| | | actaaccctgtggct | | |
| | | acagaggaatacggt | | |
| | | atcgtggcagataac | | |
| | | ttgcagcagcaaaac | | |

| 15 | 16 |
|---|---|

TABLE 1-continued | TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | GCCgctcctcaaatt | | |
| | | ggaactgtcaacagc | | |
| | | caggggccttaccc | | |
| | | ggtatggtctggcag | | |
| | | aaccgggacgtgtac | | |
| | | ctgcagggtcccatc | | |
| | | tgggccaagattcct | | |
| | | cacacggacggcaac | | |
| | | ttccacccgtctccg | | |
| | | ctgatgggcggcttt | | |
| | | ggcctgaaacatcct | | |
| | | ccgcctcagatcctg | | |
| | | atcaagaacacgcct | | |
| | | gtacctgcggatcct | | |
| | | ccgaccaccttcaac | | |
| | | cagtcaaagctgaac | | |
| | | tctttcatcacgcaa | | |
| | | tacagcaccggacag | | |
| | | gtcagcgtggaaatt | | |
| | | gaatgggagctgcag | | |
| | | aaggaaaacagcaag | | |
| | | cgctggaaccccgag | | |
| | | atccagtacacctcc | | |
| | | aactactacaaatct | | |
| | | acaagtgtggacttt | | |
| | | gctgttaatacagaa | | |
| | | ggcgtgtactctgaa | | |
| | | ccccgcccattggc | | |
| | | acccgtTTCctcacc | | |
| | | cgtaatctgtaa | | |
| SL1.2B | SEQ ID NO: 20 | Atggctgccgatggt tatcttccagattgg ctcgaggacaacctc tctgagggcattcgc gagtggtgggcgctg aaacctggagccccg aagcccaaagccaac cagcaaaagcaggac gacggccggggtctg gtgcttcctggctac aagtacctcggaccc ttcaacggactcgac aaggggagcccgtc aacgcggcggacgca gcggccctcgagcac gacaaggcctacgac cagcagctgcaggcg ggtgacaatccgtac ctgcggtataaccac gccgacgccgagttt caggagcgtctgcaa gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcaccc cagcgttctccagac tcctctGCGggcatc ggcaagTCGggcTCA cagcccgccAAAaaa agactcaattttggt cagactggcgacACA gagtcagttccagac | SEQ ID NO: 21 | MAADGYLPDWLEDNL SEGIREWWALKPGAP KPKANQQKQDDGRGL VLPGYKYLGPFNGLD KGEPVNAADAAALEH DKAYDQQLQAGDNPY LRYNHADAEFQERLQ EDTSFGGNLGRAVFQ AKKRVLEPLGLVEEG AKTAPGKKRPVEPSP QRSPDSSAGIGKSGS QPAKKRLNFGQTGDT ESVPDPQPIGEPPAA PSGVGPNTMAAGGGA PMADNNEGADGVGSS SGNWHCDSTWLGDRV ITTSTRTWALPTYNN HLYKQISSASTG_AS NDNHYFGYSTPWGYF DFNRFHCHFSPRDWQ RLINNNWGFRPKRLS FKLFNIQVKEVTQNE GTKTIANNLTSTIQV FTDSEYQLPYVLGSA HQGCLPPFPADVFMI PQYGYLTLNNGSQAV GRSSFYCLEYFPSQM LRTGNNFQFTYQFED VPFHSSYAHSQSLDR LMNPLIDQYLYFLSR TQTTGGTANTQQLLF SQGGPNTMANQAKNW LPGPCYRQQRVSTVT GQNNNSNFAWTAGTK YHLNGRNSLANPGIA MATHKDDEERFFPSN GILIFGKQNAARDNA |
| | | | | DYSKVMLTSEEEIKT |
| | | cctcaacctATCgga | | TNPVATEEYGIVADN |
| | | gaacctccagcagcg | | LQQQNAAPQIGTVNS |
| | | ccctctggtgtggga | | QGALPGMVWQNRDVY |
| | | cctaatacaatggct | | LQGPIWAKIPHTDGN |
| | | gcaggcggtggcgca | | FHPSPLMGGFGLKHP |
| | | ccaatggcagacaat | | PPQILIKNTPVPADP |
| | | aacgaaggcgccgac | | PTTFNQSKLNSFITQ |
| | | ggagtgggtagttcc | | YSTGQVSVEIEWELQ |
| | | tcgggaaattggcat | | KENSKRWNPEIQYTS |
| | | tgcgattccacatgg | | NYYKSTSVDFAVNTE |
| | | ctgggcgacagagtc | | GVYSEPRPIGTRFLT |
| | | atcaccaccagcacc | | RNL |
| | | cgaacctgggccctg | | |
| | | cccacctacaacaac | | |
| | | cacctctacaagcaa | | |
| | | atctccTCAGCATCC | | |
| | | ACAgga_gccAGTaa | | |
| | | cgacaacCATtactt | | |
| | | cggctacagcacccc | | |
| | | ctgggggtattttga | | |
| | | ctttaacagattcca | | |
| | | ctgccactttcacc | | |
| | | acgtgactggcagcg | | |
| | | actcatcaacaacaa | | |
| | | ctgggggattccggcc | | |
| | | caagagactcagctt | | |
| | | caagctcttcaacat | | |
| | | ccaggtcaaggaggt | | |
| | | cacgcagaatgaagg | | |
| | | caccaagaccatcgc | | |
| | | caataacctcaccag | | |
| | | caccatccaggtgtt | | |
| | | tacggactcggagta | | |
| | | ccagctgacgtacgt | | |
| | | tctcggctctgccca | | |
| | | ccagggctgcctgcc | | |
| | | tccgttcccggcgga | | |
| | | cgtgttcatgattcc | | |
| | | ccagtacgctacct | | |
| | | aacactcaacaacgg | | |
| | | tagtcaggccgtggg | | |
| | | acgctcctccttcta | | |
| | | ctgcctggaatactt | | |
| | | tccttcgcagatgct | | |
| | | gagaaccggcaacaa | | |
| | | cttccagtttactta | | |
| | | cCAGttcgacagt | | |
| | | gcctttccacagcag | | |
| | | ctacgcccacagcca | | |
| | | gagcttggaccggct | | |
| | | gatgaatcctctgat | | |
| | | tgaccagtacctgta | | |
| | | cTTCttgtctcggac | | |
| | | tcaaacaacaggagg | | |
| | | cacggcaaatacgca | | |
| | | gCAGctgCTAttcag | | |
| | | ccaaggtgggcctaa | | |
| | | tacaatggccaatca | | |
| | | ggcaaagaactggct | | |
| | | gccaggaccctgtta | | |
| | | ccgccaacaacgcgt | | |
| | | ctcaacgTAaccgg | | |
| | | gcaaaacaacaatag | | |
| | | caactttgcctggac | | |
| | | tgctgggaccaaata | | |
| | | ccatctgaatggaag | | |
| | | aaattcattggctaa | | |
| | | tcctggcatcgctat | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | ggcaacacacaaaga | | |
| | | cgacgaggagcgttt | | |
| | | ttttcccagtaacgg | | |
| | | gatcctgattttttgg | | |
| | | caaacaaaatgctgc | | |
| | | cagagacaatgcgga | | |
| | | ttacagcAAAgtcat | | |
| | | gctcaccagcgagga | | |
| | | agaaatcaaaaccac | | |
| | | taaccctgtggctac | | |
| | | agaggaatacggtat | | |
| | | cgtggcagataactt | | |
| | | gcagcagcaaaacGC | | |
| | | Cgctcctcaaattgg | | |
| | | aactgtcaacagcca | | |
| | | gggggccttacccgg | | |
| | | tatggtctggcagaa | | |
| | | ccgggacgtgtacct | | |
| | | gcagggtcccatctg | | |
| | | ggccaagattcctca | | |
| | | cacggacggcaactt | | |
| | | ccacccgtctccgct | | |
| | | gatgggcggctttgg | | |
| | | cctgaaacatcctcc | | |
| | | gcctcagatcctgat | | |
| | | caagaacacgcctgt | | |
| | | acctgcggatcctcc | | |
| | | gaccaccttcaacca | | |
| | | gtcaaagctgaactc | | |
| | | tttcatcacgcaata | | |
| | | cagcaccggacaggt | | |
| | | cagcgtggaaattga | | |
| | | atgggagctgcagaa | | |
| | | ggaaaacagcaagcg | | |
| | | ctggaaccccgagat | | |
| | | ccagtacacctccaa | | |
| | | ctactacaaatctac | | |
| | | aagtgtggactttgc | | |
| | | tgttaatacagaagg | | |
| | | cgtgtactctgaacc | | |
| | | ccgccccattggcac | | |
| | | ccgtTTCctcacccg | | |
| | | taatctgtaa | | |
| SL1.B2L | SEQ ID NO: 26 | Atggctgccgatggt tatcttccagattgg ctcgaggacaacctc tctgagggcattctt gcgagtggtgggcgc tgaaacctggagccc cgaagcccaaagcca accagcaaaattgca ggacgacggccgggg tctggtgcttcctgg ctacaagtacctcgg acccttcaattcgga ctcgacaaggggggag cccgtcaacgcggcg gacgcagcgccctc gagcattcgacaagg cctacgaccagcagc tgcaggcgggtgaca atccgtacctcggct atattaccacgccga cgccgagtttcagga cgcctgcaagaaga tacgtcttttggggg cattacctcgggcga | SEQ ID NO: 27 | MAADGYLPDWLEDNL SEGIREWWALKPGAP KPKANQQKQDDGRGL VLPGYKYLGPFNGLD KGEPVNAADAAALEH DKAYDQQLQAGDNPY LRYNHADAEFQERLQ EDTSFGGNLGRAVFQ AKKRVLEPLGLVEEG AKTAPGKKRPVEPSP QRSPDSSAGIGKSGS QPAKKRLNFGQTGDT ESVPDPQPIGEPPAA PSGVGPNTMAAGGGA PMADNNEGADGVGSS SGNWHCDSTWLGDRV ITTSTRTWALPTYNN HLYKQISSASTG_AS NDNHYFGYSTPWGYF DFNRFHCHFSPRDWQ RLINNNWGFRPKRLS FKLFNIQVKEVTQNE GTKTIANNLTSTIQV FTDSEYQLPYVLGSA |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | gcagtcttccaggcc | | HQGCLPPFPADVFMI |
| | | aagaagcgggttctc | | PQYGYLTLNNGSQAV |
| | | gaacctctcggtctg | | GRSSFYCLEYFPSQM |
| | | gttttgaggaaggcg | | LRTGNNFQFTYQFED |
| | | ctaagacggctcctg | | VPFHSSYAHSQSLDR |
| | | gaaagaagagaccct | | LMNPLIDQYLYFLSR |
| | | tagagccatcaccct | | TQTTGGTANTQQLLF |
| | | tcagcgttctccaga | | SQGGPNTMANQAKNW |
| | | ctcctctGCGggcat | | LPGPCYRQQRVSTVT |
| | | cggcaagTCGggcTC | | GQNNISNFAWTAGTK |
| | | AcagcccttgccAAA | | YHLNGRNSLANPGIA |
| | | aaaagactcaatttt | | MATHKDDEERFFPSN |
| | | ggtcagactggcgtg | | GILIFGKQNAARDNA |
| | | ACAgagtcagttcca | | DYSKVMLTSEEEIKT |
| | | gacttcctcaacctA | | TNPVATEEYGIVADN |
| | | TCggagaacctccag | | LQQQNAAPQIGTVNS |
| | | cagcgccctctggtg | | QGALPGMVWQNRDVY |
| | | tgggacctaatacaa | | LQGPIWAKIPHTDGN |
| | | tttggctgcaggcgg | | FHPSPLMGGFGLKHP |
| | | tggcgcaccaatggc | | PPQILIKNTPVPADP |
| | | agacaataacgaagg | | PTTFNQSKLNSFITQ |
| | | cgccgacggagtttg | | YSTGQVSVEIEWELQ |
| | | ggtagttcctcggga | | KENSKRWNPEIQYTS |
| | | aattggcattgcgat | | NYYKSTSVDFAVNTE |
| | | tccacatggctgggc | | GVYSEPRPIGTRFLT |
| | | gacagagtcatctta | | RNL |
| | | ccaccagcacccgaa | | |
| | | cctgggccctgccca | | |
| | | cctacaacaaccacc | | |
| | | tctacaagcattaat | | |
| | | ctccTCAGCATCCAC | | |
| | | Agga_gccAGTaacg | | |
| | | acaacCATtacttct | | |
| | | tggctacagcacccc | | |
| | | ctggggggtattttga | | |
| | | ctttaacagattcca | | |
| | | ctgccacttttcacc | | |
| | | attcgtgactggcca | | |
| | | cgactcatcaacaac | | |
| | | aactgggggattccgg | | |
| | | cccaagagactcagt | | |
| | | tcttcaagctcttca | | |
| | | acatccaggtcaagg | | |
| | | aggtcacgcagaatg | | |
| | | aaggcaccaagactt | | |
| | | catcgccaataacct | | |
| | | caccagcaccatcca | | |
| | | ggtgtttacggactc | | |
| | | ggagtaccagctgtt | | |
| | | ccgtacgttctcggc | | |
| | | tctgcccaccaggtgc | | |
| | | tgcctgcctccgttc | | |
| | | ccggcggacgtgttt | | |
| | | tcatgattcccccagt | | |
| | | acggctacctaacac | | |
| | | tcaacaacgtagtc | | |
| | | aggccgtgggacgtt | | |
| | | ctcctccttctactg | | |
| | | cctggaatactttcc | | |
| | | ttcgcagatgctgag | | |
| | | aaccggcaacaactt | | |
| | | ttccagtttacttac | | |
| | | CAGttcgaggacgtg | | |
| | | cctttccagcagcag | | |
| | | tacgcccacagccat | | |
| | | tgagcttggaccggc | | |
| | | tgatgaatcctctga | | |
| | | ttgaccagtacctgt | | |

19

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | acTTCttgtctcggt | | |
| | | tactcaaacaacagg | | |
| | | aggcacggcaaatac | | |
| | | gcagCAGctgCTAtt | | |
| | | cagccaagttgtggg | | |
| | | cctaatacaatggcc | | |
| | | aatcaggcaaagaac | | |
| | | tggctgccaggaccc | | |
| | | tgttaccttgccaac | | |
| | | aacgcgtctcaacgG | | |
| | | TAaccgggcaaaaca | | |
| | | acATTcagcaactttg | | |
| | | cctttggactgctgg | | |
| | | gaccaaataccatct | | |
| | | gaatggaagaaattc | | |
| | | attggctaatcctgg | | |
| | | catcgctatggcaac | | |
| | | acacaaagacgacga | | |
| | | ggagcgttttttttcc | | |
| | | cagtaacgggatcct | | |
| | | gttattttttggcaaa | | |
| | | caaaatgctgccaga | | |
| | | gacaatgcggattac | | |
| | | agcAAAgtcatgctc | | |
| | | ttaccagcgaggaag | | |
| | | aaatcaaaaccacta | | |
| | | accctgtggctacag | | |
| | | aggaatacggtatct | | |
| | | tgtggcagataactt | | |
| | | gcagcagcaaaacGC | | |
| | | Cgctcctcaaattgg | | |
| | | aactgtcaacagttc | | |
| | | cagggggccttaccc | | |
| | | ggtatggtctggcag | | |
| | | aaccgggacgtgtac | | |
| | | ctgcagggtcttcca | | |
| | | tctgggccaagattc | | |
| | | ctcacacggacggca | | |
| | | acttccacccgtctc | | |
| | | cgctgatgggttcgg | | |
| | | ctttggcctgaaaca | | |
| | | tcctccgcctcgat | | |
| | | cctgatcaagaacac | | |
| | | gcctgtacctgttcg | | |
| | | gatcctccgaccacc | | |
| | | ttcaaccagtcaaag | | |
| | | ctgaactcttttcatc | | |
| | | acgcaatacagctta | | |
| | | ccggacaggtcagcg | | |
| | | tggaaattgaatggg | | |
| | | agctgcagaaggaaa | | |
| | | acagcaagcttgctg | | |
| | | gaaccccgagatcca | | |
| | | gtacacctccaacta | | |
| | | ctacaaatctacaag | | |
| | | tgtggactttttgct | | |
| | | gttaatacagaaggc | | |
| | | gtgtactctgaaccc | | |
| | | cgccccattggcacc | | |
| | | cgtTTCctcttaccc | | |
| | | gtaatctgtaa | | |
| SL2 | SEQ ID NO: 3 | atggctgccgatggt tatcttccagattgg ctcgaggacaacctc tctgagggcattcgc gagtggtgggacttg aaacctggagccccg | SEQ ID NO: 12 | MAADGYLPDWLEDNL SEGIREWWDLKPGAP KPKANQQKQDNGRGL VLPGYKYLGPFNGLD KGEPVNAADAAALEH DKAYDQQLKAGDNPY |

20

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | aaacccaaagccaac | | LKYNHADAEFQERLQ |
| | | cagcaaaagcaggac | | EDTSFGGNLGRAVFQ |
| | | AACggccgggtgtctg | | AKKRVLEPLGLVEEG |
| | | gtgcttcctggctac | | AKTAPGKKRPVEPSP |
| | | aagtacctcggaccc | | QRSPDSSAGIGKSGA |
| | | ttcaacggactcgac | | QPAKKRLNFGQTGDS |
| | | aagggggagcccgtc | | ESVPDPQPIGEPPAG |
| | | aacgcggcggacgca | | PSGLGSNTMAAGGGA |
| | | gcggccctcgagcac | | PMADNNEGADGVGSA |
| | | gacaaggcctacgac | | SGNWHCDSTWLGDRV |
| | | cagcagctcaaagcg | | ITTSTRTWALPTYNN |
| | | ggtgacaatccgtac | | HLYKQISNSTSGGST |
| | | ctgAAGtataaccac | | NDNTYFGYSTPWGYF |
| | | gccgacgccgagttt | | DFNRFHCHFSPRDWQ |
| | | caggagcgtctgcaa | | RLINNNWGFRPKKLN |
| | | gaagatacgtctttt | | FKLFNIQVKEVTQNE |
| | | ggggggcaacctcggg | | GTKTIANNLTSTIQV |
| | | cgagcagtcttccag | | FTDSDYQLPYVLGSA |
| | | gccaagaagcgggtt | | HEGCLPPFPADVFMI |
| | | ctcgaacctctcggt | | PQYGYLTLNDGSQAV |
| | | ctggttgaggaaggc | | GRSSFYCLEYFPSQM |
| | | gctaagacggctcct | | LRTGNNFEFSYQFED |
| | | ggaaagaagagaccg | | VPFHSSYAHSQSLDR |
| | | gtagagccatcaccc | | LMNPLIDQYLYFLSR |
| | | cagcgttctccagac | | TQSTGGTAGTQQLLF |
| | | tcctctGCGggcatc | | SQAGPSNMSAQAKNW |
| | | ggcaagTCGggcGCA | | LPGPCYRQQRVSTVT |
| | | cagcccgcgaaaaag | | NQNNNSNFAWTGATK |
| | | agactcaactttggg | | YHLNGRDSLVNPGIA |
| | | cagactggcgactca | | MASHKEGEERFFPSS |
| | | gagtcagtgcccgac | | GILIFGKQGAGRDNV |
| | | cctcaaccaatcgga | | DYSKVMLTSEEEIKT |
| | | gaaccccccgcaggc | | TNPVATEQYGQVADN |
| | | ccctctggtctggga | | LQQQNAAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggcgccgac | | PPQILIKNTPVPADP |
| | | ggagtggggagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgacagagtc | | NYYKSTNVDFAVNTE |
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccaacAGCact | | |
| | | tcgggaggaagcacc | | |
| | | aacgcacaacacctac | | |
| | | ttcggctacagcacc | | |
| | | ccctggggggtatttt | | |
| | | gactttaacagaattc | | |
| | | cactgccacttctca | | |
| | | ccacgtgactggcag | | |
| | | cgactcatcaacaac | | |
| | | aactgggattccgg | | |
| | | cccaagAAActcaac | | |
| | | ttcaagctcttcaac | | |
| | | atccaggtcaaggag | | |
| | | gtcacgcagaatgaa | | |
| | | ggcaccaagaccatc | | |
| | | gccaataaccttacc | | |
| | | agcacgattcaggtc | | |
| | | tttacggactcgGAC | | |
| | | taccagctcccgtac | | |
| | | gtcctcggctctgcg | | |
| | | cacGAGggctgcctg | | |
| | | cctccgttcccggcg | | |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | gacgtcttcatgatt | | |
| | | cctcagtacgggtac | | |
| | | ctgactctgaacGAT | | |
| | | ggcagtcaggccgtg | | |
| | | ggccgttcctccttc | | |
| | | tactgcctggagtac | | |
| | | tttccttctcaaatg | | |
| | | ctgagaacgggcaac | | |
| | | aactttgagttcagc | | |
| | | taccagtttgaggac | | |
| | | gtgccttttcacagc | | |
| | | agctacgcgcacagc | | |
| | | caaagcctggaccgg | | |
| | | ctgatgaaccccctc | | |
| | | atcgaccagtacctg | | |
| | | tacTTCctgtctcgg | | |
| | | actcagtccacggga | | |
| | | ggtaccgcaggaact | | |
| | | cagcagttgctattt | | |
| | | tctcaggccgggcct | | |
| | | AGCaacatgtcggct | | |
| | | caggccaaaaactgg | | |
| | | ctacccgggccctgc | | |
| | | taccggcagcaacgc | | |
| | | gtctccacgGTAACC | | |
| | | AACcaaaataacaac | | |
| | | agcaactttgcctgg | | |
| | | accggtgccaccaag | | |
| | | tatcatctgaatggc | | |
| | | agagactctctggta | | |
| | | aatcccggtATCgct | | |
| | | atggcaAGCcacaag | | |
| | | GAAGGAgaagagcga | | |
| | | ttttttccgtccagc | | |
| | | ggaATCttaATTttt | | |
| | | gggaaacagggagct | | |
| | | ggaAGAgacaacgtg | | |
| | | gactatagcAAAgtt | | |
| | | atgctaaccagtgag | | |
| | | gaagaaattaaaacc | | |
| | | accaacccagtggcc | | |
| | | acagaacagtacggc | | |
| | | CAAgtggccgataac | | |
| | | ctgcaacagcaaaac | | |
| | | gccgctcctattgta | | |
| | | gggACTgtcaacagt | | |
| | | caaggagccttacct | | |
| | | ggcatggtctggcag | | |
| | | aaccgggacgtgtac | | |
| | | ctgcagggtcctatc | | |
| | | tgggccaagattcct | | |
| | | cacacggacggaaac | | |
| | | tttcatccctcgccg | | |
| | | ctgatgggaggcttt | | |
| | | ggactgaaacacccg | | |
| | | cctcctcagatcctg | | |
| | | attaagaatacacct | | |
| | | gttcccgcggatcct | | |
| | | ccaactaccttcagt | | |
| | | caagctaagctggcg | | |
| | | tcgttcatcacgcag | | |
| | | tacagcaccggacag | | |
| | | gtcagcgtggaaatt | | |
| | | gaatgggagctgcag | | |
| | | aaagaaaacagcaaa | | |
| | | cgctggaacccagag | | |
| | | attcaatacacttcc | | |
| | | aactactacaaatct | | |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | acaaatgtggacttt | | |
| | | gctgttaacacaGAA | | |
| | | ggcacttattctgag | | |
| | | cctcgccccatcggc | | |
| | | acccgtTTCctcacc | | |
| | | cgtaatctgtaa | | |
| SL2L | SEQ ID NO: 16 | atggctgccgatggt | SEQ ID NO: 17 | MAADGYLPDWLEDNL |
| | | tatcttccagattgg | | SEGIREWWDLKPGAP |
| | | ctcgaggacaacctc | | KPKANQQKQDNGRGL |
| | | tctgagggcattcgc | | VLPGYKYLGPFNGLD |
| | | gagtggtgggacttg | | KGEPVNAADAAALEH |
| | | aaacctggagccccg | | DKAYDQQLKAGDNPY |
| | | aaacccaaagccaac | | LKYNHADAEFQERLQ |
| | | cagcaaaagcaggac | | EDTSFGGNLGRAVFQ |
| | | AACggccgggggtctg | | AKKRVLEPLGLVEEG |
| | | gtgcttcctggctac | | AKTAPGKKRPVEPSP |
| | | aagtacctcggaccc | | QRSPDSSAGIGKSGA |
| | | ttcaacggactcgac | | QPAKKRLNFGQTGDS |
| | | aaggggggagcccgtc | | ESVPDPQPIGEPPAG |
| | | aacgcggcggacgca | | PSGLGSNTMAAGGGA |
| | | gcggccctcgacgac | | PMADNNEGADGVGSA |
| | | gacaaggcctacgac | | SGNWHCDSTWLGDRV |
| | | cagcagctcaaagcg | | ITTSTRTWALPTYNN |
| | | ggtgacaatccgtac | | HLYKQISNSTSGGST |
| | | ctgAAGtataaccac | | NDNTYFGYSTPWGYF |
| | | gccgacgccgagttt | | DFNRFHCHFSPRDWQ |
| | | caggagcgtctgcaa | | RLINNNWGFRPKKLN |
| | | gaagatacgtctttt | | FKLFNIQVKEVTQNE |
| | | gggggcaacctcggt | | GTKTIANNLTSTIQV |
| | | cgagcagtcttccag | | FTDSDYQLPYVLGSA |
| | | gccaagaagcgggtt | | HEGCLPPFPADVFMI |
| | | ctcgaacctctcggt | | PQYGYLTLNDGSQAV |
| | | ctggttaaggacttc | | GRSSFYCLEYFPSQM |
| | | gctaagacggctcct | | LRTGNNFEFSYQFED |
| | | ggaaagaagagaccg | | VPFHSSYAHSQSLDR |
| | | gtagagccatcaccc | | LMNPLIDQYLYFLSR |
| | | cagcgttctccagac | | TQSTGGTAGTQQLLF |
| | | tcctctGCGggcatc | | SQAGPSNMSAQAKNW |
| | | ggcaagTCGggcGCA | | LPGPCYRQQRVSTVT |
| | | cagcccgcgaaaaag | | NQNNISNFAWTGATK |
| | | agactcaactttggg | | YHLNGRDSLVNPGIA |
| | | cagactggcgactca | | MASHKEGEERFFPSS |
| | | gagtcagtgcccgac | | GILIFGKQGAGRDNV |
| | | cctcaaccaatcgga | | DYSKVMLTSEEEIKT |
| | | gaaccccccgcaggc | | TNPVATEQYGQVADN |
| | | ccctctggtctggga | | LQQQNAAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggccgccgac | | PPQILIKNTPVPADP |
| | | ggagtgggtagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgacagatc | | NYYKSTNVDFAVNTE |
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccaacAGCact | | |
| | | tcgggaggaagcacc | | |
| | | aacgacaacacctac | | |
| | | ttcggctacagcacc | | |
| | | ccctggggggtatttt | | |
| | | gactttaacagattc | | |
| | | cactgccacttctca | | |
| | | ccacgtgactggcag | | |
| | | cgactcatcaacaac | | |

23

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | aactgggattccgg | | |
| | | cccaagAAActcaac | | |
| | | ttcaagctcttcaac | | |
| | | atccaggtcaaggag | | |
| | | gtcacgcagaatgaa | | |
| | | ggcaccaagaccatc | | |
| | | gccaataaccttacc | | |
| | | agcacgattcaggtc | | |
| | | tttacggactcgGAC | | |
| | | taccagctcccgtac | | |
| | | gtcctcggctctgcg | | |
| | | cacGAGggctgcctg | | |
| | | cctccgttcccggcg | | |
| | | gacgtcttcatgatt | | |
| | | cctcagtacgggtac | | |
| | | ctgactctgaacGAT | | |
| | | ggcagtcaggccgtg | | |
| | | ggccgttcctccttc | | |
| | | tactgcctggagtac | | |
| | | tttccttctcaaatg | | |
| | | ctgagaacgggcaac | | |
| | | aactttgagttcagc | | |
| | | taccagtttgaggac | | |
| | | gtgccttttcacagc | | |
| | | agctacgcgcacagc | | |
| | | caaagcctggaccgg | | |
| | | ctgatgaaccccctc | | |
| | | atcgaccagtacctg | | |
| | | tacTTCctgtctcgg | | |
| | | actcagtccacggga | | |
| | | ggtaccgcaggaact | | |
| | | cagcagttgctattt | | |
| | | tctcaggccgggcct | | |
| | | AGCaacatgtcggct | | |
| | | caggccaaaaactgg | | |
| | | ctacccgggccctgc | | |
| | | taccggcagcaacgc | | |
| | | gtctccacgGTAACC | | |
| | | AACcaaaataacATC | | |
| | | agcaactttgcctgg | | |
| | | accggtgccaccaag | | |
| | | tatcatctgaatggc | | |
| | | agagactctctggta | | |
| | | aatcccggtATCgct | | |
| | | atggcaAGCcacaag | | |
| | | GAAGGAgaagagcga | | |
| | | ttttttccgtccagc | | |
| | | ggaATCttaATTttt | | |
| | | gggaaacagggagct | | |
| | | ggaAGAgacaacgtg | | |
| | | gactatagcAAAgtt | | |
| | | atgctaaccagtgag | | |
| | | gaagaaattaaaacc | | |
| | | accaacccagtggcc | | |
| | | acagaacagtacggc | | |
| | | CAAgtggccgataac | | |
| | | ctgcaacagcaaaac | | |
| | | gccgctcctattgta | | |
| | | gggACTgtcaacagt | | |
| | | caaggagccttacct | | |
| | | ggcatggtctggcag | | |
| | | aaccgggacgtgtac | | |
| | | ctgcagggtcctatc | | |
| | | tgggccaagattcct | | |
| | | cacacggacgaaac | | |
| | | tttcatccctcgccg | | |
| | | ctgatgggaggcttt | | |
| | | ggactgaaacacccg | | |

24

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Vari-ant | SEQ ID NO | Nucleic Acid Sequence | SEQ ID NO | Amino Acid Sequence |
|---|---|---|---|---|
| | | cctcctcagatcctg | | |
| | | ataagaatacacct | | |
| | | gttcccgcggatcct | | |
| | | ccaactaccttcagt | | |
| | | caagctaagctggcg | | |
| | | tcgttcatcacgcag | | |
| | | tacagcaccggacag | | |
| | | gtcagcgtggaaatt | | |
| | | gaatgggagctgcag | | |
| | | aaagaaaacagcaaa | | |
| | | cgctggaacccagag | | |
| | | attcaatacacttcc | | |
| | | aactactacaaatct | | |
| | | acaaatgtggacttt | | |
| | | gctgttaacacaGAA | | |
| | | ggcacttattctgag | | |
| | | cctcgcccccatcggc | | |
| | | acccgtTTCctcacc | | |
| | | cgtaatctgtaa | | |
| SL2B | SEQ ID NO: 22 | atggctgccgatggt | SEQ ID NO: 23 | MAADGYLPDWLEDNL |
| | | tatcttccagattgg | | SEGIREWWDLKPGAP |
| | | ctcgaggacaacctc | | KPKANQQKQDNGRGL |
| | | tctgagggcatCcgc | | VLPGYKYLGPFNGLD |
| | | gagtggtgggacttg | | KGEPVNAADAAALEH |
| | | aaacctggacccccg | | DKAYDQQLKAGDNPY |
| | | aaacccaaagccaac | | LKYNHADAEFQERLQ |
| | | cagcaaaagcaggac | | EDTSFGGNLGRAVFQ |
| | | AACggccggggtctg | | AKKRVLEPLGLVEEG |
| | | gtgcttcctggctac | | AKTAPGKKRPVEPSP |
| | | aagtacctcggaccc | | QRSPDSSAGIGKSGA |
| | | ttcaacggactcgac | | QPAKKRLNFGQTGDS |
| | | aaggggagcccgtc | | ESVPDPQPIGEPPAG |
| | | aacgcggcggacgca | | PSGLGSNTMAAGGGA |
| | | gcggccctcgagcac | | PMADNNEGADGVGSA |
| | | gacaaggcctacgac | | SGNWHCDSTWLGDRV |
| | | cagcagctcaaagcg | | ITTSTRTWALPTYNN |
| | | ggtgacaatccgtac | | HLYKQISSASTG_AS |
| | | ctgAAGtataaccac | | NDNHYFGYSTPWGYF |
| | | gccgacgccgagttt | | DFNRFHCHFSPRDWQ |
| | | caggagcgtctgcaa | | RLINNNWGFRPKKLN |
| | | gaagatacgtctttt | | FKLFNIQVKEVTQNE |
| | | gggggcaacctcggg | | GTKTIANNLTSTIQV |
| | | cgagcagtcttccag | | FTDSDYQLPYVLGSA |
| | | gccaagaagcgggtt | | HEGCLPPFPADVFMI |
| | | ctcgaacctctcggt | | PQYGYLTLNDGSQAV |
| | | ctggttgaggaaggc | | GRSSFYCLEYFPSQM |
| | | gctaagacggctcct | | LRTGNNFEFSYQFED |
| | | ggaaagaagagaccg | | VPFHSSYAHSQSLDR |
| | | gtagagccatcaccc | | LMNPLIDQYLYFLSR |
| | | cagcgttctccagac | | TQSTGGTAGTQQLLF |
| | | tcctctGCGggcatc | | SQAGPSNMSAQAKNW |
| | | ggcaagTCGgcGCA | | LPGPCYRQQRVSTVT |
| | | cagcccgcgaaaaag | | NQNNNSNFAWTGATK |
| | | agactcaactttggg | | YHLNGRDSLVNPGIA |
| | | cagactggcgactca | | MASHKEGEERFFPSS |
| | | gagtcagtgcccgac | | GILIFGKQGAGRDNV |
| | | cctcaaccaatcgga | | DYSKVMLTSEEEIKT |
| | | gaacccccgcaggc | | TNPVATEQYGQVADN |
| | | ccctctggtctggga | | LQQQNAAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggcgccgac | | PPQILIKNTPVPADP |
| | | ggagtgggtagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgcacagagtc | | NYYKSTNVDFAVNTE |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccTCAGCATCC | | |
| | | ACAgga_gccAGTaa | | |
| | | cgacaacCATtactt | | |
| | | cggctacagcacccc | | |
| | | ctgggggtattttga | | |
| | | ctttaacagattcca | | |
| | | ctgccacttctcacc | | |
| | | acgtgactggcagcg | | |
| | | actcatcaacaacaa | | |
| | | ctggggattccggcc | | |
| | | caagAAActcaactt | | |
| | | caagctcttcaacat | | |
| | | ccaggtcaaggaggt | | |
| | | cacgcagaatgaagg | | |
| | | caccaagaccatcgc | | |
| | | caataaccttaccag | | |
| | | cacgattcaggtctt | | |
| | | tacggactcgGACta | | |
| | | ccagctcccgtacgt | | |
| | | cctcggctctgcgca | | |
| | | cGAGggctgcctgcc | | |
| | | tccgttcccggcgga | | |
| | | cgtcttcatgattcc | | |
| | | tcagtacgggtacct | | |
| | | gactctgaacGATgg | | |
| | | cagtcaggccgtggg | | |
| | | ccgttcctccttcta | | |
| | | ctgcctggagtactt | | |
| | | tccttctcaaatgct | | |
| | | gagaacgggcaacaa | | |
| | | ctttgagttcagcta | | |
| | | ccagtttgaggacgt | | |
| | | gccttttcacagcag | | |
| | | ctacgcgcacagcca | | |
| | | aagcctggaccggct | | |
| | | gatgaaccccctcat | | |
| | | cgaccagtacctgta | | |
| | | cTTCctgtctcggac | | |
| | | tcagtccacgggagg | | |
| | | taccgcaggaactca | | |
| | | gcagttgctattttc | | |
| | | tcaggccgggcctAG | | |
| | | Caacatgtcggctca | | |
| | | ggccaaaaactggct | | |
| | | acccgggccctgcta | | |
| | | ccggcagcaacgcgt | | |
| | | ctccacgGTAACCAA | | |
| | | Ccaaaataacaatag | | |
| | | caactttgcctggac | | |
| | | cggtgccaccaagta | | |
| | | tcatctgaatggcag | | |
| | | agactctctggtaaa | | |
| | | tcccggtATCgctat | | |
| | | ggcaAGCcacaagGA | | |
| | | AGGAgaagagcgatt | | |
| | | ttttccgtccagcgg | | |
| | | aATCttaATTtttgg | | |
| | | gaaacaggagctgg | | |
| | | aAGAgacaacgtgga | | |
| | | ctatagcAAAgttat | | |
| | | gctaaccagtgagga | | |
| | | agaaattaaaaccac | | |
| | | caacccagtggccac | | |
| | | agaacagtacggcCA | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | Agtggccgataacct | | |
| | | gcaacagcaaaacgc | | |
| | | cgctcctattgtagg | | |
| | | gACTgtcaacagtca | | |
| | | aggagccttacctgg | | |
| | | catggtctggcagaa | | |
| | | ccgggacgtgtacct | | |
| | | gcaggtcctatctg | | |
| | | ggccaagattcctca | | |
| | | cacggacggaaactt | | |
| | | tcatccctcgccgct | | |
| | | gatgggaggctttgg | | |
| | | actgaaacacccgcc | | |
| | | tcctcagatcctgat | | |
| | | taagaatacacctgt | | |
| | | tcccgcggatcctcc | | |
| | | aactaccttcagtca | | |
| | | agctaagctggcgtc | | |
| | | gttcatcacgcagta | | |
| | | cagcaccggacaggt | | |
| | | cagcgtggaaattga | | |
| | | atgggagctgcagaa | | |
| | | agaaaacagcaaacg | | |
| | | ctggaacccagagat | | |
| | | tcaatacacttccaa | | |
| | | ctactacaaatctac | | |
| | | aaatgtggactttgc | | |
| | | tgttaacacaGAAgg | | |
| | | cacttattctgagcc | | |
| | | tcgccccatcggcac | | |
| | | ccgtTTCctcacccg | | |
| | | taatctgtaa | | |
| SL2LB | SEQ ID NO: 28 | atggctgccgatggt tatcttccagattgg ctcgaggacaacctc tctgagggcattcgc gagtggtgggacttg aaacctggagccccg aaacccaaagccaac cagcaaaagcaggac AACggccggggtctg gtgcttcctggctac aagtacctcggaccc ttcaacggactcgac aaggggggagcccgtc aacgcggcggacgca gcggccctcgagcac gacaaggcctacgac cagcagctcaaagcg ggtgacaatccgtac ctgAAGtataaccac gccgacgccgagttt caggagcgtctgcaa gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcacc cagcgttctccagac tcctctGCGggcatc ggcaagTCGggcGCA cagcccgcgaaaaag agactcaactttggg | SEQ ID NO: 29 | MAADGYLPDWLEDNL SEGIREWWDLKPGAP KPKANQQKQDNGRGL VLPGYKYLGPFNGLD KGEPVNAADAAALEH DKAYDQQLKAGDNPY LKYNHADAEFQERLQ EDTSFGGNLGRAVFQ AKKRVLEPLGLVEEG AKTAPGKKRPVEPSP QRSPDSSAGIGKSGA QPAKKRLNFGQTGDS ESVPDPQPIGEPPAG PSGLGSNTMAAGGGA PMADNNEGADGVGSA SGNWHCDSTWLGDRV ITTSTRTWALPTYNN HLYKQISSASTG_AS NDNHYFGYSTPWGYF DFNRFHCHFSPRDWQ RLINNNWGFRPKKLN FKLFNIQVKEVTQNE GTKTIANNLTSTIQV FTDSDYQLPYVLGSA HEGCLPPFPADVFMI PQYGYLTLNDGSQAV GRSSFYCLEYFPSQM LRTGNNFEFSYQFED VPFHSSYAHSQSLDR LMNPLIDQYLYFLSR TQSTGGTAGTQQLLF SQAGPSNMSAQAKNW LPGPCYRQQRVSTVT NQNNISNFAWTGATK YHLNGRDSLVNPGIA |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | cagactggcgactca | | MASHKEGEERFFPSS |
| | | gagtcagtgcccgac | | GILIFGKQGAGRDNV |
| | | cctcaaccaatcgga | | DYSKVMLTSEEEIKT |
| | | gaacccccgcaggc | | TNPVATEQYGQVADN |
| | | ccctctggtctggga | | LQQQNAAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggcgccgac | | PPQILIKNTPVPADP |
| | | ggagtgggtagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgacagagtc | | NYYKSTNVDFAVNTE |
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccTCAGCATCC | | |
| | | ACAgga_gccAGTaa | | |
| | | cgacaacCATtactt | | |
| | | cggctacagcacccc | | |
| | | ctgggggtattttga | | |
| | | ctttaacagattcca | | |
| | | ctgccacttctcacc | | |
| | | acgtgactggcagcg | | |
| | | actcatcaacaacaa | | |
| | | ctggggattccggcc | | |
| | | caagAAActcaactt | | |
| | | caagctcttcaacat | | |
| | | ccaggtcaaggaggt | | |
| | | cacgcagaatgaagg | | |
| | | caccaagaccatcgc | | |
| | | caataaccttaccag | | |
| | | cacgattcaggtctt | | |
| | | tacggactcgGACta | | |
| | | ccagctcccgtacgt | | |
| | | cctcggctctgcgca | | |
| | | cGAGggctgcctgcc | | |
| | | tccgttcccggcgga | | |
| | | cgtcttcatgattcc | | |
| | | tcagtacgggtacct | | |
| | | gactctgaacGATgg | | |
| | | cagtcaggccgtggg | | |
| | | ccgttcctccttcta | | |
| | | ctgcctggagtactt | | |
| | | tccttctcaaatgct | | |
| | | gagaacgggcaacaa | | |
| | | ctttgagttcagcta | | |
| | | ccagtttgaggacgt | | |
| | | gcctttcacagcag | | |
| | | ctacgcgcacagcca | | |
| | | aagcctggaccggct | | |
| | | gatgaacccctcat | | |
| | | cgaccagtacctgta | | |
| | | cTTCctgtctcggac | | |
| | | tcagtccacgggagg | | |
| | | taccgcaggaactca | | |
| | | gcagttgctatttc | | |
| | | tcaggccgggcctAG | | |
| | | Caacatgtcggctca | | |
| | | ggccaaaaactggct | | |
| | | acccgggccctgcta | | |
| | | ccggcagcaacgcgt | | |
| | | ctccacgGTAACCAA | | |
| | | CcaaaataacATCag | | |
| | | caactttgcctggac | | |
| | | cggtgccaccaagta | | |
| | | tcatctgaatggcag | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | agactctctggtaaa | | |
| | | tcccggtATCgctat | | |
| | | ggcaAGCcacaagGA | | |
| | | AGGAgaagagcgatt | | |
| | | ttttccgtccagcgg | | |
| | | aATCttaATTtttgg | | |
| | | gaaacagggagctgg | | |
| | | aAGAgacaacgtgga | | |
| | | ctatagcAAAgttat | | |
| | | gctaaccagtgagga | | |
| | | agaaattaaaaccac | | |
| | | caacccagtggccac | | |
| | | agaacagtacggcCA | | |
| | | Agtggccgataacct | | |
| | | gcaacagcaaaacgc | | |
| | | cgctcctattgtagg | | |
| | | gACTgtcaacagtca | | |
| | | aggagccttacctg | | |
| | | catggtctggcagaa | | |
| | | ccgggacgtgtacct | | |
| | | gcaggtcctatctg | | |
| | | ggccaagattcctca | | |
| | | cacggacggaaactt | | |
| | | tcatccctcgccgct | | |
| | | gatgggaggctttgg | | |
| | | actgaaacacccgc | | |
| | | tcctcagatcctgat | | |
| | | taagaatacacctgt | | |
| | | tcccgcggatcctcc | | |
| | | aactaccttcagtca | | |
| | | agctaagctggcgtc | | |
| | | gttcatcacgcagta | | |
| | | cagcaccggacaggt | | |
| | | cagcgtggaaattga | | |
| | | atgggagctgcagaa | | |
| | | agaaaacagcaaacg | | |
| | | ctggaacccagagat | | |
| | | tcaatacacttccaa | | |
| | | ctactacaaatctac | | |
| | | aaatgtggactttgc | | |
| | | tgttaacacaGAAgg | | |
| | | cacttattctgagcc | | |
| | | tcgccccatcggcac | | |
| | | ccgtTTCctcacccg | | |
| | | taatctgtaa | | |
| SL3 | SEQ ID NO: 5 | atggctgccgatggt tatcttccagattgg ctcgaggacaacctc tctgagggcattcgc gagtggtggGCTttg aaacctggagccccg CAAcccaaagccaac cagcaaaagcaggac AACGCTcggggtctg gtgcttcctggctac aagtacctcggaccc ttcaacggactcgac aaggggggacgcgtc aacgcggcggacgca gcggccctcgagcac gacaaggcctacgac cagcagctcaaagcg ggtgacaatccgtac ctgAAGtataaccac gccgacgccgagttt caggagcgtctgAAA gaagatacgtctttt | SEQ ID NO: 13 | MAADGYLPDWLEDNL SEGIREWWALKPGAP QPKANQQKQDNARGL VLPGYKYLGPFNGLD KGEPVNAADAAALEH DKAYDQQLKAGDNPY LKYNHADAEFQERLK EDTSFGGNLGRAVFQ AKKRVLEPLGLVEEG AKTAPGKKRPVEPSP QRSPDSSAGIGKSGA QPARKRLNFGQTGDT ESVPDPQPLGEPPAA PSGVGSNTMAAGGGA PMADNNEGADGVGSA SGNWHCDSTWLGDRV ITTSRTWALPTYNN HLYKQISNSTSGGST NDNTYFGYSTPWGYF DFNRFHCHFSPRDWQ RLINNNWGFRPKKLN FKLFNIQVKEVTQNE |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | gggggcaacctcggg | | GTKTIANNLTSTIQV |
| | | cgagcagtcttccag | | FTDSDYQLPYVLGSA |
| | | gccaagaagcgggtt | | HEGCLPPFPADVFMI |
| | | ctcgaacctctcggt | | PQYGYLTLNDGSQAV |
| | | ctggttgaggaaggc | | GRSSFYCLEYFPSQM |
| | | gctaagacggctcct | | LRTGNNFEFSYQFED |
| | | ggaaagaagagaccg | | VPFHSSYAHSQSLDR |
| | | gtagagccatcaccc | | LMNPLIDQYLYFLSR |
| | | cagcgttctccagac | | TQSTGGTAGTQQLLF |
| | | tcctctGCGggcatc | | SQAGPSNMSAQAKNW |
| | | ggcaagTCGggcGCA | | LPGPCYRQQRVSTVT |
| | | cagcccgcgAGAaag | | NQNNNSNFAWTGATK |
| | | agactcaactttggg | | YHLNGRDSLVNPGIA |
| | | cagactggcgacACA | | MASHKEGEERFFPSS |
| | | gagtcagtgcccgac | | GILIFGKQGAGRDNV |
| | | cctcaaccaCTCgga | | DYSKVMLTSEEEIKT |
| | | gaacccccgcaGCC | | TNPVATEEYGQVADN |
| | | ccctctggtGTGgga | | LQSANTAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggcgccgac | | PPQILIKNTPVPADP |
| | | ggagtgggtagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgacagagtc | | NYYKSTNVDFAVNTE |
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccaacAGCact | | |
| | | tcgggaggaagcacc | | |
| | | aacgacaacacctac | | |
| | | ttcggctacagcacc | | |
| | | ccctgggggtatttt | | |
| | | gactttaacagattc | | |
| | | cactgccacttctca | | |
| | | ccacgtgactggcag | | |
| | | cgactcatcaacaac | | |
| | | aactggggattccgg | | |
| | | cccaagAAActcaac | | |
| | | ttcaagctcttcaac | | |
| | | atccaggtcaaggag | | |
| | | gtcacgcagaatgaa | | |
| | | ggcaccaagaccatc | | |
| | | gccaataaccttacc | | |
| | | agcacgattcaggtc | | |
| | | tttacggactcgGAC | | |
| | | taccagctcccgtac | | |
| | | gtcctcggctctgcg | | |
| | | cacGAGggctgcctg | | |
| | | cctccgttcccggcg | | |
| | | gacgtcttcatgatt | | |
| | | cctcagtacgggtac | | |
| | | ctgactctgaacGAT | | |
| | | ggcagtcaggccgtg | | |
| | | ggccgttcctccttc | | |
| | | tactgcctggagtac | | |
| | | tttccttctcaaatg | | |
| | | ctgagaacgggcaac | | |
| | | aactttgagttcagc | | |
| | | taccagtttgaggac | | |
| | | gtgccttttccagac | | |
| | | agctacgcgcacagc | | |
| | | caaagcctggaccgg | | |
| | | ctgatgaaccccctc | | |
| | | atcgaccagtacctg | | |
| | | tacTTctgtctcgg | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | actcagtccacggga | | |
| | | ggtaccgcaggaact | | |
| | | cagcagttgctattt | | |
| | | tctcaggccgggcct | | |
| | | AGCaacatgtccgac | | |
| | | caggccaaaaactgg | | |
| | | ctacccgggccctgc | | |
| | | taccggcagcaacgc | | |
| | | gtctccacgGTAACC | | |
| | | AACcaaaataacaac | | |
| | | agcaactttgcctgg | | |
| | | accggtgccaccaag | | |
| | | tatcatctcgaatggc | | |
| | | agagactctctggta | | |
| | | aatcccggtATCgct | | |
| | | atggcaAGCcacaag | | |
| | | GAAGGAgaagagcga | | |
| | | tttttttccgtccagc | | |
| | | ggaATCttaATTttt | | |
| | | gggaaacagggagct | | |
| | | ggaAGAgacaacgtg | | |
| | | gactatagcAAAgtt | | |
| | | atgctaaccagtgag | | |
| | | gaagaaattaaaacc | | |
| | | accaacccagtggcc | | |
| | | acagaaGAAtacgac | | |
| | | CAAgtggccgataac | | |
| | | ctgcaaAGTGCCaac | | |
| | | ACGgctcctattgta | | |
| | | gggACTgtcaacagt | | |
| | | caaggagccttacct | | |
| | | ggcatggtctggcag | | |
| | | aaccgggacgtgtac | | |
| | | ctgcagggtcctatc | | |
| | | tgggccaagattcct | | |
| | | cacacggacggaaac | | |
| | | tttcatccctcgccg | | |
| | | ctgatgggaggcttt | | |
| | | ggactgaaacacccg | | |
| | | cctcctcagatcctg | | |
| | | attaagaatacacct | | |
| | | gttcccgcggatcct | | |
| | | ccaactaccttcagt | | |
| | | caagctaagctggcg | | |
| | | tcgttcatcacgcag | | |
| | | tacagcaccgacag | | |
| | | gtcagcgtggaaatt | | |
| | | gaatgggagctgcag | | |
| | | aaagaaaacagcaaa | | |
| | | cgctggaacccagag | | |
| | | attcaatacacttcc | | |
| | | aactactacaaatct | | |
| | | acaaatgtggacttt | | |
| | | gctgttaacacaGAA | | |
| | | ggcacttattctgag | | |
| | | cctcgccccatcggc | | |
| | | acccgtTTCctcacc | | |
| | | cgtaatctgtaa | | |
| SL3L | SEQ ID NO: 18 | atggctgccgatggt tatcttccagattgg ctcgaggacaacctc tctgagggcattcgc gagtggtggGCTttg aaacctggagccccg CAAcccaaagccaac cagcaaaagcaggac AACGCTcggggtctg | SEQ ID NO: 19 | MAADGYLPDWLEDNL SEGIREWWALKPGAP QPKANQQKQDNARGL VLPGYKYLGPFNGLD KGEPVNAADAAALEH DKAYDQQLKAGDNPY LKYNHADAEFQERLK EDTSFGGNLGRAVFQ AKKRVLEPLGLVEEG |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | gtgcttcctggctac | | AKTAPGKKRPVEPSP |
| | | aagtacctcggaccc | | QRSPDSSAGIGKSGA |
| | | ttcaacggactcgac | | QPARKRLNFGQTGDT |
| | | aaggggagcccgtc | | ESVPDPQPLGEPPAA |
| | | aacgcggcggacgca | | PSGVGSNTMAAGGGA |
| | | gcggccctcgagcac | | PMADNNEGADGVGSA |
| | | gacaaggcctacgac | | SGNWHCDSTWLGDRV |
| | | cagcagctcaaagcg | | ITTSTRTWALPTYNN |
| | | ggtgacaatccgtac | | HLYKQISNSTSGGST |
| | | ctgAAGtataaccac | | NDNTYFGYSTPWGYF |
| | | gccgacgccgagttt | | DFNRFHCHFSPRDWQ |
| | | caggagcgtctgAAA | | RLINNNWGFRPKKLN |
| | | gaagatacgtctttt | | FKLFNIQVKEVTQNE |
| | | gggggcaacctcggg | | GTKTIANNLTSTIQV |
| | | cgagcagtcttccag | | FTDSDYQLPYVLGSA |
| | | gccaagaagcgggtt | | HEGCLPPFPADVFMI |
| | | ctcgaacctctcggt | | PQYGYLTLNDGSQAV |
| | | ctggttgaggaaggc | | GRSSFYCLEYFPSQM |
| | | gctaagacggctcct | | LRTGNNFEFSYQFED |
| | | ggaaagaagagaccg | | VPFHSSYAHSQSLDR |
| | | gtagagccatcaccc | | LMNPLIDQYLYFLSR |
| | | cagcgttctccagac | | TQSTGGTAGTQQLLF |
| | | tcctctGCGggcatc | | SQAGPSNMSAQAKNW |
| | | ggcaagTCGggcGCA | | LPGPCYRQQRVSTVT |
| | | cagcccgcgAGAaag | | NQNNISNFAWTGATK |
| | | agactcaactttggg | | YHLNGRDSLVNPGIA |
| | | cagactggcgacACA | | MASHKEGEERFFPSS |
| | | gagtcagtgcccgac | | GILIFGKQGAGRDNV |
| | | cctcaaccaCTCgga | | DYSKVMLTSEEEIKT |
| | | gaaccccccgcaGCC | | TNPVATEEYGQVADN |
| | | ccctctggtGTGgga | | LQSANTAPIVGTVNS |
| | | tctAATacaatggct | | QGALPGMVWQNRDVY |
| | | gcaggcggtggcgct | | LQGPIWAKIPHTDGN |
| | | ccaatggcagacaat | | FHPSPLMGGFGLKHP |
| | | aacgaaggcgccgac | | PPQILIKNTPVPADP |
| | | ggagtgggtagtGCC | | PTTFSQAKLASFITQ |
| | | tcaggaaattggcat | | YSTGQVSVEIEWELQ |
| | | tgcgattccacatgg | | KENSKRWNPEIQYTS |
| | | ctgggcgacagagtc | | NYYKSTNVDFAVNTE |
| | | atcaccaccagcacc | | GTYSEPRPIGTRFLT |
| | | cgaacctgggccctc | | RNL |
| | | cccacctacaacaac | | |
| | | cacctctacaagcaa | | |
| | | atctccaacAGCact | | |
| | | tcgggaggaagcacc | | |
| | | aacgacaacacctac | | |
| | | ttcggctacagcacc | | |
| | | ccctgggggtatttt | | |
| | | gactttaacagattc | | |
| | | cactgccacttctca | | |
| | | ccacgtgactggcag | | |
| | | cgactcatcaacaac | | |
| | | aactggggattccgg | | |
| | | cccaagAAActcaac | | |
| | | ttcaagctcttcaac | | |
| | | atccaggtcaaggag | | |
| | | gtcacgcagaatgaa | | |
| | | ggcaccaagaccatc | | |
| | | gccaataaccttacc | | |
| | | agcacgattcaggtc | | |
| | | tttacggactcgGAC | | |
| | | taccagctcccgtac | | |
| | | gtcctcggctctgcg | | |
| | | cacGAGgctgcctg | | |
| | | cctccgttcccggcg | | |
| | | gacgtcttcatgatt | | |
| | | cctcagtacgggtac | | |
| | | ctgactctgaacGAT | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | ggcagtcaggccgtg | | |
| | | ggccgttcctccttc | | |
| | | tactgcctggagtac | | |
| | | tttccttctcaaatg | | |
| | | ctgagaacgggcaac | | |
| | | aactttgagttcagc | | |
| | | taccagtttgaggac | | |
| | | gtgccttttcacagc | | |
| | | agctacgcgcaacgg | | |
| | | caaaagcctggaccgg | | |
| | | ctgatgaaccccctc | | |
| | | atcgaccagtacctg | | |
| | | tacTTCctgtctcgg | | |
| | | actcagtccacggga | | |
| | | ggtaccgcaggaact | | |
| | | cagcagttgctattt | | |
| | | tctcaggccgggcct | | |
| | | AGCaacatgtcggct | | |
| | | caggccaaaaactgg | | |
| | | ctacccgggccctgc | | |
| | | taccggcagcaacgc | | |
| | | gtctccacgGTAACC | | |
| | | AACcaaaataacATC | | |
| | | agcaactttgcctgg | | |
| | | accggtgccaccaag | | |
| | | tatcatctgaactgg | | |
| | | agagactctctggta | | |
| | | aatcccggtATCgct | | |
| | | atggcaAGCcacaag | | |
| | | GAAGGAgaagagcga | | |
| | | ttttttccgtccagc | | |
| | | ggaATCttaATTttt | | |
| | | gggaaacagggagct | | |
| | | ggaAGAgacaagcgg | | |
| | | gactatagcAAAgtt | | |
| | | atgctaaccagtgag | | |
| | | gaagaaattaaaacc | | |
| | | accaacccagtggcc | | |
| | | acagaaGAAtacggc | | |
| | | CAAgtggccgataac | | |
| | | ctgcaaAGTGCCaac | | |
| | | ACGgctcctattgta | | |
| | | gggACTgtcaacagt | | |
| | | caaggagccttacct | | |
| | | ggcatggtctggcag | | |
| | | aaccgggacgtgtac | | |
| | | ctgcagggtcctatc | | |
| | | tgggccaagattcct | | |
| | | cacacggacggaaac | | |
| | | tttcatccctcgccg | | |
| | | ctgatgggaggcttt | | |
| | | ggactgaaacacccg | | |
| | | cctcctcagatcctg | | |
| | | attaagaatacacct | | |
| | | gttcccgcggatcct | | |
| | | ccaactaccttcagt | | |
| | | caagctaagctggcg | | |
| | | tcgttcatcacgcag | | |
| | | tacagcaccggacag | | |
| | | gtcagcgtggaaatt | | |
| | | gaatgggagctgcag | | |
| | | aaagaaaacagcaaa | | |
| | | cgctggaacccagag | | |
| | | attcaatacacttcc | | |
| | | aactactacaaatct | | |
| | | acaaatgtggacttt | | |
| | | gctgttaacacaGAA | | |
| | | ggcacttattctgag | | |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Variant | SEQ ID NO | Nucleic Acid Sequence | SEQ ID NO | Amino Acid Sequence |
|---|---|---|---|---|
| | | cctcgcccatcggc acccgtTTCctcacc cgtaatctgtaa | | |
| SL3B | SEQ ID NO: 24 | atggctgccgatggt tatcttccagattgg ctcgaggacaacctc tctgagggcattcgc gagtggtggGCTttg aaacctggagccccg CAAcccaaagccaac cagcaaaagcaggac AACGCTcggggtctg gtgcttcctggctac aagtacctcggaccc ttcaacggactcgac aaggggagcccgtc aacgcggcggacgca gcggccctcgagcac gacaaggcctacgac cagcagctcaaagcg ggtgacaatccgtac ctgAAGtataaccac gccgacgccgagttt caggagcgtctgAAA gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcaccc cagcgttctccagac tcctctGCGggcatc ggcaagTCGggcGCA cagcccgcgAGAaag agactcaactttggg cagactggcgacACA gagtcagtgcccgac cctcaaccaCTCgga gaacccccgcaGCC ccctctggtGTGgga tctAATacaatggct gcaggcggtggcgct ccaatggcagacaat aacgaaggcgccgac ggagtgggtagtGCC tcaggaaattggcat tgcgattccacatgg ctgggcgacagagtc atcaccaccagcacc cgaacctgggccctc cccacctacaacaac cacctctacaagcaa atctccTCAGCATCC ACAgga_gccAGTaa cgacaacCATtactt cggctacagcacccc ctggggtattttga ctttaacagattcca ctgccacttctcacc acgtgactggcagcg actcatcaacaacaa ctggggattccggcc caagAAActcaactt caagctcttcaacat | SEQ ID NO: 25 | MAADGYLPDWLEDNL SEGIREWWALKPGAP QPKANQQKQDNARGL VLPGYKYLGPFNGLD KGEPVNAADAAALEH DKAYDQQLKAGDNPY LKYNHADAEFQERLK EDTSFGGNLGRAVFQ AKKRVLEPLGLVEEG AKTAPGKKRPVEPSP QRSPDSSAGIGKSGA QPARKRLNFGQTGDT ESVPDPQPLGEPPAA PSGVGSNTMAAGGGA PMADNNEGADGVGSA SGNWHCDSTWLGDRV ITTSTRTWALPTYNN HLYKQISSASTG_AS NDNHYFGYSTPWGYF DFNRFHCHFSPRDWQ RLINNNWGFRPKKLN FKLFNIQVKEVTQNE GTKTIANNLTSTIQV FTDSDYQLPYVLGSA HEGCLPPFPADVFMI PQYGYLTLNDGSQAV GRSSFYCLEYFPSQM LRTGNNFEFSYQFED VPFHSSYAHSQSLDR LMNPLIDQYLYFLSR TQSTGGTAGTQQLLF SQAGPSNMSAQAKNW LPGPCYRQQRVSTVT NQNNNSNFAWTGATK YHLNGRDSLVNPGIA MASHKEGEERFFPSS GILIFGKQGAGRDNV DYSKVMLTSEEEIKT TNPVATEEYGQVADN LQSANTAPIVGTVNS QGALPGMVWQNRDVY LQGPIWAKIPHTDGN FHPSPLMGGFGLKHP PPQILIKNTPVPADP PTTFSQAKLASFITQ YSTGQVSVEIEWELQ KENSKRWNPEIQYTS NYYKSTNVDFAVNTE GTYSEPRPIGTRFLT RNL |

TABLE 1-continued

Nucleic acid and amino acid sequences for AAV variants SL1.2, SL1.2L, SL1.2B, SL1.2LB, SL2, SL2L, SL2B, SL2LB, SL3, SL3L, SL3B, and SL3LB. Codons shown in all caps in the nucleic acid sequences are the codon differences from wild-type AAV8 capsid protein. Underscores indicate deletions.

| Variant | SEQ ID NO | Nucleic Acid Sequence | SEQ ID NO | Amino Acid Sequence |
|---|---|---|---|---|
| | | ccaggtcaaggaggt cacgcagaatgaagg caccaagaccatcgc caataaccttaccag cacgattcaggtctt tacggactcgGACta ccagctcccgtacgt cctcggctctgcgca cGAGggcgcctgcc tccgttcccggcgga cgtcttcatgattcc tcagtacgggtacct gactctgaacGATgg cagtcaggccgtggg ccgttcctccttcta ctgcctggagtactt tccttctcaaatgct gagaacgggcaacaa ctttgagttcagcta ccagtttgaggacgt gcctttttcacagcag ctacgcgcaacgca aagcctggaccggct gatgaacccctcat cgaccagtacctgta cTTCctgtctcggac tcagtccacgggagg taccgcaggaactca gcagttgctatttc tcaggccgggcctAG Caacatgtcggctca ggccaaaaactggct acccgggccctgcta ccggcagcaacgcgt ctccacgGTAACCAA Ccaaaataacaatag caactttgcctggac cggtgccaccaagta tcatctgaatggcag agactctctggtaaa tcccggtATCgctat ggcaAGCcacaagGA AGGAgaagagcgatt ttttccgtccagcgg aATCttaATTttttgg gaaacagggagctgg aAGAgacaacgtgg ctatagcAAAgttat gctaaccagtgagga agaaattaaaaccac caacccagtggccac agaaGAAtacggcCA Agtggccgataacct gcaaAGTGCCaacAC Ggctcctattgtagg gACTgtcaacagtca aggagccttacctgg catggtctggcagaa ccgggacgtgtacct gcagggtcctatctg ggccaagattcctca cacggacggaaactt tcatccctcgccgct gatgggaggctttgg actgaaacacccgcc tcctcagatcctgat taagaatacacctgt tcccgcggatcctcc |  | |

TABLE 1-continued TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | aactaccttcagtca | | |
| | | agctaagctggcgtc | | |
| | | gttcatcacgcagta | | |
| | | cagcaccggacaggt | | |
| | | cagcgtggaaattga | | |
| | | atgggagctgcagaa | | |
| | | agaaaacagcaaacg | | |
| | | ctggaacccagagat | | |
| | | tcaatacacttccaa | | |
| | | ctactacaaatctac | | |
| | | aaatgtggactttgc | | |
| | | tgttaacacaGAAgg | | |
| | | cacttattctgagcc | | |
| | | tcgccccatcggcac | | |
| | | ccgtTTCctcacccg | | |
| | | taatctgtaa | | |
| SL3LB | SEQ ID NO: 30 | atggctgccgatggt tatcttccagattgg ctcgaggacaacctc tctgagggcattcgc gagtggtggGCTttg aaacctggagccccg CAAcccaaagccaac cagcaaaagcaggac AACGCTcggggtctg gtgcttcctggctac aagtacctcggaccc ttcaacggactcgac aaggggggagcccgtc aacgcggcggacgca gcggccctcgagcac gacaaggcctacgac cagcagctcaaagcg ggtgacaatccgtac ctgAAGtataaccac gccgacgccgagttt caggagcgtctgAAA gaagatacgtctttt gggggcaacctcggg cgagcagtcttccag gccaagaagcgggtt ctcgaacctctcggt ctggttgaggaaggc gctaagacggctcct ggaaagaagagaccg gtagagccatcaccc cagcgttctccagac tcctctGCGggcatc ggcaagTCGggcGCA cagcccgcgAGAaag agactcaactttggg cagactggcgacACA gagtcagtgcccgac cctcaaccaCTCgga gaaccccccgcaGCC ccctctggtGTGgga tctAATacaatggct gcaggcggtggcgct ccaatggcagacaat aacgaaggcgccgac ggagtgggtagtGCC tcaggaaattggcat tgcgattccacatgg ctgggcgacagagtc atcaccaccagcacc cgaacctgggccctc cccacctacaacaac | SEQ ID NO: 31 | MAADGYLPDWLEDNL SEGIREWWALKPGAP QPKANQQKQDNARGL VLPGYKYLGPFNGLD KGEPVNAADAAALEH DKAYDQQLKAGDNPY LKYNHADAEFQERLK EDTSFGGNLGRAVFQ AKKRVLEPLGLVEEG AKTAPGKKRPVEPSP QRSPDSSAGIGKSGA QPARKRLNFGQTGDT ESVPDPQPLGEPPAA PSGVGSNTMAAGGGA PMADNNEGADGVGSA SGNWHCDSTWLGDRV ITTSTRTWALPTYNN HLYKQISSASTG_AS NDNHYFGYSTPWGYF DFNRFHCHFSPRDWQ RLINNNWGFRPKKLN FKLFNIQVKEVTQNE GTKTIANNLTSTIQV FTDSDYQLPYVLGSA HEGCLPPFPADVFMI PQYGYLTLNDGSQAV GRSSFYCLEYFPSQM LRTGNNFEFSYQFED VPFHSSYAHSQSLDR LMNPLIDQYLYFLSR TQSTGGTAGTQQLLF SQAGPSNMSAQAKNW LPGPCYRQQRVSTVT NQNNISNFAWTGATK YHLNGRDSLVNPGIA MASHKEGEERFFPSS GILIFGKQGAGRDNV DYSKVMLTSEEEIKT TNPVATEEYGQVADN LQSANTAPIVGTVNS QGALPGMVWQNRDVY LQGPIWAKIPHTDGN FHPSPLMGGFGLKHP PPQILIKNTPVPADP PTTFSQAKLASFITQ YSTGQVSVEIEWELQ KENSKRWNPEIQYTS NYYKSTNVDFAVNTE GTYSEPRPIGTRFLT RNL |

| Vari-ant | SEQ ID NO | Nucleic Acid Sequence | SEQ ID NO | Amino Acid Sequence |
|---|---|---|---|---|
| | | cacctctacaagcaa | | |
| | | atctccTCAGCATCC | | |
| | | ACAgga_gccAGTaa | | |
| | | cgacaacCATtactt | | |
| | | cggctacagcaccCC | | |
| | | ctggggggtattttga | | |
| | | ctttaacagattcca | | |
| | | ctgccacttctcacc | | |
| | | acgtgactggcagcg | | |
| | | actcatcaacaacaa | | |
| | | ctggggattccggcc | | |
| | | caagAAActcaactt | | |
| | | caagctcttcaacat | | |
| | | ccaggtcaaggaggt | | |
| | | cacgcagaatgaagg | | |
| | | caccaagaccatcgc | | |
| | | caataaccttaccag | | |
| | | cacgattcaggtctt | | |
| | | tacggactcgGACta | | |
| | | ccagctcccgtacgt | | |
| | | cctcggctctgcgca | | |
| | | cGAGggcgcctgcc | | |
| | | tccgttcccggcgga | | |
| | | cgtcttcatgattcc | | |
| | | tcagtacgggtacct | | |
| | | gactctgaacGATgg | | |
| | | cagtcaggccgtggg | | |
| | | ccgttcctccttcta | | |
| | | ctgcctggagtactt | | |
| | | tccttctcaaatgct | | |
| | | gagaacgggcaacaa | | |
| | | ctttgagttcagcta | | |
| | | ccagtttgaggacgt | | |
| | | gccttttcaacggag | | |
| | | ctacgcgcacagcca | | |
| | | aagcctggaccggct | | |
| | | gatgaacccctcat | | |
| | | cgaccagtacctgta | | |
| | | cTTCctgtctcggac | | |
| | | tcagtccacgggagg | | |
| | | taccgcaggaactca | | |
| | | gcagttgctattttc | | |
| | | tcaggccgggcctAG | | |
| | | Caacatgtcggctca | | |
| | | ggccaaaaactggct | | |
| | | acccgggccctgcta | | |
| | | ccggcagcaacgcgt | | |
| | | ctccacgGTAACCAA | | |
| | | CcaaaataacATCag | | |
| | | caactttgcctggac | | |
| | | cggtgccaccaagta | | |
| | | tcatctgaatggcag | | |
| | | agactctctggtaaa | | |
| | | tcccggtATCgctat | | |
| | | ggcaAGCcacaagGA | | |
| | | AGGAgaagagcgatt | | |
| | | ttttccgtccagcgg | | |
| | | aATCttaATTtttgg | | |
| | | gaaacagggagctgg | | |
| | | aAGAgacaacgtgga | | |
| | | ctatagcAAAgttat | | |
| | | gctaaccagtgagga | | |
| | | agaaattaaaaccac | | |
| | | caacccagtggccaa | | |
| | | agaaGAAtacggcCA | | |
| | | Agtggccgataacct | | |
| | | gcaaAGTGCCaacAC | | |
| | | Ggctcctattgtagg | | |

TABLE 1-continued

Nucleic acid and amino acid sequences for AAV
variants SL1.2, SL1.2L, SL1.2B, SL1.2LB, SL2,
SL2L, SL2B, SL2LB, SL3, SL3L, SL3B, and SL3LB.
Codons shown in all caps in the nucleic acid
sequences are the codon differences from wild-
type AAV8 capsid protein. Underscores indicate
deletions.

| Vari-ant | SEQ ID NO | Nucleic Acid Sequence | SEQ ID NO | Amino Acid Sequence |
|---|---|---|---|---|
| | | gACTgtcaacagtca | | |
| | | aggagccttacctgg | | |
| | | catggtctggcagaa | | |
| | | ccgggacgtgtacct | | |
| | | gcagggtcctatctg | | |
| | | ggccaagattcctca | | |
| | | cacggacggaaactt | | |
| | | tcatccctcgccgct | | |
| | | gatgggaggctttgg | | |
| | | actgaaacacccgcc | | |
| | | tcctcagatcctgat | | |
| | | taagaatacacctgt | | |
| | | tcccgcggatcctcc | | |
| | | aactaccttcagtca | | |
| | | agctaagctggcgtc | | |
| | | gttcatcacgcagta | | |
| | | cagcaccggacaggt | | |
| | | cagcgtggaaattga | | |
| | | atgggagctgcagaa | | |
| | | agaaaacagcaaacg | | |
| | | ctggaacccagagat | | |
| | | tcaatacacttccaa | | |
| | | ctactacaaatctac | | |
| | | aaatgtggactttgc | | |
| | | tgttaacacaGAAgg | | |
| | | cacttattctgagcc | | |
| | | tcgccccatcggcac | | |
| | | ccgtTTCctcacccg | | |
| | | taatctgtaa | | |

It is to be understood that any one of the variant recombinant AAV (e.g., rAAV8) capsid proteins disclosed herein may have any one single amino acid substitution described herein, or any combination of amino acid substitutions described herein.

For example, in some embodiments SL1.2, SL2, and SL3 are further mutated. In some embodiments, SL1.2, SL2, and SL3 are further mutated to alter the tropism of the variants to certain tissues (e.g., heart, neural, or other muscle tissue). In some embodiments, the further mutations of SL1.2, SL2, and SL3 improve the uptake of SL1.2, SL2, and/or SL3 in the tissue of interest (e.g., heart, neural, or other muscle tissue). In some embodiments, the further mutations of SL1.2, SL2, and SL3 reduce the uptake of SL1.2, SL2, and/or SL3 in the tissue of non-interest (e.g., neural or liver tissue).

In some embodiments, the capsid region spanning amino acids Glu578 to Gly596 is further mutated in SL1.2, SL2, and/or SL3. In some embodiments, one amino acid is further mutated in SL1.2, SL2, and/or SL3: Asparagine 500 to Isoleucine. In some embodiments, the further mutations introduced into any of SL1.2, SL2, and SL3 incorporate those described in Pulicherla, et al., *Mol. Ther.* 19:6, 1070-78 (2011). In some embodiments, the Asparagine 500 to Isoleucine mutation in SL1.2, SL2, and/or SL3 results in reduced liver tissue tropism.

In some embodiments, the Asparagine 500 to Isoleucine mutation in SL1.2 results in an AAV variant protein having the amino acid sequence of SEQ ID NO: 15 ("SL1.2L"). In some embodiments, the Asparagine 500 to Isoleucine mutation in SL1.2 results in an AAV variant protein that is encoded by a nucleic acid having the sequence of SEQ ID NO: 14. In some embodiments, the Asparagine 500 to Isoleucine mutation in SL2 results in an AAV variant protein having the amino acid sequence of SEQ ID NO: 17 ("SL2L"). In some embodiments, the Asparagine 500 to Isoleucine mutation in SL2 results in an AAV variant protein that is encoded by a nucleic acid having the sequence of SEQ ID NO: 16. In some embodiments, the Asparagine 500 to Isoleucine mutation in SL3 results in an AAV variant protein having the amino acid sequence of SEQ ID NO: 19 ("SL3L"). In some embodiments, the Asparagine 500 to Isoleucine mutation in SL3 results in an AAV variant protein that is encoded by a nucleic acid having that sequence of SEQ ID NO: 18.

In some embodiments, seven amino acids are further mutated in SL1.2: Asparagine 263 to Serine; Glycine 264 to Alanine; Threonine 265 to Serine; Serine 266 to Threonine; deletion of Glycine 268; Threonine 270 to Serine; and Threonine 274 to Histidine ("the seven amino acid mutations in SL1.2"). In some embodiments, eight amino acids are further mutated in SL2: Asparagine 263 to Serine; Serine 264 to Alanine; Threonine 265 to Serine; Serine 266 to Threonine; deletion of Glycine 268; Serine 269 to Alanine; Threonine 270 to Serine; and Threonine 274 to Histidine ("the eight amino acid mutations in SL2"). In some embodiments, eight amino acids are further mutated in SL3: Asparagine 263 to Serine; Serine 264 to Alanine; Threonine 265 to Serine; Serine 266 to Threonine; deletion of Glycine 268; Serine 269 to Alanine; Threonine 270 to Serine; and Threonine 274 to Histidine ("the eight amino acid mutations in SL3"). In some embodiments, the further mutations introduced into any of SL1.2, SL2, and SL3 incorporate those described in Albright, et al., *Mol. Ther.* 26:2, 510-23 (2018). In some embodiments, the seven amino acid mutations in SL1.2 or the eight amino acid mutations in SL2 and/or SL3 results in reduced brain tissue tropism.

In some embodiments, the seven amino acid mutations in SL1.2 result in an AAV variant protein having the amino acid sequence of SEQ ID NO: 21 ("SL1.2B"). In some embodiments, the seven amino acid mutations in SL1.2 result in an AAV variant protein that is encoded by a nucleic acid having that sequence of SEQ ID NO: 20. In some embodiments, the eight amino acid mutations in SL2 result in an AAV variant protein having the amino acid sequence of SEQ ID NO: 23 ("SL2B"). In some embodiments, the eight amino acid mutations in SL2 result in an AAV variant protein that is encoded by a nucleic acid having that sequence of SEQ ID NO: 22. In some embodiments, the eight amino acid mutations in SL3 result in an AAV variant protein having the amino acid sequence of SEQ ID NO: 25 ("SL3B"). In some embodiments, the eight amino acid mutations in SL3 result in an AAV variant protein that is encoded by a nucleic acid having that sequence of SEQ ID NO: 24.

In some embodiments, eight amino acids are further mutated in SL1.2: Asparagine 500 to Isoleucine; Asparagine 263 to Serine; Glycine 264 to Alanine; Threonine 265 to Serine; Serine 266 to Threonine; deletion of Glycine 268; Threonine 270 to Serine; and Threonine 274 to Histidine ("the seven amino acid mutations in SL1.2"). In some embodiments, the eight amino acid mutations in SL1.2 results in reduced liver and brain tissue tropism. In some embodiments, the eight amino acid mutations in SL1.2 result in an AAV variant protein having the amino acid sequence of SEQ ID NO: 27 ("SL1.2LB"). In some embodiments, the eight amino acid mutations in SL1.2 result in an AAV variant protein that is encoded by a nucleic acid having that sequence of SEQ ID NO: 26.

In some embodiments, nine amino acids are further mutated in SL2: Asparagine 500 to Isoleucine; Asparagine 263 to Serine; Serine 264 to Alanine; Threonine 265 to Serine; Serine 266 to Threonine; deletion of Glycine 268; Serine 269 to Alanine; Threonine 270 to Serine; and Threonine 274 to Histidine ("the nine amino acid mutations in SL2"). In some embodiments, the nine amino acid mutations in SL2 results in reduced liver and brain tissue tropism. In some embodiments, the nine amino acid mutations in SL2 result in an AAV variant protein having the amino acid sequence of SEQ ID NO: 29 ("SL2LB"). In some embodiments, the nine amino acid mutations in SL2 result in an AAV variant protein that is encoded by a nucleic acid having that sequence of SEQ ID NO: 28.

In some embodiments, nine amino acids are further mutated in SL3: Asparagine 500 to Isoleucine; Asparagine 263 to Serine; Serine 264 to Alanine; Threonine 265 to Serine; Serine 266 to Threonine; deletion of Glycine 268; Serine 269 to Alanine; Threonine 270 to Serine; and Threonine 274 to Histidine ("the nine amino acid mutations in SL3"). In some embodiments, the nine amino acid mutations in SL3 results in reduced liver and brain tissue tropism. In some embodiments, the nine amino acid mutations in SL3 result in an AAV variant protein having the amino acid sequence of SEQ ID NO: 31 ("SL3LB"). In some embodiments, the nine amino acid mutations in SL3 result in an AAV variant protein that is encoded by a nucleic acid having that sequence of SEQ ID NO: 30.

Contemplated herein are also variant rAAV capsid proteins of serotypes other than serotype 8. In some embodiments, any one of the amino acid changes described herein are in a variable region of the capsid protein of a serotype other than serotype 8 that is homologous to the variable region of AAV8 (e.g., 1, 2, 3, 3B, 4, 5, 6, 7, 9, 10, 11, 12, or 13). In some embodiments, a variant rAAV capsid could be made on a background of the cap gene of one serotype delivered with the rep gene of a different serotype.

Recombinant AAV Vectors

As used herein, the term "vector" may refer to a nucleic acid vector (e.g., a plasmid or recombinant viral genome), a wild-type AAV genome, or a virus that comprises a viral genome. In some embodiments, the term "vector" may refer to a viral particle, such as an AAV viral particle.

The wild-type AAV genome is a single-stranded deoxyribonucleic acid (ssDNA), either positive- or negative-sensed. The genome comprises two inverted terminal repeats (ITRs), one at each end of the DNA strand, and two open reading frames (ORFs): rep and cap between the ITRs. The rep ORF comprises four overlapping genes encoding Rep proteins required for the AAV life cycle. The cap ORF comprises overlapping genes encoding capsid proteins: VP1, VP2 and VP3, which interact together to form the viral capsid. VP1, VP2 and VP3 are translated from one mRNA transcript, which can be spliced in two different manners. Either a longer or shorter intron can be excised resulting in the formation of two isoforms of mRNAs: a ~2.3 kb- and a ~2.6 kb-long mRNA isoform. The capsid forms a supramolecular assembly of approximately 60 individual capsid protein subunits into a non-enveloped, T-1 icosahedral lattice capable of protecting the AAV genome. A mature AAV capsid is composed of VP1, VP2, and VP3 (molecular masses of approximately 87, 73, and 62 kDa respectively) in a ratio of about 1:1:10.

Recombinant AAV (rAAV) particles may comprise a recombinant nucleic acid vector (hereafter referred to as "rAAV vector"), which may comprise at a minimum: (a) one or more heterologous nucleic acid regions comprising a sequence encoding a transgene; and (b) one or more regions comprising sequences that facilitate the integration of the heterologous nucleic acid region (optionally with the one or more nucleic acid regions comprising a sequence that facilitates expression) into the genome of the subject. In some embodiments, the sequences facilitating the integration of the heterologous nucleic acid region (optionally with the one or more nucleic acid regions comprising a sequence that facilitates expression) into the genome of the subject are inverted terminal repeat (ITR) sequences (e.g., wild-type ITR sequences or engineered ITR sequences) flanking the one or more nucleic acid regions (e.g., heterologous nucleic acid regions).

In some embodiments, the rAAV nucleic acid vector comprises one or more transgenes comprising a sequence encoding a protein or polypeptide of interest operably linked to a promoter, wherein the one or more transgenes are flanked on each side with an ITR sequence. In some embodiments, the nucleic acid vector further comprises a region encoding a Rep protein as described herein, either contained within the region flanked by ITRs or outside the region or nucleic acid) operably linked to a promoter. The ITR sequences may be derived from any AAV serotype (e.g., 1, 2, 3, 4, 5, 6, 7, 8, 9, or 10) or may be derived from more than one serotype. In some embodiments, the ITR sequences are derived from AAV2 or AAV6 serotypes. In some embodiments, a first serotype provided herein is not an AAV2 or AAV8 serotype. In some embodiments, the ITR sequences of the first serotype are derived from AAV3, AAV5 or AAV6. In some embodiments, the ITR sequences are derived from AAV2, AAV3, AAV5 or AAV6. In some embodiments, the ITR sequences are the same serotype as the capsid (e.g., AAV6 ITR sequences and AAV6 capsid, etc.). In some embodiments, the ITR sequences are derived from AAVrh.10 serotype.

In some embodiments, a recombinant AAV (e.g., rAAV8) particle containing any one of the variant rAAV capsid proteins disclosed herein comprises ITRs and/or rep ORF of serotype 8. In some embodiments, a rAAV particle is a pseudotyped rAAV particle, which comprises (a) a capsid comprised of capsid proteins containing modifications described herein made on a serotype 8 background, and (b) a nucleic acid vector comprising ITRs from another serotype (e.g., AAV1, AAV2, AAV3, AAV4, AAV5, AAV6, AAV7, AAV9, or AAV10).

The rAAV particles or particles within an rAAV preparation disclosed herein, may be of any AAV serotype, including any derivative or pseudotype (e.g., 1, 2, 3, 4, 5, 6, 7, 8, 9, 10, 2/1, 2/5, 2/8, 2/9, 3/1, 3/5, 3/8, or 3/9). As used herein, the serotype of an rAAV an rAAV particle refers to the serotype of the capsid proteins of the recombinant virus. In some embodiments, the rAAV particle is rAAV6 or rAAV9. Non-limiting examples of derivatives and pseudotypes include AAVrh.10, AAVrh.74, AAV2/1, AAV2/5, AAV2/6, AAV2/8, AAV2/9, AAV2-AAV3 hybrid, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In particular embodiments, the capsid of any of the herein disclosed rAAV particles is of the AAVrh.10 serotype. In some embodiments, the capsid is of the AAV2/6 serotype. In some embodiments, the rAAV particle is a pseudotyped rAAV particle, which comprises (a) an rAAV vector comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, et al. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). In some embodiments, the rAAV comprises a pTR-UF-11 plasmid backbone, which is a plasmid that contains AAV2 ITRs. This plasmid is commercially available from the American Type Culture Collection (ATCC MBA-331).

Provided herein are variant recombinant AAV (e.g., rAAV8) particles. In some embodiments, a particle is an empty particle (e.g., one that does not contain a nucleic acid vector comprising a gene of interest). In some embodiments, an AAV8 particle contains a nucleic acid vector comprising a gene of interest. As used herein, "a gene of interest" is a gene that encodes an RNA or protein of interest.

Thus, in some embodiments, the rAAV vector comprises one or more regions comprising a sequence that facilitates expression of the gene of interest, e.g., expression control sequences operably linked to the nucleic acid. Numerous such sequences are known in the art. Non-limiting examples of expression control sequences include promoters, insulators, silencers, response elements, introns, enhancers, initiation sites, internal ribosome entry sites (IRES) termination signals, and poly(A) signals. Any combination of such control sequences is contemplated herein (e.g., a promoter and an enhancer). In some embodiments, the rAAV vectors comprise a promoter that is operably linked to the coding sequence of the gene of interest and facilitates expression of the gene of interest. A "promoter", as used herein, refers to a control region of a nucleic acid at which initiation and rate of transcription of the remainder of a nucleic acid sequence are controlled. A promoter drives transcription of the nucleic acid sequence that it regulates, thus, it is typically located at or near the transcriptional start site of a gene. A promoter may have, for example, a length of 100 to 1000 nucleotides. In some embodiments, a promoter is operably linked to a nucleic acid, or a sequence of a nucleic acid (nucleotide sequence). In some embodiments, one or more promoters may be operably linked to a coding nucleotide sequence in the heterologous nucleic acid. A promoter is considered to be "operably linked" to a sequence of nucleic acid that it regulates when the promoter is in a correct functional location and orientation relative to the sequence such that the promoter controls and/or regulates (e.g., to control ("drive") transcriptional initiation and/or expression of) that sequence. A promoter may be a constitutive promoter, tissue-specific promoter, an inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. In some embodiments, chimeric viral/mammalian promoters may include a chimeric CMV/chicken beta actin (CBA, CB or CAG) promoters.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. In some embodiments, the promoter may be a tissue-specific promoter. A "tissue-specific promoter", as used herein, refers to promoters that can only function in a specific type of tissue, e.g., the heart. Thus, a "tissue-specific promoter" is not able to drive the expression of the transgenes in other types of tissues. In some embodiments, it may be beneficial to combine a variant rAAV particle as disclosed herein, with a promoter that also targets the same cells, tissue, or organ as the variant rAAV particle. For example, for variants with improved cardiac tropism, the use of a cardiac troponin T promoter to achieve cardiac-specific expression would be appropriate.

Promoters that may be used in accordance with the present disclosure may in some embodiments comprise any promoter that can drive the expression of the transgenes in the heart of the subject. In some embodiments, the promoter that may be used in accordance with the present disclosure is a cardiac-restricted promoter. For example, promoter is a cardiac-restricted promoter selected from cardiac troponin C, cardiac troponin I, and cardiac troponin T (cTnT).

Alternatively, the promoter may be, without limitation, a promoter from one of the following genes: α-myosin heavy chain gene, 6-myosin heavy chain gene, myosin light chain 2v (MLC-2v) gene, myosin light chain 2a gene, CARP gene, cardiac α-actin gene, cardiac m2 muscarinic acetylcholine gene, ANF, cardiac troponin C, cardiac troponin I, cardiac troponin T(cTnT), cardiac sarcoplasmic reticulum Ca-ATPase gene, skeletal α-actin; or an artificial cardiac promoter derived from MLC-2v gene.

In some embodiments, the rAAV vectors of the present disclosure further comprise a polyadenylation (pA) signal. Eukaryotic mRNAs are typically transcribed as a precursor mRNA. The precursor mRNA is processed to generate the mature mRNA, including a polyadenylation process. The process of polyadenylation begins as the transcription of a gene terminates. The 3'-most segment of the newly made precursor mRNA is first cleaved off by a set of proteins. These proteins then synthesize the poly(A) tail at the RNA's 3' end. The cleavage site typically contains the polyadenylation signal, e.g., AAUAAA. The poly(A) tail is important for the nuclear export, translation, and stability of mRNA.

In some embodiments, the rAAV vectors of the present disclosure comprise at least, in order from 5' to 3', a first adeno-associated virus (AAV) inverted terminal repeat (ITR) sequence, a promoter operably linked to a first transgene, an IRES operably linked to a second transgene, a polyadenylation signal, and a second AAV inverted terminal repeat (ITR) sequence.

In some embodiments, the rAAV is circular. In some embodiments, the rAAV vector is linear. In some embodiments, the rAAV vector is single-stranded. In some embodiments, the rAAV vector is double-stranded. In some embodiments, the rAAV vector is a self-complementary rAAV vector. Any rAAV vector described herein may be encapsidated by a viral capsid, such as an AAV6 capsid or any other serotype (e.g., a serotype that is of the same serotype as the ITR sequences).

A protein of interest may be a detectable marker or a therapeutic protein. A detectable marker may be a molecule that can be visualized (e.g., using a naked eye or under a microscope). In some embodiments, the detectable marker is a fluorescent molecule, a bioluminescent molecule, or a molecule that provides color (e.g., β-galactosidase, β-lactamases, β-glucuronidase and spheriodenone). In some embodiments, a detectable marker is a fluorescent protein or functional peptide or functional polypeptide thereof.

In some embodiments, a gene of interest encodes a therapeutic protein and is referred to as a "therapeutic gene." A therapeutic gene may provide a therapeutic effect in a cell, tissue or organ to which it is delivered. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid or protein for gene editing. In some embodiments, a gene of interest encodes a therapeutic RNA, e.g., a small interfering RNA.

In some embodiments, a therapeutic gene (e.g., a gene of interest) is a cardioprotective gene. Several cardioprotective genes are known, including heme oxygenase-1. This protein degrades the pro-oxidant heme and generates carbon monoxide and antioxidant bilirubin, conferring myocardial protection from ischemia/reperfusion injury. Franz et al., Circ. Res. 73:629-638, 1993. In inflammatory diseases, HO-1 is increased as a cytoprotective gene. However, it is usually insufficient in amount to stop the inflammation. The vigilant vector could provide an amplified amount of HO-1 when reduced oxygen indicates a need for HO-1. Another example of a cardioprotective gene is superoxide dismutase, which protects heart tissue from super oxide radicals generated during ischemia-reperfusion. Chen et al., Circulation 94:11412-11417, 1996; and Woo et al., Circulation 98:11255-11260, 1998. Genes that provide a protective effect from other cardiac disease states, such as heart degeneration and failure, may also be used in vectors of the invention. An example of a gene that improves cardiac function is phospholanban (PLN). The PLN gene product regulates the strength of each heartbeat and is known to malfunction in heart failure. Zvaritch et al., J. Biol. Chem. 275:14985-14991, 2000. Any suitable cardioprotective gene that provides a therapeutically effective level of protection may be used within vectors of the invention.

In some embodiments, a cardioprotective gene is a gene that is critical for signaling pathways in cardioprotection. In some embodiments, a cardioprotective gene is any one of: protectomiRs (e.g., microRNA 125b*), ZAC1 transcription factor, phospholanban (PLN), pro-inflammatory genes such as cycloxygenase (COX)-2 and inducible nitric oxide synthase (iNOS), antioxidant enzymes such as hemoxygenase (HO)-1, extracellular and manganese superoxidase dismutases (ec-SOD and Mg-SOD), heat shock proteins (HSPs), growth factors such as insulin like growth factor (IGF)-1 and hepatocyte growth factor (HGF), antiapoptotic proteins such as Bcl-2 and Bcl-xL, pro-apoptotic proteins such as FasL, Bcl-2, Bax, caspase-3 and p53, and proangiogenic genes such as TGFbeta, sphingosine kinase 1 (SPK1), apoptosis repressor with caspase recruitment domain (ARC), wild type cardiac troponin T, wild type cardiac myosin binding protein C, myosin light chains (either regulatory or essential), PI3K-Akt, and/or S100 variants.

S100 family proteins that may be used in accordance to the present disclosure include, without limitation, S100A1, S100A2, S100A3, S100A4, S100A5, S100A6, S100A7 (e.g., psoriasin), S100A8 (e.g., calgranulin A), S100A9 (e.g., calgranulin B), S100A10, S100A11, S100A12 (e.g., calgranulin C), S100A13, S100A14, S100A15 (e.g., koebnerisin), S100A16, S100B, S100P, and S100Z, or variants thereof.

In some embodiments, the S100 family protein may be S100 calcium-binding protein A1 (S100A1). In some embodiments, the S100A1 is cardiac S100A1 (cS100A1) or a variant thereof. The cS100A1 protein is a regulator of myocardial contractility. cS100A1 protein levels are reduced in right ventricular hypertrophied tissue in a model of pulmonary hypertension. Further, S100A1 is a regulator of the genetic program underlying cardiac hypertrophy, in that S100A1 inhibits alpha1 adrenergic stimulation of hypertrophic genes, including MYH7, ACTA1 and S100B.

In cardiomyocytes, S100A1 regulates the calcium-controlled network of SR, sarcomeric, and mitochondrial function through modulation of ryanodine receptor 2 (RYR2), sarco/endoplasmic reticulum Ca2+-ATPase (SERCA), titin, and mitochondrial F1-ATPase activity. As a result, cardiomyocytes and hearts with increased S100A1 expression show increased systolic and diastolic performance, a result of improved Ca2+ transient amplitudes resulting from augmented SR Ca2+ load and subsequent systolic Ca2+ release together with decreased diastolic SR Ca2+ leak and enhanced Ca2+ re-sequestration. Concurrently, S100A1 increases mitochondrial high-energy phosphate production and thus coordinates the energy supply with the increased adenosine 5'-triphosphate (ATP) demand by the enhanced cardiomyocyte Ca2+ turnover. Reduced S100A1 expression in cardiomyocytes is associated with reduced contractile function, corroborating the pathophysiological significance of this protein.

In some embodiments, the S100A1 cDNA (transgene) sequence of the polynucleotides of any of the disclosed rAAV vectors has 100% identity to a naturally-occurring human-derived S100A1 sequence. In other embodiments, the S100A1 cDNA sequence has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to a naturally-occurring S100A1 sequence.

In some embodiments, the S100A1 cDNA sequence is codon-optimized for expression in human cells. In other embodiments, the S100A1 cDNA sequence is codon-optimized for expression in canine cells.

Aspects of the present disclosure provide compositions and methods that include the delivery of a gene encoding an apoptotic inhibitor (e.g., an anti-apoptotic agent). Illustrative examples of apoptotic inhibitors include fink, p35, crmA, Bcl-2, Bcl-XL, Mcl-1, E1B-19K from adenovirus, as well as antagonists of pro-apoptotic agents (e.g., antisense, ribozymes, antibodies, etc.). In some embodiments, the apoptotic inhibitor is cardiac Apoptosis Repressor with Caspase Recruitment Domain (ARC), or a variant thereof. In other embodiments, the apoptotic inhibitor is cardiac ARC or a variant thereof. In some embodiments, it may be desirable to deliver an S100 family protein and the apoptotic inhibitor separately. In certain embodiments, a gene encoding the S100 family protein is delivered concurrently or sequentially with one or more small molecule apoptotic inhibitors. Other exemplary small-molecule apoptotic inhibitors include c-Myc inhibitors, Bax inhibitors, p53 inhibitors, tBid inhibitors, caspase inhibitors, and inhibitors of pro-apoptotic BCL-2 family members.

The cARC is an apoptotic regulatory protein expressed almost exclusively in myogenic cells. It contains a caspase recruitment domain (CARD) through which it blocks the activation of some initiator caspases. ARC also blocks caspase-independent events associated with apoptosis. Apoptosis caused by acute ischemia and subsequent ventricular remodeling is implicated as a mediator of heart failure. Although post-ischemic heart failure may have multiple causes, recent attention has been directed toward understanding the contribution of apoptosis or programmed cell death. Apoptosis is characterized by preservation of mitochondrial and sarcolemmal membranes, nuclear chromatin condensation, and phagocytosis by macrophages or neighboring cells without triggering an inflammatory response. The activation of apoptosis is known to occur through mechanisms involving caspases, a family of cysteine proteases that are synthesized as inactive precursors and proteolytically cleaved into their active form. ARC is able the block the activation of apoptosis by blocking the caspases.

In particular embodiments, the cARC cDNA sequence is codon-optimized for expression in human cells. In other embodiments, the cARC cDNA sequence is codon-optimized for expression in canine cells.

In some embodiments, a gene of interest encodes an antisense molecule. A number of antisense molecules that confer a cardioprotective effect are known, including antisense to angiotensin II type-1 receptor (Yang et al., Circulation 96:922-926, 1997; and Yang et al., Circ. Res. 83:552-559, 1998), antisense to adrenergic beta-1 receptor (Chen et al., Pharmacol. Exp. Ther. 294:722-727, 2000), and antisense to angiotensin-converting enzyme that has been shown to protect rat hearts from ischemia-reperfusion (Chen et al., Pharmacol. Exp. Ther. 294:722-727, 2000). In some embodiments, the antisense molecule is antisense to angiotensin II type-1 receptor, antisense to adrenergic beta-1 receptor, or antisense to angiotensin-converting enzyme.

In some embodiments, a nucleic acid vector comprised in an rAAV (e.g., an rAAV8) particle comprises one or more of the following: (a) one or more heterologous nucleic acid regions comprising gene of interest, and (b) one or more regions comprising inverted terminal repeat (ITR) sequences (e.g., wild-type ITR sequences or engineered ITR sequences) flanking the one or more nucleic acid regions (e.g., heterologous nucleic acid regions). In some embodiments, a nucleic acid vector in a rAAV particle comprises one or more nucleic acid regions comprising a control sequence that facilitates expression of the heterologous nucleic acid region (e.g., a promoter). In some embodiments, a nucleic acid vector in a recombinant AAV (e.g., rAAV8) particle comprises one or more nucleic acid regions comprising a sequence that facilitates integration of the heterologous nucleic acid region (optionally with the one or more nucleic acid regions comprising a sequence that facilitates expression) into the genome of the subject.

In some embodiments, the AAV is a fully constituted AAV containing the cap gene as modified by the invention, or an AAV capsid as modified by the invention carrying a transgene with the capsid protein supplied in trans. In some embodiments, empty capsids comprising the modified capsid proteins disclosed could be used to pre-treat prior to use of filled AAV capsids to further enhance transduction.

Described in Table 1 are exemplary rAAV capsid protein or related gene sequences of the present disclosure. The rAAV capsid proteins illustrated in Table 1 comprise the amino acid sequences set forth as SEQ ID NOs: 11-13, 15, 17, 19, 21, 23, 25, 27, 29, and 31.

The rAAV capsid proteins of the disclosure may comprise amino sequences that have at least 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to the sequences set forth as SEQ ID NOs: 11-13, 15, 17, 19, 21, 23, 25, 27, 29, and 31.

The rAAV capsid proteins illustrated in Table 1 are encoded by polynucleotides having the sequences set forth as SEQ ID NOs: 1, 3, 5, 14, 16, 18, 20, 22, 24, 26, 28, and 30. The rAAV capsid proteins of the disclosure may be encoded by nucleic acid sequences that have at least 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to the sequences set forth as SEQ ID NOs: 1, 3, 5, 14, 16, 18, 20, 22, 24, 26, 28, and 30.

As a practical matter, whether any particular nucleic acid molecule is at least 80%, 85%, 90%, 95%, 96%, 97%, 98%, or 99% identical to, for instance, the nucleotide sequence of a transgene, can be determined conventionally using known computer programs. A preferred method for determining the best overall match between a query sequence (e.g., a sequence of the present disclosure) and a subject sequence, also referred to as a global sequence alignment, can be determined using the FASTDB or blastn computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Whether a nucleotide is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. For subject sequences truncated at the 5' and/or 3' ends, relative to the query sequence, the percent identity is corrected by calculating the number of nucleotides of the query sequence that are positioned 5' to or 3' to the query sequence, which are not matched/aligned with a corresponding subject nucleotide, as a percent of the total bases of the query sequence.

In some embodiments, any of the disclosed rAAV amino acid vector sequences comprise truncations at the 5' or 3' end relative to the sequences of any one of SEQ ID NOs: 11-13, 15, 17, 19, 21, 23, 25, 27, 29, and 31. In some embodiments, any of the rAAV vectors comprise an amino acid sequence that differs from the sequence of any one of SEQ ID NOs: 11-13, 15, 17, 19, 21, 23, 25, 27, 29, and 31 by 1, 2, 3, 4, 5, 6, 7, 8, 9, 10, 11, 12, 13, 14, 15, 16, 17, 18, or more than 18 amino acids. In some embodiments, any of the disclosed rAAV nucleic acid vector sequences comprise truncations at the 5' or 3' end relative to the sequences of any one of SEQ ID NOs: 1, 3, 5, 14, 16, 18, 20, 22, 24, 26, 28, and 30. In some embodiments, any of the rAAV vectors are encoded by a nucleic acid sequence that differs from the sequence of any one of SEQ ID NOs: 1, 3, 5, 14, 16, 18, 20, 22, 24, 26, 28, and 30 by 1, 2, 3, 4, 5, 6, 7, 8, 9, 10, 11, 12, 13, 14, 15, 16, 17, 18, or more than 18 nucleic acids.

Method of Making rAAV Particles

Further provided herein are methods of making rAAV particles. The rAAV particles comprise a viral capsid and an rAAV vector as described herein, which is encapsidated by the viral capsid. Various methods of producing rAAV particles and nucleic acid vectors are known in the art and are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). In some embodiments, a vector (e.g., a plasmid) comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprise rep and/or cap genes that encode the Rep protein and/or Cap proteins. In some embodiments, the packaging is performed in vitro (e.g., outside of a cell).

In some embodiments, a nucleic acid vector (e.g., a plasmid) containing the gene of interest is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example, Addgene Catalog #37825-AAV8.T includes a helper plasmid hat comprises rep and the wild-type AAV8 cap gene (https://www.addgene.org/37825/#37825-AAV8).

ITR sequences and plasmids containing ITR sequences are known in the art and are commercially available (see, e.g., products and services available from Vector Biolabs, Philadelphia, Pa; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Genbank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO4-mediated transfection, lipids or polymeric molecules such as Polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Methods for large-scale production of AAV using a herpesvirus-based system are also known. See for example, Clement et al. (Hum Gene Ther. 2009, 20(8):796-806). Methods of producing exosome-associated AAV, which can be more resistant to neutralizing anti-AAV antibodies, are also known (Hudry et al., Gene Ther. 2016, 23(4):380-92; Macguire et al., Mol Ther. 2012, 20(5):960-71).

Methods for producing and using pseudotyped rAAV vectors are also known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Compositions

The present disclosure is also directed to compositions comprising one or more of the disclosed rAAV particles or preparations. In some embodiments, the rAAV preparation comprises an rAAV particle comprising a rAAV vector containing ITRs of a first serotype (e.g., AAV3, AAV5, AAV6, or AAV9) and capsid proteins encapsidating the rAAV vector. In some embodiments, the capsid proteins are of the first serotype (e.g., AAV3, AAV5, AAV6, or AAV9). In some embodiments, the preparation has at least a four-fold higher transduction efficiency (e.g., in a human hepatocellular carcinoma cell line, such as Huh7) compared to a preparation prepared using a rAAV vector containing AAV2 ITRs.

As described herein, such compositions may further comprise a pharmaceutical excipient, buffer, or diluent, and may be formulated for administration to host cell ex vivo or in situ in an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a human subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions which result in diseases or disorders as described herein.

Various formulations have been developed to facilitate rAAV particle use. For example, for administration of an injectable aqueous solution of rAAV particles, the solution may be suitably buffered, if necessary, and the liquid diluent first rendered isotonic with sufficient saline or glucose. In some embodiments, a composition as provided herein comprises a plurality of any one of the variant rAAV particles disclosed herein. In some embodiments, a composition comprises pluralities of more than one of the variant rAAV particles disclosed herein. In some embodiments, "administering" or "administration" means providing a material to a subject in a manner that is pharmacologically useful.

Accordingly, in some embodiments, a composition of variant rAAV particles comprises a pharmaceutically acceptable carrier. The term "carrier" refers to a diluent, adjuvant, excipient, or vehicle with which the rAAV particle is administered. Such pharmaceutical carriers can be sterile liquids (e.g., water, oils, saline solutions, aqueous dextrose and glycerol solutions), suspending agents, preserving agents (e.g., methyl-, ethyl-, and propyl-hydroxy-benzoates), and pH adjusting agents (such as inorganic and organic acids and bases). In some embodiments, carriers include buffered saline solutions (e.g., phosphate buffered saline, HEPES-buffered saline). USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, a composition comprising any one of the rAAV particles disclosed herein comprises Balanced Salt Solution (BSS) supplemented with 0.014% Tween 20 (polysorbate 20).

Typically, compositions may contain at least about 0.1% of the therapeutic agent (e.g., rAAV particle) or more, although the percentage of the active ingredient(s) may be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms of rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

Preparation of compositions for administration to a subject are known in the art. For example, a dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

rAAV Gene Therapy for Heart Diseases

The rAAV vectors, rAAV particles, or the composition comprising the rAAV particles of the present disclosure, may be used for gene therapy for heart diseases in a human subject in need thereof. Examples of heart disease that may be treated using the methods and compositions of the present disclosure include, but are not limited to, cardiomyopathy and acute ischemia. In some embodiments, the heart cardiomyopathy is hypertrophic cardiomyopathy or dilated cardiomyopathy. Heart failure caused by cardiomyopathy or other heart diseases, comprise two components, calcium handling dysfunction and apoptosis. The rAAV vectors, particles, and compositions comprising the rAAV particles may be used for treatment of such heart failures when administered to a subject in need thereof, e.g., via vascular delivery into the coronary arteries and/or direct injection to the heart. The rAAV vectors, particles, and compositions comprising the rAAV particles drive the concurrent expression of cS100A1 protein and ARC proteins in the cardiomyocytes of the subject. S100A1 improves aspects of calcium handling, including normalization of sarcoplasmic reticular calcium transients leading to normalization of contractile function. ARC will block apoptosis initiated by mitochondrial and nonmitochondrial mechanisms (such as stretch-induced apoptosis), as well as improve mitochondrial function. Thus, the synergistic benefits of the two proteins expressed by the transgenes of the present disclosure can lead to better long-term therapeutic outcomes by targeting both aspects of cardiomyopathy.

Methods of Transducing Cells

Any one of the rAAV particles, or compositions comprising any one of the rAAV particles disclosed herein can be used to transduce a cell, tissue or organ. In some embodiments, a cell, tissue or organ that is transduced using any one of the variant rAAV particles disclosed herein is transduced with a gene of interest that may be a therapeutic gene or one that is desired to study. In some embodiments, a cell, tissue or organ is transduced in an in vitro setting wherein the cell, tissue or organ is incubated or perfused with a media. A cell may be one of many cells cultured under certain conditions, or part of an organ that is harvested, part of an organoid, or an organism.

In some embodiments, a cell, tissue or organ is transduced in vivo, for example, for the purposes of treating a disease. In some embodiments, such a rAAV particle comprises a gene of interest that encodes a therapeutic protein or RNA.

In some embodiments, a composition comprising any one or more of the variant rAAV particles disclosed herein is provided to cells. In some embodiments, a composition comprising any one or more of the variant rAAV particles disclosed herein is provided to tissue in the CNS, to skeletal muscle, or to cardiac tissue. In some embodiments, a composition comprising rAAV particles is provided to cells via an in vivo, ex vivo, intraperitoneal, intravenous, intramuscular, intracoronary, subcutaneous, intrathecal, intracranial, intravesicular, or oral delivery method. In some embodiments, a composition comprising rAAV particles is provided to cells by intravenous, intramuscular, intracoronary or intrathecal injection or administration.

In some embodiments, a method of transducing cell with a gene of interest involves providing to the cell any one of the compositions provided herein. In some embodiments, a variant rAAV particle that is used to transduce cells with a gene of interest comprises SEQ ID NO: 11, 12 or 13.

Other aspects of the present disclosure relate to methods and preparations for use with a subject, such as human or non-human subjects, a host cell in situ in a subject, or a host cell derived from a subject. In some embodiments, a subject in which a cell, tissue or organ is transduced is a vertebrate animal (e.g., a mammal or reptile). In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a model for a particular disease or used to study the pharmacokinetics and/or pharmacokinetics of a protein or siRNA encoded by a gene of interest.

In some embodiments, the subject has or is suspected of having a heart disease that may be treated with gene therapy. In some embodiments, the subject is in any stages of heart failure. In some embodiments, the heart failure is caused by cardiomyopathy. In some embodiments, the heart failure is caused by hypertrophic cardiomyopathy or dilated cardiomyopathy.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host cell, tissue or organ. A therapeutically acceptable amount may be an amount that is capable of treating a disease. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The following examples are intended to be illustrative of certain embodiments of the present disclosure and are intended to be non-limiting.

EXAMPLES

Example 1

Three AAV variants ("SL1.2" (SEQ ID NO: 11), "SL2" (SEQ ID NO: 12), and "SL3" (SEQ ID NO: 13)) were

53

Figure 2:
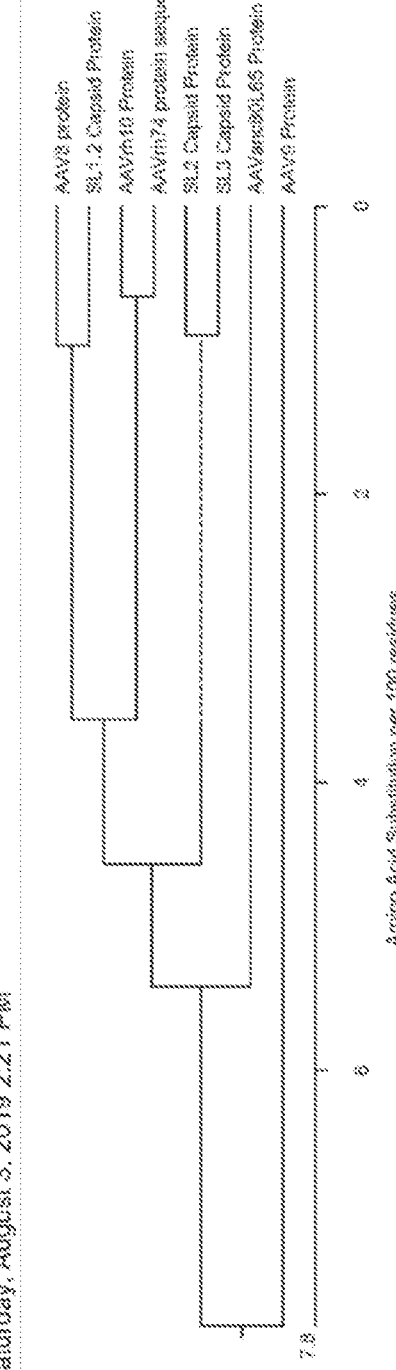
FIG. 2 depicts a "phylogenetic tree" of AAV variants SL1.2, SL2, SL3, AAV8, AAV9, AAVrh10, AAVrh74, and AAVanc80L65 based on the sequence of their capsid protein.
Figure 4A:
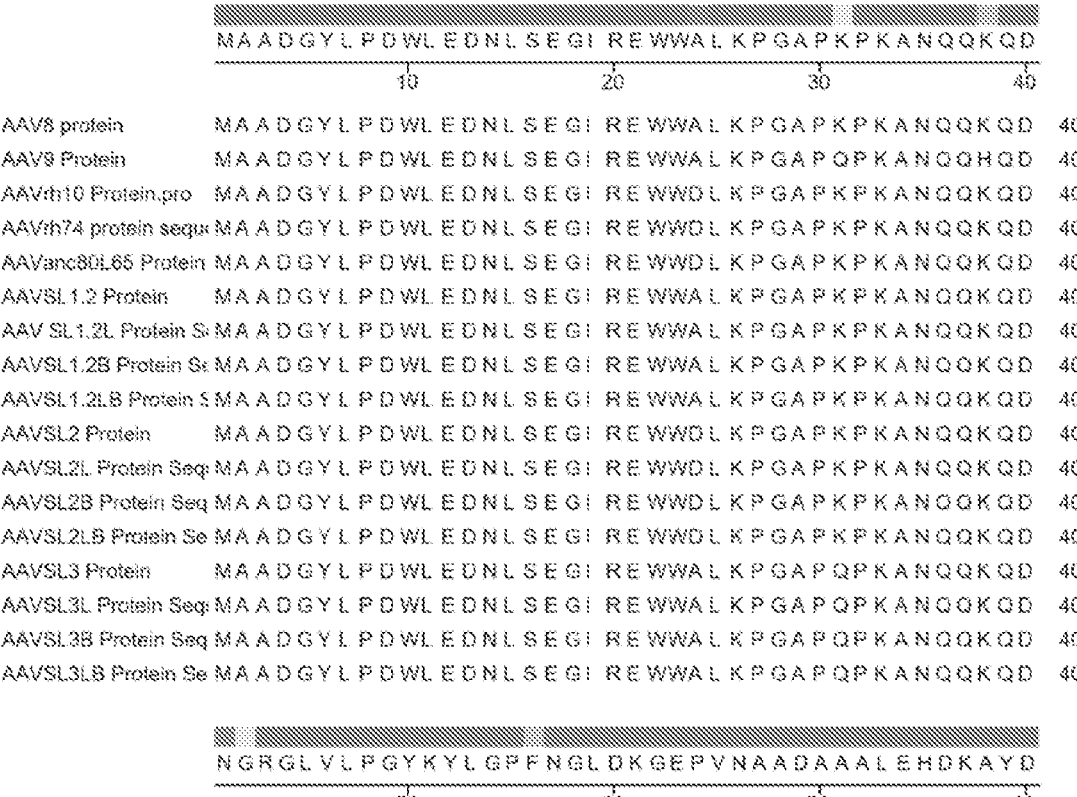
Figure 4I:
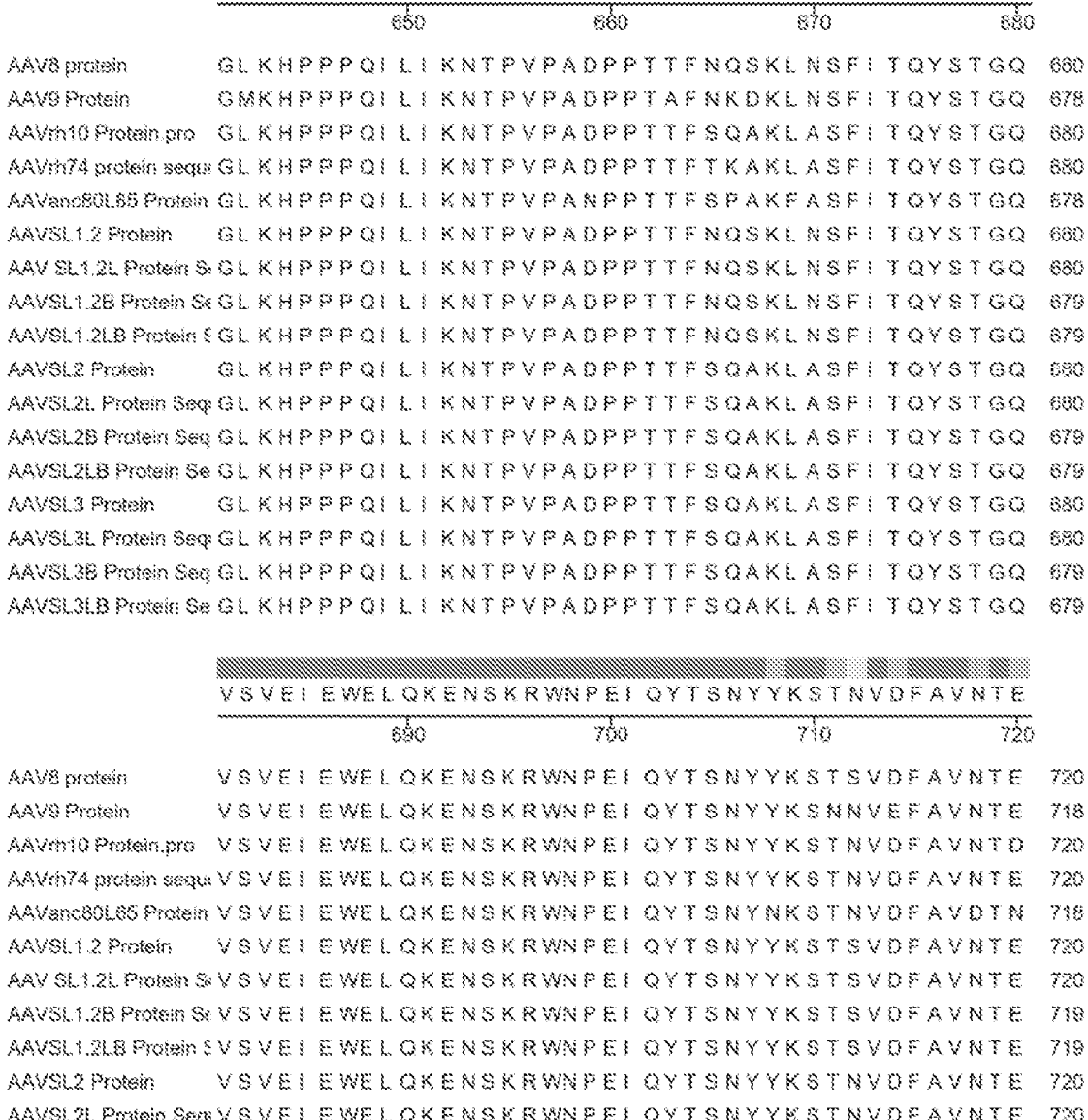

54 designed and created to alter the tropisms and/or efficiencies of AAV transduction as compared to AAV8. Transduction efficiency was increased by removing phosphorylation sites that decrease the efficiency of AAV8. To alter tropism, a rational design approach was taken in which the known tropism of AAV8 was compared to the tropism of AAV5, AAV9, AAVrh10, and AAV_ANC80L65, along with the sequence differences of the AAV capsids (see FIG. 1). Differences that correlated with improved cardiac and CNS tropism were then imported into the AAV8 capsid sequence. SL1.2, SL2, and SL3 represent escalating additions of such sequences. AAV-SL1.2 is thus closely related in sequence to AAV8, while AAV-SL2 and AAV-SL3 are more divergent, but more closely related to AAVr10, AAVrh74, and AAV8 than to AAV9 or AAVanc80L65. The phylogeny and percent divergences of SL1.2, SL2, and SL3 relative to the other AAV serotypes are shown in FIGS. 2 and 3, respectively.

Example 2

To improve the delivery of cardio-protective genes to the heart, mutant capsids were designed to alter regions that appear to be important for cardiac muscle uptake, based on comparisons with naturally occurring AAV serotypes. In particular, the capsid region spanning amino acids Glu578 to Gly596 were varied in the three variants described herein (SL1.2, SL2, and SL3; see Example 1 and FIGS. 1-3).

Figure 7:
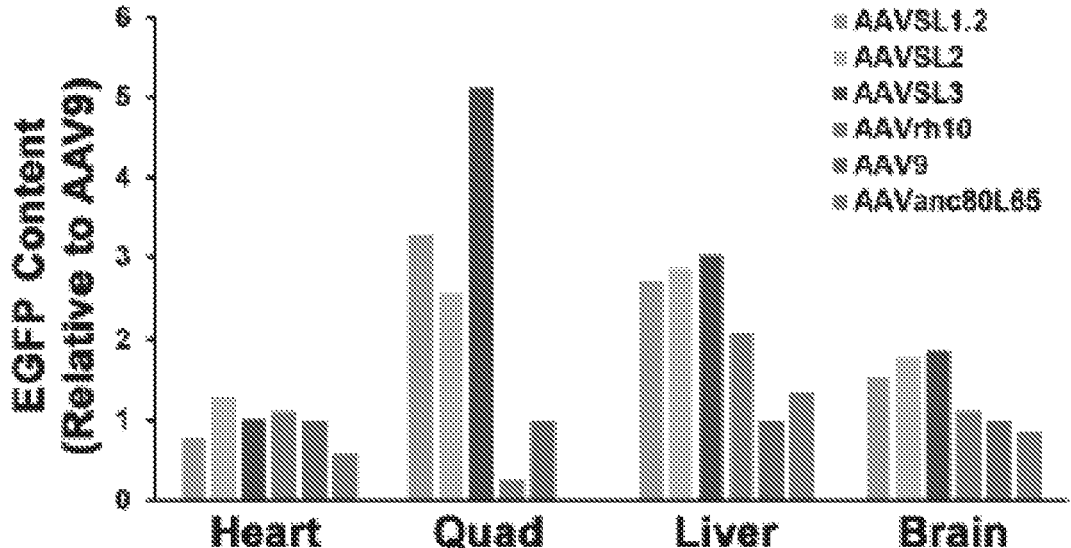
FIG. 7 shows the Western blot quantification of the blot shown in FIG. 8. The delivery of the three variants (SL1.2, SL2, and SL3) is compared to the uptake of the natural serotypes, AAV9 and AAVrh10, and the engineered variant, AAVanc80L65. The experiment was conducted using a known sub-saturating dose ($1 \times 10^{13}$ vg/kg) administered by tail vein systemic delivery into 6-month-old DBA/2J male mice. Green fluorescent protein (GFP) was used as the reporter protein under control of a beta-actin promoter for expression in all tissues. The variant SL2 has the improved uptake in cardiac tissue relative to the control serotypes, while SL3 has uptake more similar to AAV9. SL3 has highest uptake in skeletal muscle and brain of any of tested AAV serotype.
Figure 8:
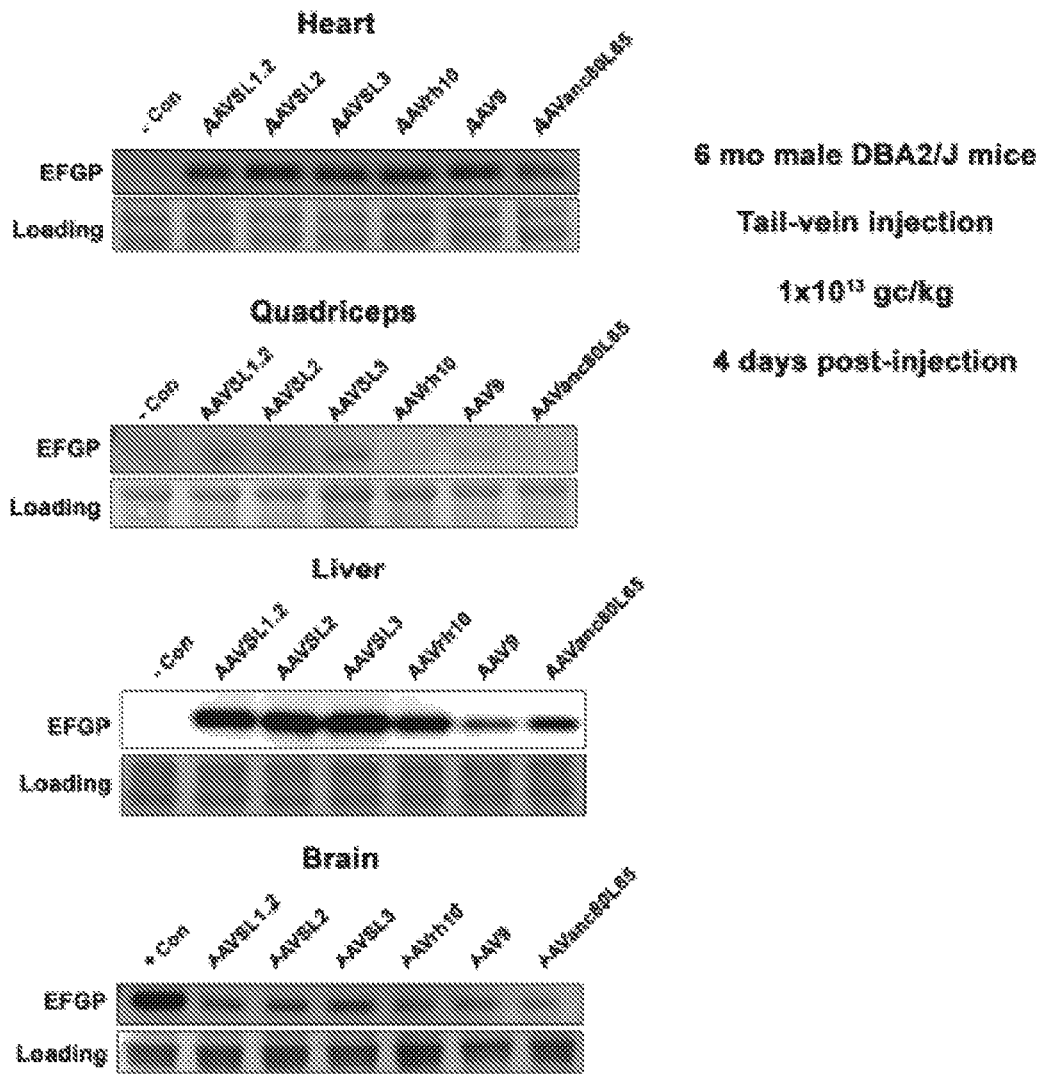
FIG. 8 shows the Western Blot data corresponding to the quantification shown in FIG. 7.

The Western blot quantification (FIG. 7) of the blot shown in FIG. 8 compares the delivery of the three variants (SL1.2, SL2, and SL3) to the uptake of the natural serotypes, AAV9 and AAVrh10, and the engineered variant, AAVanc80L65. AAV9 and AAVrh10 were selected because they are two of the best described AAV serotypes for cardiac delivery. The experiment was conducted using a known sub-saturating dose ($1\times10^{13}$ vg/kg) administered by tail vein systemic delivery into 6 month old DBA/2J male mice. Green fluorescent protein (GFP) was used as the reporter protein under control of a beta-actin promoter for expression in all tissues. FIGS. 7 and 8 show that the variant SL2 has the improved uptake in cardiac tissue relative to the control serotypes, while SL3 has uptake more similar to AAV9. It was observed that SL3 has highest uptake in skeletal muscle and brain of any of tested AAV serotype.

As shown in Table 2, it was also observed that the mutations that were introduced into SL2 and SL3 led to a substantial increase in the efficiency of production (e.g., the yield for a given amount of DNA). The efficiency of production for SL2 and SL3 increased such that the yields exceeded that of AAV9 and AAVrh10 by 1.5- to 4-fold, which far exceed the yields of the synthetic variant AAVanc80L65. AAVanc70L65 has been proposed to be more useful for cardiac delivery as compared to AAV8, but, based on the results described herein, is fact be inferior to AAV9, AAVrh10, and the present variants SL2 and SL3. The higher yields of SL2 and SL3 are important for the large-scale production needed for systemic human gene therapy, because these variants will be easier and less expensive to produce.

Figure 9:
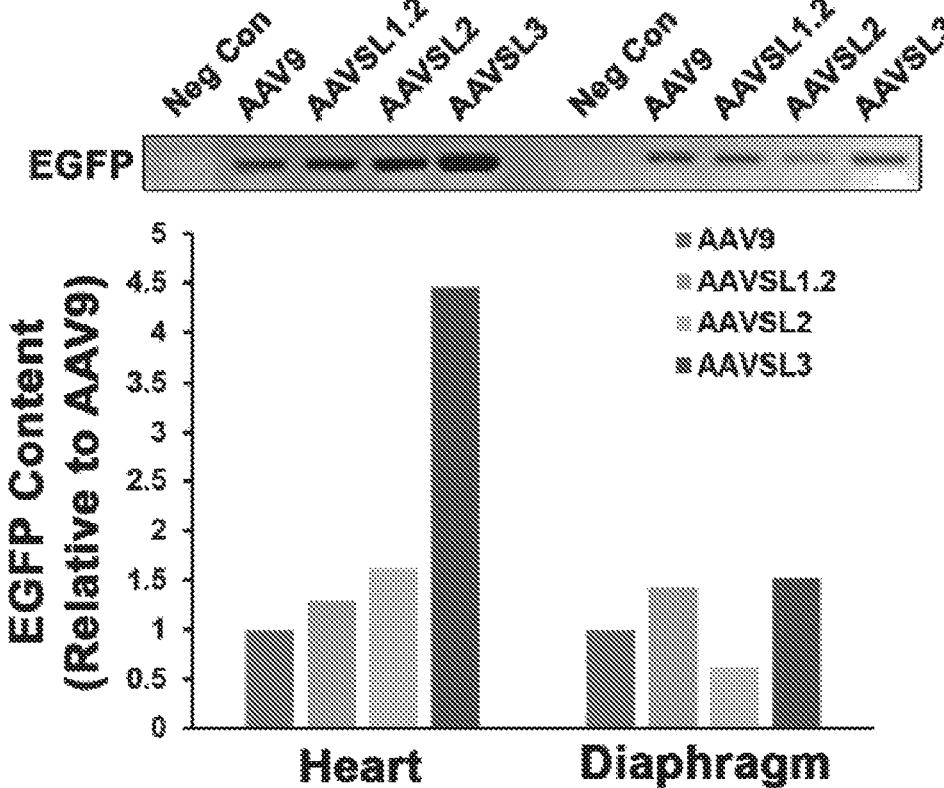
FIG. 9 shows the superiority of SL3 in facilitating uptake in both skeletal and cardiac muscles. A Western blot and quantification of heart and diaphragm are shown. The data was obtained by injecting $1 \times 10^{13}$ vg/kg of AAV9, SL1.2, SL2, or SL3 by tail vein (systemic delivery) into 6-month-old DBA/2J male mice. Green fluorescent protein (GFP) was used as the reporter protein under control of a beta-actin promoter for expression in all tissues.
Figure 10:
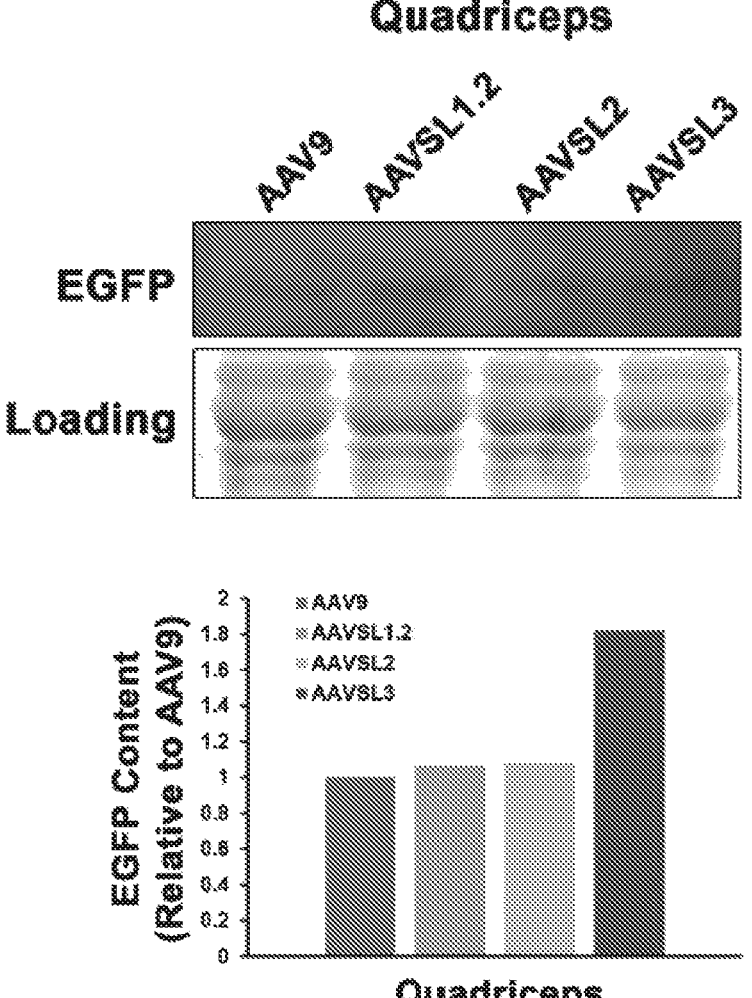
FIG. 10 shows the superiority of SL3 in facilitating uptake in both skeletal and cardiac muscles. A Western blot and quantification of quadriceps are shown. The data was obtained by injecting $1 \times 10^{13}$ vg/kg of AAV9, SL1.2, SL2, or SL3 by tail vein (systemic delivery) into 6-month-old DBA/2J male mice. Green fluorescent protein (GFP) was used as the reporter protein under control of a beta-actin promoter for expression in all tissues.

The superiority of SL3 in facilitating uptake in both skeletal and cardiac muscles is shown in FIG. 9 (Western blot and quantification of heart and diaphragm) and FIG. 10 (Western blot and quantification of quadriceps). The data in FIGS. 9 and 10 was obtained by injecting $1\times10^{13}$ vg/kg of AAV9, SL1.2, SL2, or SL3 by tail vein (systemic delivery) into 6 month old DBA/2J male mice. The reporter is GFP under control of the beta-actin promoter for expression in all tissues.

TABLE 2

Yield and efficiency for the variants SL1.2, SL2, and SL3 as compared to control serotypes AAV9, AAVrh10, and AAVanc80L65.

| Vector Prep | DNA (mg) | yield (gc) | Efficiency (gc/mg DNA) |
|---|---|---|---|
| AAV9 | 1.6 | 1.40E+13 | 8.75E+12 |
| AAVrh10 | 1.6 | 2.67E+13 | 1.67E+13 |
| AAVSL1.2 | 1.6 | 2.17E+13 | 1.36E+13 |
| AAVSL2 | 1.6 | 5.90E+13 | 3.69E+13 |
| AAVSL3 | 1.6 | 4.04E+13 | 2.53E+13 |
| AAVanc80L65 | 1.6 | 3.56E+12 | 2.23E+12 |

Figure 11:
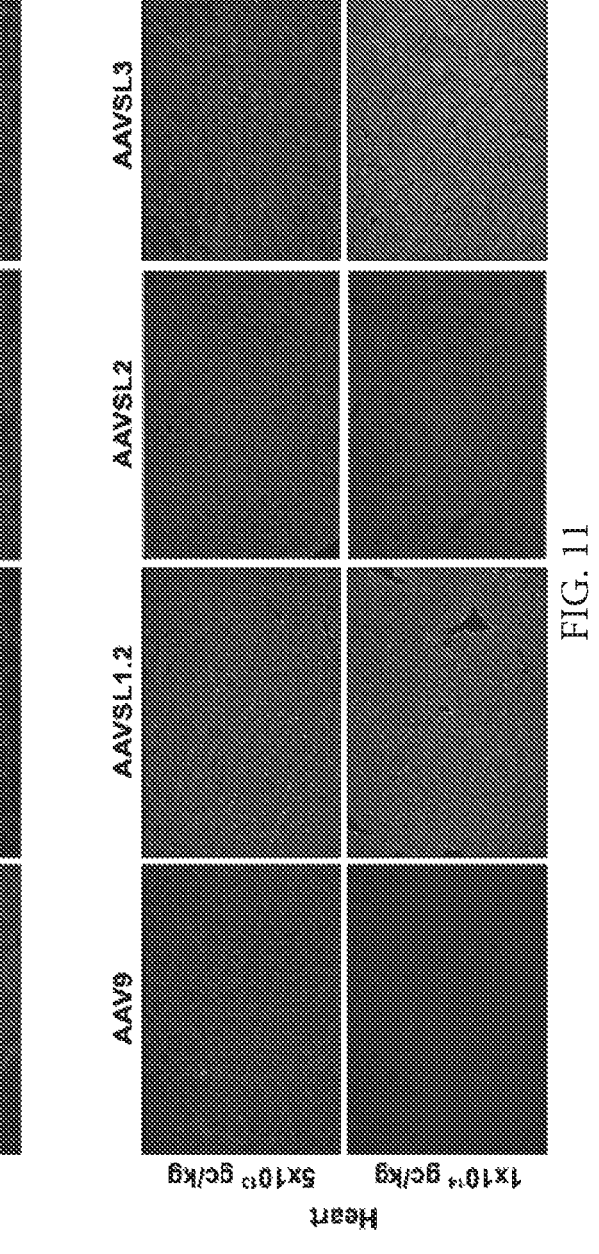
FIG. 11 demonstrates the distribution of Green Fluorescent Protein (GFP; degree of brightness) within skeletal muscles and the heart following systemic injection of AAV9, SL1.2, SL2, or SL3 at $5 \times 10^{13}$ vg/kg or $1 \times 10^{14}$ vg/kg. The pattern of expression supports the conclusions of the Western blot data, and indicate that SL3 is the superior vector for transduction of the heart and skeletal muscles.

FIG. 11 demonstrates the distribution of Green Fluorescent Protein (GFP; degree of brightness) within skeletal muscles and the heart following systemic injection of AAV9, SL1.2, SL2, or SL3 at $5\times10^{13}$ vg/kg or $1\times10^{14}$ vg/kg. The pattern of expression supports the conclusions of the Western blot data, and indicate that SL3 is the superior vector for transduction of the heart and skeletal muscles.

When designing new AAV vectors that are intended to target tissues other than the liver, it is useful to minimize delivery to the liver, which typically takes up more vector than any other tissue. In order to decrease the uptake of SL1.2, SL2, and SL3 by the liver, a single amino acid change (Asparagine 500 to Isoleucine) was introduced to each of SL1.2, SL2, and SL3 (see, e.g., Pulicherla, et al., Mol. Ther. 19:6, 1070-78 (2011)). The resultant vectors are designated herein as "SL1.2L" (SEQ ID NO: 15), "SL2L" (SEQ ID NO: 17), and "SL3L" (SEQ ID NO: 19).

In some applications, specifically where the central nervous system (CNS) is not a target, it is useful to prevent virus crossing the blood-brain barrier and thus minimize delivery to the brain. In order to decrease the uptake of SL1.2, SL2, and SL3 by the brain, seven amino acid changes (Asparagine 263 to Serine; Glycine 264 to Alanine; Threonine 265 to Serine; Serine 266 to Threonine; deletion of Glycine 268; Threonine 270 to Serine; and Threonine 274 to Histidine) were introduced to SL1.2, and eight amino acid changes (Asparagine 263 to Serine; Serine 264 to Alanine; Threonine 265 to Serine; Serine 266 to Threonine; deletion of Glycine 268; Serine 269 to Alanine; Threonine 270 to Serine; and Threonine 274 to Histidine) were introduced into each of SL2 and SL3 (see, e.g., Albright, et al., Mol. Ther. 26:2, 510-23 (2018)). The resultant vectors are designated herein as "SL1.2B" (SEQ ID NO: 21), "SL2B" (SEQ ID NO: 23), and "SL3B" (SEQ ID NO: 25).

Finally, it may in some cases be useful to utilize AAV vectors that have decreased uptake in both the liver and in the brain, relative to naturally occurring AAV serotypes. Accordingly, SL1.2, SL2, and SL3 variants were designed that integrate both the single amino acid change and the eight amino acid changes relating the liver and brain, respectively, described above. The resultant vectors are designated herein as "SL1.2LB" (SEQ ID NO: 27), "SL2LB" (SEQ ID NO: 29), and "SL3LB" (SEQ ID NO: 31).

Figure 5:
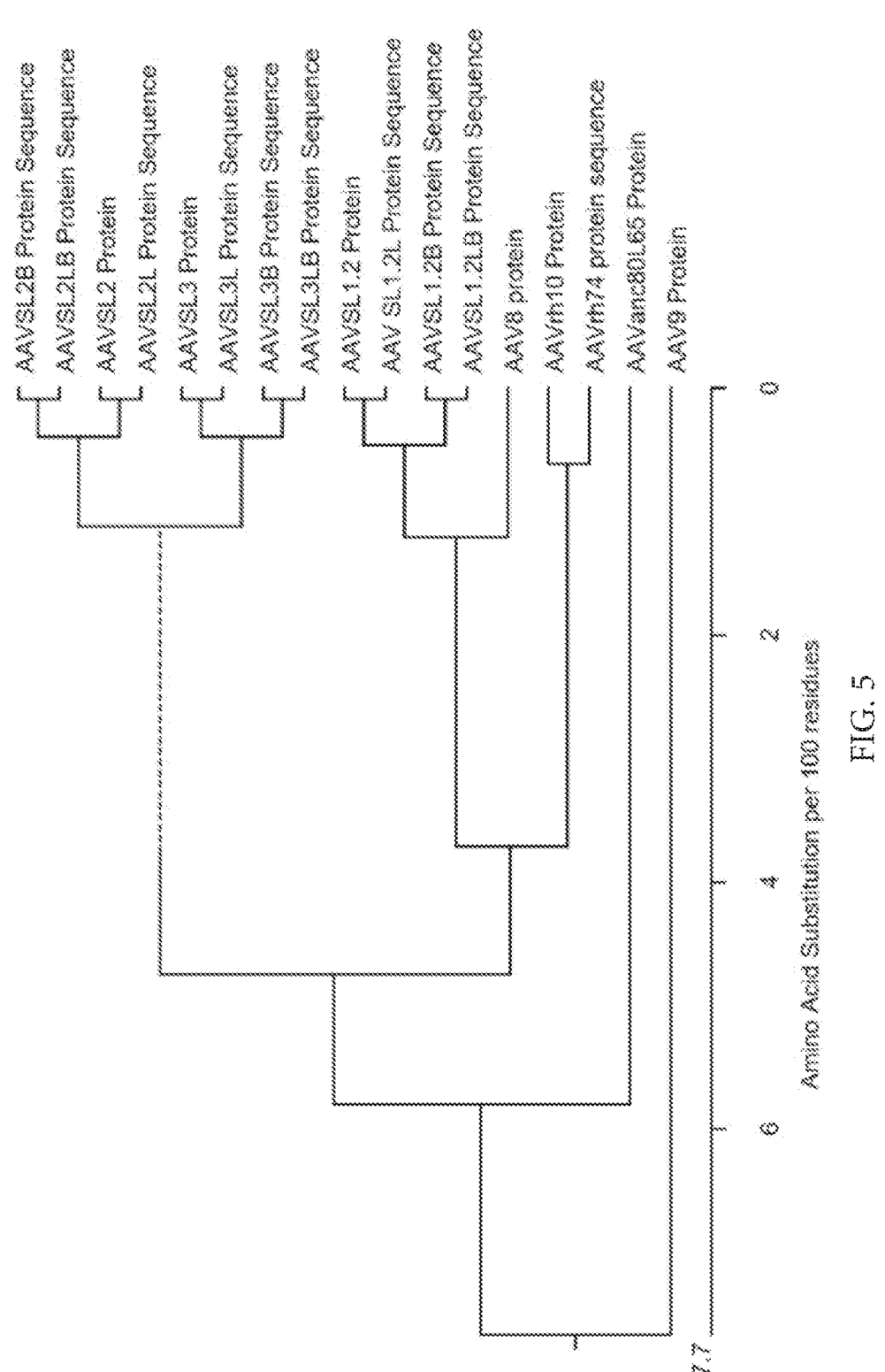
FIG. 5 depicts a "phylogenetic tree" of AAV variants SL1.2, SL1.2L, SL1.2B, SL1.2LB, SL2, SL2L, SL2B, SL2LB, SL3, SL3L, SL3B, SL3LB, AAV8, AAV9, AAVrh10, AAVrh74, and AAVanc80L65 based on the sequence of their capsid protein.

The phylogeny and percent divergences of SL1.2, SL1.2L, SL1.2B, SL1.2LB, SL2, SL2L, SL2B, SL2LB, SL3, SL3L, SL3B, and SL3LB relative to the other AAV serotypes are shown in FIGS. 5 and 6, respectively.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

REFERENCES

1. Kay C N, Ryals R C, Aslanidi G V, Min S H, Ruan Q, Sun J, Dyka F M, Kasuga D, Ayala A E, Van Vliet K, Agbandje-McKenna M, Hauswirth W W, Boye S L, Boye S E. *Targeting photoreceptors via intravitreal delivery using novel, capsid-mutated AAV vectors*. PLoS One. 2013 Apr. 26; 8(4):e62097.

That which is claimed is:

1. A variant recombinant adeno-associated virus (rAAV) capsid protein comprising the following substitutions:

(a) A24D, D41N, Q84K, R92K, T158A, K163S, R169K, L189I, A195G, V199L, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, E578Q, I581Q, T591A, Q594I, I595V, N665S, S667A, N670A, S712N, V722T, and Y733F, wherein the positions of the substitutions are based on the wild-type AAV8 capsid protein amino acid sequence set forth in SEQ ID NO: 7; or (b) K31Q, D41N, G42A, Q84K, R92K, Q105K, T158A, K163S, S180T, P201S, S225A, G264S, A269S, R313K, S315N, E350D, Q362E, Q413E, T415S, T417Q, Y447F, T453S, N459G, T462Q, G464L, N471S, T472N, A474S, N475A, T494V, A507G, G508A, N517D, A520V, T528S, D531E, D532G, N540S, N549G, A551G, A555V, D559K, I581Q, Q588S, Q589A, Q594I, I595V, N665S, S667A, N670A, S712N, V722T, and Y733F, wherein the positions of the substitutions are based on the wild-type AAV8 capsid protein amino acid sequence set forth in SEQ ID NO: 7.

2. The variant rAAV capsid protein of claim 1, wherein the rAAV capsid protein comprises an amino acid sequence as set forth in SEQ ID NO: 12.

3. A variant rAAV particle comprising the variant rAAV capsid protein of claim 1.

4. The variant rAAV particle of claim 3, further comprising a nucleic acid comprising a gene of interest.

5. The variant rAAV particle of claim 4, wherein the nucleic acid is single stranded.

6. The variant rAAV particle of claim 4, wherein the nucleic acid is double stranded.

7. A composition comprising a plurality of the variant rAAV particles of claim 3.

8. The composition of claim 7, further comprising a pharmaceutically acceptable carrier.

9. The variant rAAV capsid protein of claim 1, wherein the variant rAAV capsid protein further comprises any one or more of the following changes: N500I; N263S; T265S; S266T; deletion of G268; T270S; and T274H, wherein the positions of the changes are based on the wild-type AAV8 capsid protein amino acid sequence set forth in SEQ ID NO: 7.

10. The variant rAAV capsid protein of claim 9, wherein the variant rAAV capsid protein comprises an amino acid sequence as set forth in any one of SEQ ID NOS: 17, 23, 29, 19, 25, and 31.

11. The variant rAAV capsid protein of claim 1, wherein the rAAV capsid protein comprises an amino acid sequence as set forth in SEQ ID NO: 11.

12. The variant rAAV capsid protein of claim 1, wherein the rAAV capsid protein comprises an amino acid sequence as set forth in SEQ ID NO: 13.

13. A variant recombinant adeno-associated virus (rAAV) capsid protein comprising the amino acid sequence set forth in any one of SEQ ID NOS: 12, 17, 23, and 29.

14. A variant recombinant adeno-associated virus (rAAV) capsid protein comprising the amino acid sequence set forth in any one of SEQ ID NOS: 13, 19, 25, and 31.

15. A method of transducing a cell with a gene of interest, the method comprising providing to the cell the composition of claim 7, wherein the rAAV particles in the composition comprise a nucleic acid comprising a gene of interest.

16. The method of claim 15, wherein the cell is a mammalian cell.

17. The method of claim 16, wherein the cell is a human cell.

18. The method of claim 15, wherein the gene of interest encodes a therapeutic protein.

19. The method of claim 18, wherein the therapeutic protein is an antibody or antibody fragment, a peptibody, a growth factor, a hormone, a membrane protein, a cytokine, a chemokine, an activating or inhibitory peptide acting on cell surface receptors or ion channels, a cell-permeant peptide targeting intracellular processes, an enzyme, a nuclease or other protein used for gene editing.

20. The method of claim 15, wherein the gene of interest is a cardioprotective gene.

\* \* \* \* \*